{ United States Patent } [12]
Robinson et al.

(10) Patent No.: US 11,834,401 B2
(45) Date of Patent: *Dec. 5, 2023

(54) TREATING AND PREVENTING DISEASES BY MODULATING CELL MECHANICS

(71) Applicant: THE JOHNS HOPKINS UNIVERSITY, Baltimore, MD (US)

(72) Inventors: Douglas Robinson, Towson, MD (US); Alexandra Surcel, Baltimore, MD (US); Win Pin Ng, Berkeley, CA (US); Caren L. Freel Meyers, Towson, MD (US)

(73) Assignee: THE JOHNS HOPKINS UNIVERSITY, Baltimore, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/921,318

(22) Filed: Jul. 6, 2020

(65) Prior Publication Data
US 2020/0354301 A1 Nov. 12, 2020

Related U.S. Application Data

(63) Continuation of application No. 15/946,849, filed on Apr. 6, 2018, now Pat. No. 10,787,410, which is a continuation-in-part of application No. 15/103,665, filed as application No. PCT/US2014/070619 on Dec. 16, 2014, now abandoned.

(60) Provisional application No. 61/916,404, filed on Dec. 16, 2013.

(51) Int. Cl.
*C07C 49/825* (2006.01)
*A61P 35/00* (2006.01)
*A61K 31/12* (2006.01)
*A61K 31/136* (2006.01)
*A61K 31/15* (2006.01)
*A61K 31/27* (2006.01)
*A61K 45/06* (2006.01)
*C07C 271/58* (2006.01)
*C07C 275/30* (2006.01)
*C12Q 1/25* (2006.01)
*C12Q 1/02* (2006.01)
*C07C 251/80* (2006.01)

(52) U.S. Cl.
CPC ............ *C07C 49/825* (2013.01); *A61K 31/12* (2013.01); *A61K 31/136* (2013.01); *A61K 31/15* (2013.01); *A61K 31/27* (2013.01); *A61K 45/06* (2013.01); *A61P 35/00* (2018.01); *C07C 251/80* (2013.01); *C07C 271/58* (2013.01); *C07C 275/30* (2013.01); *C12Q 1/025* (2013.01); *G01N 2333/44* (2013.01); *G01N 2333/4712* (2013.01); *G01N 2500/10* (2013.01)

(58) Field of Classification Search
CPC ...... A61K 45/06; A61K 31/136; A61K 31/27; A61K 31/12; A61K 31/15; A61P 35/00; C07C 49/825; C07C 251/80; C07C 271/58; C07C 275/30
See application file for complete search history.

(56) References Cited

U.S. PATENT DOCUMENTS

| 4,724,234 A | 2/1988 | Cone, Jr. | |
| 4,935,450 A | 6/1990 | Cone, Jr. | |
| 2005/0239843 A1* | 10/2005 | Ding | C07D 417/12 514/326 |
| 2007/0026398 A1* | 2/2007 | Farnsworth | C12Q 1/42 435/6.16 |
| 2011/0009353 A1* | 1/2011 | Chen-Kiang | A61K 31/00 514/34 |

FOREIGN PATENT DOCUMENTS

WO 2003024967 A2 3/2003

OTHER PUBLICATIONS

'Definition of Cancer' at MedicineNet.com at https://web.archive.org/web/20120807164825/http://www.medterms.com/script/main/art.asp?articlekey=2580) (retrieved from the internet May 5, 2017) (Year: 2017).*
Sausville et al., in Cancer Research, 2006, vol. 66, pp. 3351-3354) (Year: 2006).*
Johnson et al. in British J. of Cancer, 2001, 84(10):1424-1431 (Year: 2001).*

(Continued)

*Primary Examiner* — Jared Barsky
(74) *Attorney, Agent, or Firm* — Fox Rothschild LLP

(57) ABSTRACT

Described are methods of treating or preventing a disease in a subject treatable by modulating cell mechanics. The method includes administering to a subject having or at risk for such a disease a pharmaceutical composition. comprising an agent selected from the group comprising a salt, solvate, or stereoisomer of compound (VIII) or its derivatives or a mixture of their constituents, where the compound has the formula:

(VIII)

18 Claims, 52 Drawing Sheets
Specification includes a Sequence Listing.

(56) References Cited

OTHER PUBLICATIONS

G. Cannon Chapter Nineteen in Burger's Medicinal Chemistry and Drug Discovery, Fifth Edition, vol. I: Principles and Practice, Wiley-Interscience 1995, pp. 783-802, 784 (Year: 1995).*
Nakamura et al., "Inhibitory effects of protocatechuic acid on the post-initiation phase of hamster pancreatic carcinogenesis induced by N-nitrosobis(2-oxopropyl)amine," Anticancer Research. Sep.-Oct. 2000;20(5B):3423-3427. (Year: 2000).*
Blagosklonny, "Analysis of FDA approved anticancer drugs reveals the future of cancer therapy," Cell Cycle. Aug. 2004;3(8):1035-42. Epub Aug. 16, 2004. (Year: 2004).*
Vallini, et al., Biodegredation of 4-(1-nonyl)phenol by axenic cultures of the yeast Candida aquaetextoris: identification of microbial breakdown products and proposal of a possible metabolic pathway. International Biodeterioration and Biodegradation 2001, 47, 133-140.
Tanihata, et al., Oxidative degradation of 4-hydroxyacetophenone in Arthrobacter sp. TGJ4. Bioscience, Biotechnology, and Biochemistry 2012, 76, 838-840.
Choi, et al., Cynanchum wilfordii ameliorates hypertension and endothelial dysfunction in rats fed with high fat/cholesterol diets. Immunopharmacology and Immunotoxicology 2011, 34, 4-11.
Choi, et al., Improved endothelial dysfunction by Cynanchum wilfordii in apolipoprotein E(-/-) mice fed a high fat/cholesterol diet. Journal of Medicinal Food 2012, 15, 169-179.
Jiang, et al., Chemical constituents of Cynanchum wilfordii and the chemotaxonomy of two species of the family Asclepiadacease, C. wilfordii and C. auriculatum. Archives of Pharmacal Research 2011, 34, 2021-2027.
Dolara, et al., Genetic toxicity of a mixture of fifteen pesticides commonly found in the Italian diet. Cell Biology and Toxicology 1993, 9, 333-343.
Akashi, et al., The role of the cytoskeleton in the polarized growth of the germ tube in Candida albicans. Microbiology 1994, 140, 271-280.
Hepler, et al., Isopropyl N-phenylcarbamate affects spindle microtubule orientation in dividing endosperm cells of Haemanthus katherinae Baker. Journal of Cell Science 1969, 5, 727-743.
Magistrini, et al., Effects of cold and of isopropyl-Nphenylcarbamate on the second meiotic spindle of mouse pocytes. European Journal of Cell Biology 1980, 22, 699-707.
Oliver, et al., A carbamate herbicide causes microtubule and microfilament disruption and nuclear fragmentation in fibroblasts. Experimental Cell Research 1978, 116, 229-237.
Walker, Cell cycle specificity of certain antimicrotubular drugs in Schizosaccharomyces pombe. Journal of General Microbiology 1982, 128, 61-71.
Clayton, et al., The relationship between the division plane and spindle geometry in Allium cells treated with CIPC and griseofulvin: an anti-tubulin study. European Journal of Cell Biology 1984, 34, 248-253.
Girdler, et al., Validating Aurora Bas an anti-cancer drug target. Journal of Cell Science 2006, 119, 3664-3675.
De Weger, et al., Cellular and clinical pharmacology of the taxanes docetaxel and paclitaxel—a review. Anticancer Drugs 2014. 25, 488-494.
Discher, et al., Tissue cells feel and respond to the stiffness of their substrate. Science 2005, 310, 1139-1143.
Bhadriraju, et al., Extracellular matrix- and cytoskeleton-dependent changes in cell shape and stiffness. Experimental Cell Research 2002, 278, 92-100.
Chiang, et al., Molecular basis of metastasis. New England Journal of Medicine 2008, 359, 2814-2823.
Wakatsuki, et al., Effects of cytochalasin D and latrunculin Bon mechanical properties of cells. Journal of Cell Science 2001, 114, 1025-1036.
Aronson, et al., Novel therapies in acute and chronic heart failure. Pharmacology and Therapeutics 2012, 135, 1-17.
Mona, et al., "Uncoupling activity of some n-phenylcarbamates" Pesticide Biochemistry and Physiology (1987) vol. 27, pp. 261-266.
Sausville, et al., "Contributions of human tumor xenografts to anticancer drug development" Cancer Research (2006) vol. 66, pp. 3351-3354.
Johnson, et al., "Relationships between drug activity in NCI preclinical in vitro and in vivo models and early clinical trials" British Journal of Cancer (2001) vol. 84, No. 10, pp. 1424-1431.
Definition of Cancer at MedicineNet.com at https://web.archive.org/web/20120807164825/http:I / www.medterms.com/script/main/art.asp?articlekey=2580) (retrieved from the internet May 5, 2017).
Moser, et al., Endothelial cell surface F1-F0 ATP synthase is active in ATP synthesis and is inhibited by angiostatin. Proceedings of the National Academy of Sciences of the United States of America 2001, 98, 6656-6661.
Malik, et al., Cardiac myosin activation: a potential therapeutic approach for systolic heart failure. Science 2011, 331, 1439-1443.
Straight, et al., Dissecting temporal and spatial control of cytokinesis with a myosin II Inhibitor. Science 2003, 299, 1743-1747.
Ostap, 2,3-Butanedione monoxime (BDM) as a myosin inhibitor. Journal of Muscle Research and Cell Motility 2002, 23, 305-308.
Ishihara, et al., Calyculin A and okadaic acid: inhibitors of protein phosphatase activity. Biochemical and Biophysical Research Communications 1989, 159, 871-877.
Ishihara, et al., Calcium-independent activation of contractile apparatus in smooth muscle by calyculin-A. The Journal of Pharmacology and Experimental Therapeutics 1989, 250, 388-396.
Makishima, et al., Induction of differentiation of human leukemia cells by inhibitors of myosin light chain kinase. FEBS Letters 1991, 287, 175-177.
Saitoh, et al., Selective inhibition of catalytic activity of smooth muscle myosin light chain kinase. Journal of Biological Chemistry 1987, 262, 7796-7801.
Uehata, et al., Calcium sensitization of smooth muscle mediated by a Rho-associated protein kinase in hypertension. Nature 1997, 389, 990-994.
Luo, et al., Understanding the cooperative interaction between myosin II and actin cross-linkers mediated by actin filaments during mechanosensation. Biophysical Journal 2012, 201, 238-247.
Murphy, et al., A myosin II mutation uncouples ATPase activity from motility and shortens step size. Nature Cell Biology 2001, 3, 311-315.
Reichl, et al., Interactions between myosin and actin crosslinkers control cytokinesis contractility dynamics and mechanics. Current Biology 2008, 18, 471-480.
Girard, et al., Dictyostelium myosin II mechanochemistry promotes active behavior of the cortex on long time scales. Proceedings of the National Academy of Sciences of the United States of America 2005, 103, 2103-2108.
Ren, et al., Mechanosensing through cooperative interactions between myosin II and the actin crosslinker cortexillin I. Current Biology 2009, 19, 1421-1428.
Luo, et al., Molecular mechanisms of cellular mechanosensing. Nature Materials 2013, 12, 1064-1071.
Kee, et al., A mechanosensory system governs myosin II accumulation in dividing cells. Molecular Biology of the Cell 2012, 23, 1510-1523.
Robinson, et al., Dynacortin, a Genetic Link between Equatorial Contractility and Global Shape Control Discovered by Library Complementation of a Dictyostelium discoideum Cytokinesis Mutant. Journal of Cell Biology 2000, 150, 823-838.
Ruppel, et al., Myosin motor function: structural and mutagenic approaches. Current Opinion in Cell Biology 1995, 7, 89-93.
Gerald, et al., A role for Dictyostelium race in cortical tension and cleavage furrow progression. Molecular Biosciences 1998, 141, 483-492.
Lakshmikanth, et al., A mitotic kinesin-like protein required for normal karyokinesis, myosin localization to the furrow, and cytokinesis in Dictyostelium. Proceedings of the National Academy of Sciences of the United States of America 2004, 101, 16519-16524.
Effler, et al., Mitosis-specific mechanosensing and contractileprotein redistribution control cell shape. Current Biology 2006, 16, 1962-1967.

(56) References Cited

OTHER PUBLICATIONS

Kee, et al., Micropipette aspiration for studying cellular mechanosensory responses and mechanics. Dictyostelium discoideum Protocols: Methods in Molecular BIology 2013, 983, 367-382.

Derganc, et al., Stability analysis of micropipette aspiration of neutrophils. Biophysics Journal 2000, 79, 153-162.

Octtaviani, et al., Enlazin, a Natural Fusion of Two Classes of Canonical Cytoskeletal Proteins, Contributes to Cytokinesis Dynamics. Molecular Biology of the Cell 2006, 17, 5275-5286.

Yumura, et al., Multiple Myosin II Heavy Chain Kinases: Roles in Filament Assembly Control and Proper Cytokinesis in Dictyostelium. Molecular Biology of the Cell 2005, 16, 4256-4266.

Zhou, et al., 14-3-3 coordinates microtubules, Rac, and myosin II to control cell mechanics and cytokinesis. Current Biology 2010, 20, 1881-1889.

Norstrom, et al., Unconventional processive mechanics of non-muscle myosin IIB. Journal of Biological Chemistry 2010, 285, 26326-26334.

Reichl, et al., Putting the brakes on cytokinesis with alpha-actinin. Developmental Cell 2007, 13, 460-462.

Betapudi, et al., Distinct roles of nonmuscle myosin II isoforms in the regulation of MDA-MB-231 breast cancer cell spreading and migration. Cancer Research 2006, 407, 673-686.

Betapudi, et al., A proteomic study of myosin II motor proteins during tumor cell migration. Journal of Molecular Biology 2011, 407, 673-686.

Heisenberg, et al., Forces in tissue morphogenesis and patterning. Cell 2013, 153, 948-962.

Mahajan, et al., Assembly Mechanism of Dictyostelium Myosin II: Regulation by K+, Mg2+, and Actin Filaments. Biochemistry 1996, 35, 15504-15514.

Delpu, et al., Genetic and epigenetic alterations in pancreatic carcinogenesis. Current Genomics 2011, 12, 15-24.

Neiderman, et al., Human platelet myosin. II. In vitro assembly and structure of myosin filaments. Journal of Cell Biology 1975, 67, 72-92.

Egelhoff, et al., Dictyostelium myosin heavy chain phosphorylation sites regulate myosin filament assembly and localization in vivo. Cell 1993, 75, 363-371.

Robinson, et al., Quantitation of the distribution and flux of myosin-II during cytokinesis. BMC Cell Biology 2002, 3:4.

Sun, et al., Competition between human cells by entosis. Cell Research 2014, 24, 1299-1310.

Maitra, et al., Global expression analysis of well-differentiated pancreatic endocrine neoplasms using oligonucleotide microarrays. Clinical Cancer Research 2003, 9, 5988-5995.

Maitra, et al., Multicomponent analysis of the pancreatic adenocarcinoma progression model using a pancreatic intraepithelial neoplasia tissue microarray. Modern Pathology 2003, 16, 902-912.

Tan, et al., Characterization of the tumorigenic and metastatic properties of a human pancreatic tumor cell line (AsPC-1) implanted orthotopically into nude mice. Tumour Biology 1985, 6, 89-98.

D'Apolito, et al., Cloning of the murine non-muscle myosin heavy chain IIA gene ortholog of human MYH9 responsible for May-Hegglin, Sebastian, Fechtner, and Epstein syndromes. Gene 2002, 286, 215-222.

Jones, et al., Core signaling pathways in human pancreatic cancers revealed by global genomic analyses. Science 2008, 321, 1801-1806.

Marina, et al., Non-muscle myosin heavy chain IIA and IIB interact and co-localize in living cells: relevance for MYH9-related disease. International Journal of Molecular Medicine 2006, 17, 729-736.

Even-Ram, et al., Of mice and men: Relevance of cellular and molecular characterizations of myosin IIA to MYH9-related human disease. Cell Adhesion and Migration 2007, 1, 152-155.

Dupont, et al., Role of YAP /TAZ in mechanotransduction. Nature 2011, 474, 179-183.

Calvo, et al., Mechanotransduction and YAP-dependent matrix remodelling is required for the generation and maintenance of cancer-associated fibroblasts. Nature Cell Biology 2013, 15, 637-646.

Liang, et al., Micro RNA let-7f inhibits tumor invasion and metastasis by targeting MYH9 in human gastric cancer. PLoS One 2011, 6, e18409.

Schramek, et al., Direct in vivo RNAi screen unveils myosin IIa as a tumor suppressor of squamous cell carcinomas. Science 2014, 343, 309-313.

Surcel, et al., Cytokinesis through biochemicalmechanical feedback loops. Seminars in Cell and Developmental Biology 2010, 21, 866-873.

Cross, et al., Nanomechanical analysis of cells from cancer patients. Nature Nanotechnology 2007, 2, 780-783.

\* cited by examiner

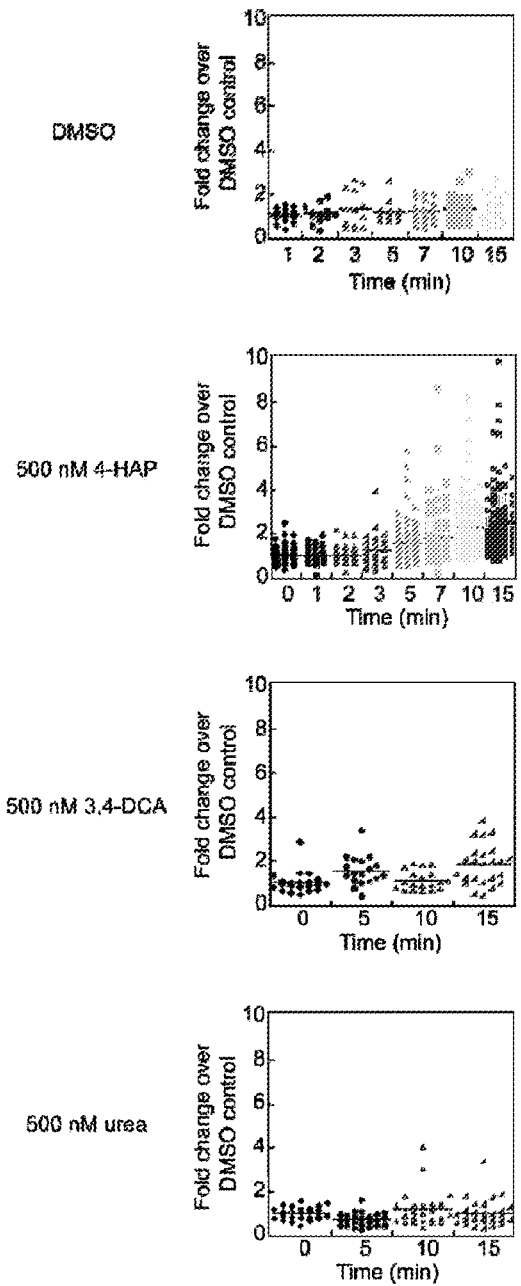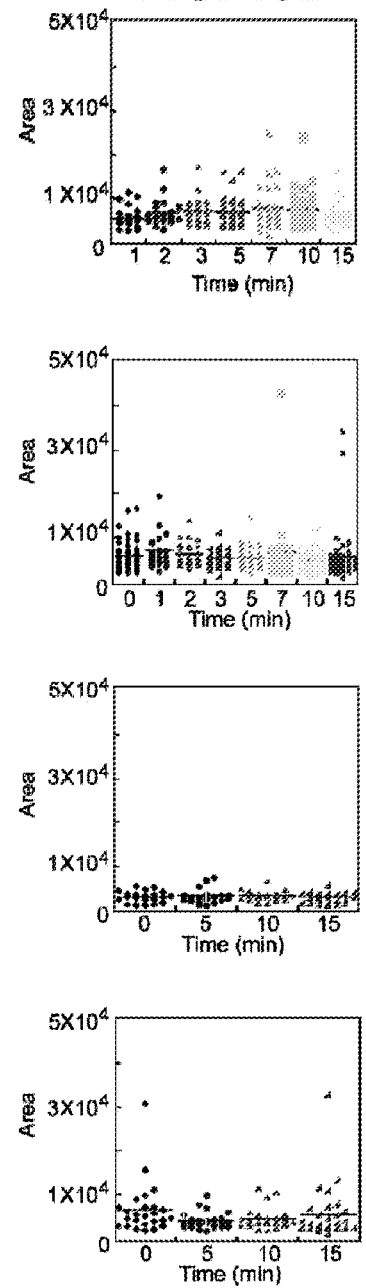

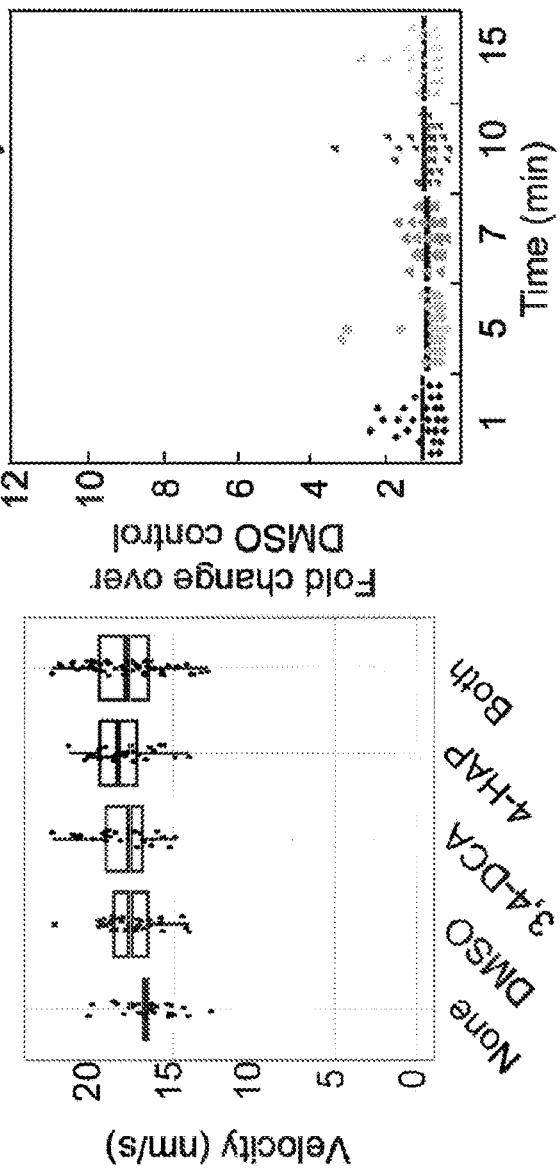
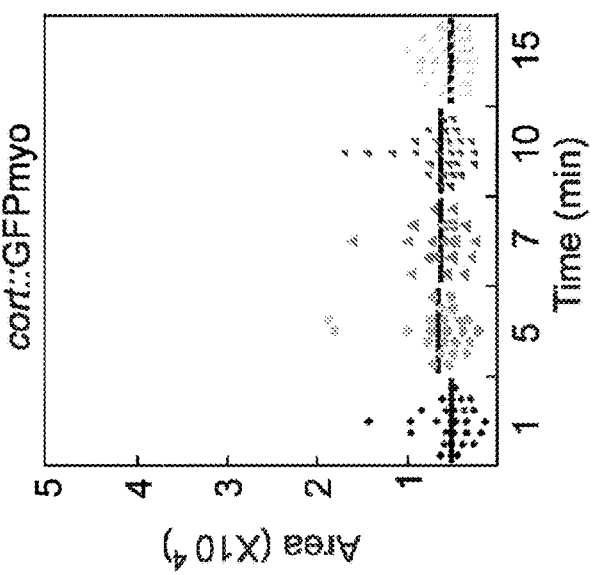
FIG. 15D
FIG. 15E
FIG. 15F

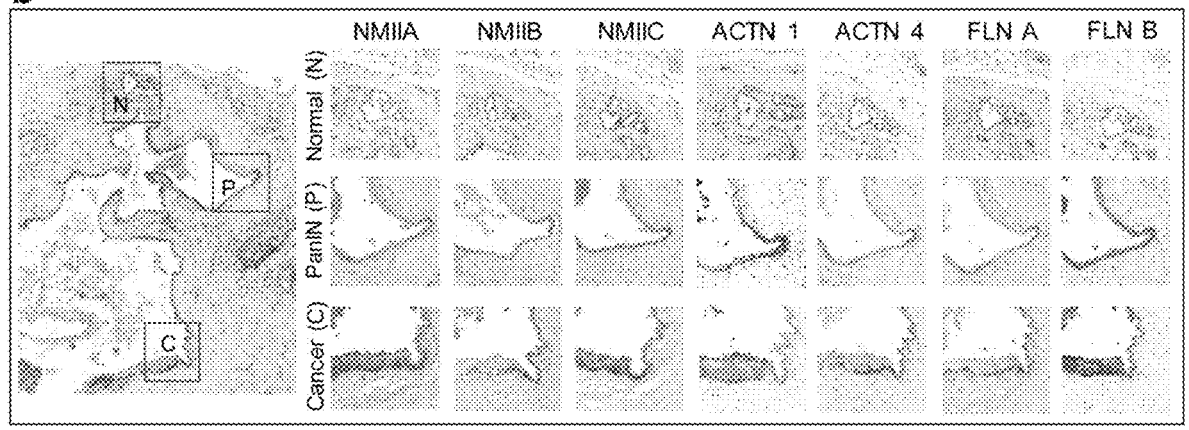
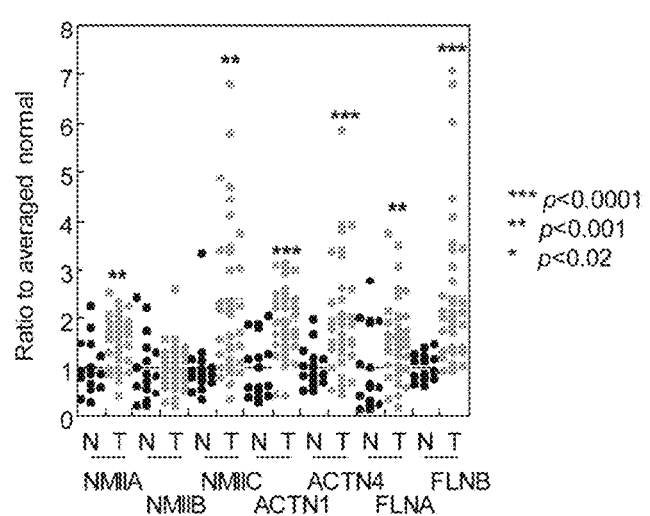
FIG. 23A-23C

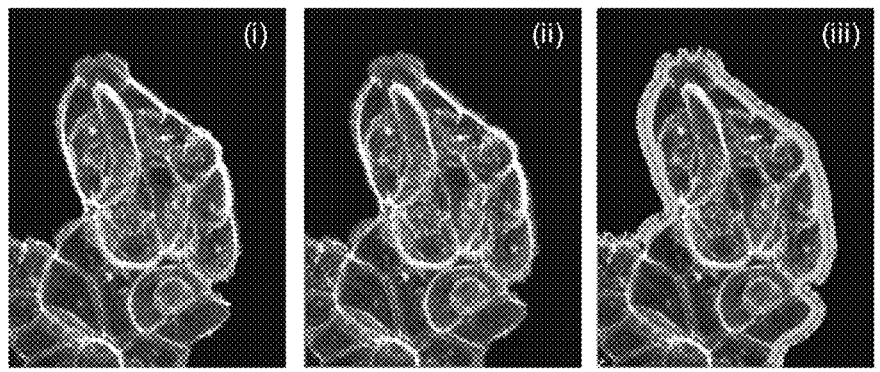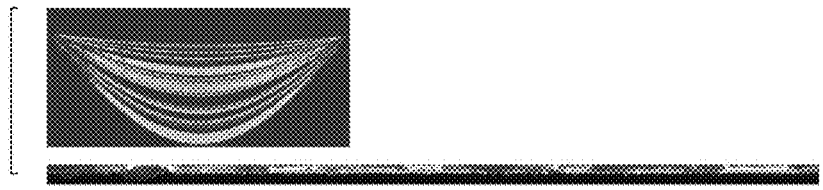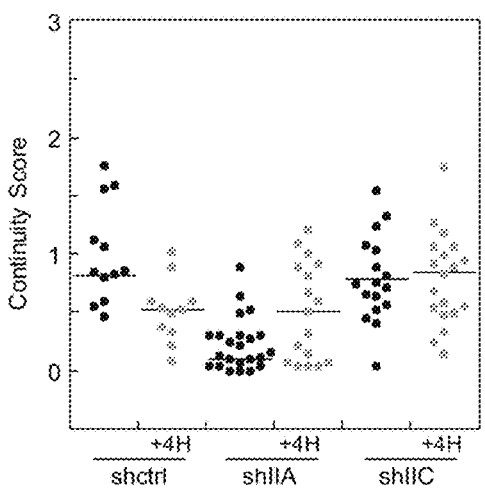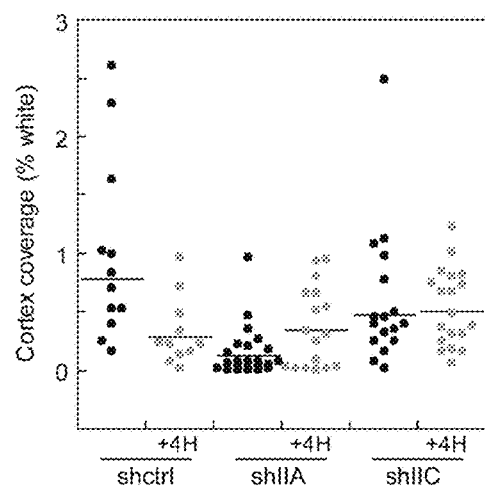
FIG. 26A-26C

SEQUENCE LISTING

```
<160> NUMBER OF SEQ ID NOS: 6

<210> SEQ ID NO 1
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 1

His His His His His His
1               5

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
caacaagatg aagagcacca a                                               21

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
gccaagctca agaacaagca t                                               21

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
gctcaaatat gaggccacaa t                                               21

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 5
caggacatgt tcatcgtcca t                                           21

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
gctgacattg aaatgccctt t                                           21
```

TREATING AND PREVENTING DISEASES BY MODULATING CELL MECHANICS

CROSS-REFERENCE TO RELATED APPLICATIONS

This application is a Continuation of U.S. patent application Ser. No. 15/946,849, filed Apr. 6, 2018, which is a Continuation-in-Part of U.S. patent application Ser. No. 15/103,665, filed Jun. 10, 2016, which is a 35 U.S.C. § 371 U.S. national entry of International Application PCT/US2014/070619, filed Dec. 16, 2014, which claims the benefit of U.S. Provisional Patent application 61/916,404, filed Dec. 16, 2013, which are hereby incorporated by reference for all purposes as if fully set forth herein.

The instant application contains a Sequence Listing which has been submitted electronically in ASCII format and is hereby incorporated by reference in its entirety. Said ASCII copy, created on Apr. 5, 2018, is named P12770-04_SL.txt and is 1,730 bytes in size.

STATEMENT REGARDING FEDERALLY SPONSORED RESEARCH

This invention was made with government support under grant number GM066817, awarded by National Institutes of Health. The government has certain rights in the invention.

BACKGROUND OF THE INVENTION

The present invention relates generally to compounds as activators of myosin II by promoting its assembly and recruitment to contractile structures in the cell and methods of using such compounds. These compounds may be used to modulate cell and tissue mechanics. This class of molecules, which activate the contractile system of the cell, may also be used for therapeutic and tissue engineering applications.

In the U.S., one in two people will develop cancer and one in three will acquire cardiovascular disease during their lifetime. These conditions depend on contractile systems driving the cell mechanics of division, mechanosensing, motility or cardiomyocyte contraction. Consequently, each may be impaired by molecules that modulate the cell's mechanical machinery. Cell mechanics are central to healthy and pathological states of cells, tissues and organ formation and function.

There are known major classes of myosin II modulating compounds. For example, Omecamtiv mecarbil (Cytokinetics, INC.) (Malik, Hartman, et al., 2011) is an activator of the catalytic activity of the myosin II motor by promoting tight binding to actin filaments and is specific for cardiac myosin II. Blebbistatin is an inhibitor of the myosin II motor domain and works by blocking phosphate release (Straight, Cheung, et al., 2003).

There are other known compounds that inhibit myosin II activity. For example, BDM inhibits the ATPase activity of skeletal myosin II (e.g., Ostap, 2002). Calyculin A targets PP1- and PP2A-type protein phosphatases and leads to increased myosin II activity (e.g., Ishihara, Martin, et al., 1989; Ishihara, Ozaki, et al., 1989). Myosin light chain phosphorylation inhibitors include myosin light chain kinase (MLCK) inhibitors, such as ML-7 (e.g. Makishima, Honma, et al., 1991; Saitoh, Ishikawa, et al., 1987), and Rho kinase (ROCK) inhibitors, such as Y-27632 (e.g., Uehata, Ishizaki, et al., 1997); these compounds reduce myosin activation.

Nevertheless, it would be desirable to identify small molecules for directly promoting myosin II accumulation and recruitment to contractile structures.

SUMMARY OF THE INVENTION

The present invention overcomes the aforementioned drawbacks by providing small molecules as myosin II activators for promoting myosin II accumulation and recruitment to contractile structures where cell tension and elasticity is increased.

In one embodiment, the present invention discloses a method for modulating cell mechanics of a disease condition in a subject comprising the step of administering an effective amount of a compound (I) or its derivatives, or a combination of their constituents, wherein the compound (I) has the formula:

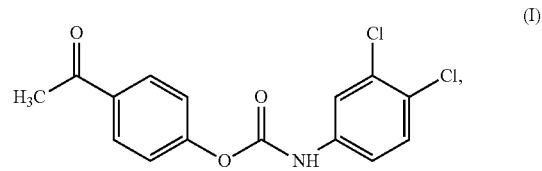 [SMILES: CC(=O)c1ccc(OC(=O)Nc2ccc(Cl)c(Cl)c2)cc1]

(I)

wherein myosin II is activated, cell mechanics are modulated and the disease condition is treated in the subject.

In one embodiment, the present invention discloses a method for modulating cell mechanics of a disease condition in a subject comprising the step of administering an effective amount of a compound (II) or its derivatives, or a combination of their constituents, wherein the compound (II) has the formula:

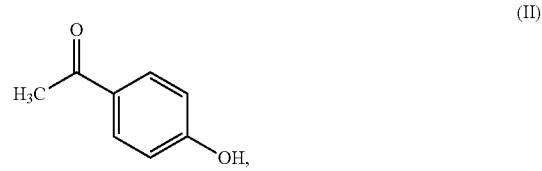

(II)

wherein myosin II is activated, cell mechanics are modulated and the disease condition is treated in the subject.

In one embodiment, the present invention discloses a method for modulating cell mechanics of a disease condition in a subject comprising the step of administering an effective amount of a compound (IV) or its derivatives, or a mixture of their constituents, wherein the compound (IV) has the formula:

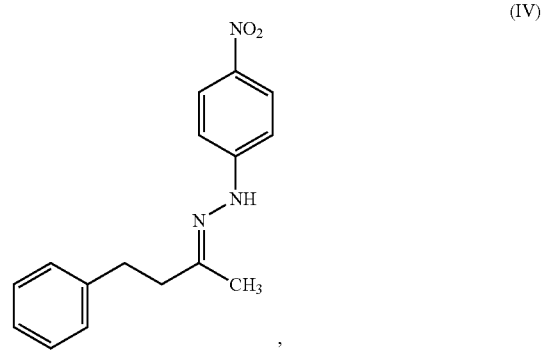 [SMILES: C/C(CCc1ccccc1)=N\Nc1ccc([N+](=O)[O-])cc1]

(IV)

wherein cytokinesis is modulated and the disease condition is treated in the subject.

In some embodiments, the present invention discloses compounds having formulas of I, II or IV for use in activating myosin II or inhibiting cytokinesis to treat a disease condition in a subject by systemic delivery.

In some embodiments, the present invention discloses pharmaceutical compositions for modulating cell mechanics of a disease condition in a subject comprising a compound having the formulas of I, II or IV. In one embodiment, the pharmaceutical compositions further comprise at least one pharmaceutically-acceptable carrier.

In one aspect, the present invention discloses an in vivo, large-scale and high-throughput screening method for identifying cell mechanical modulators. The screening method comprise the steps of (a) obtaining cells and placing the cells on multiple-well substrate plates for cytokinesis; (b) contacting the cells on multiple-well substrate plates with compound candidates; and (c) monitoring and analyzing the cytokinesis and the growth of the cells.

The foregoing and other aspects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

One embodiment of the present invention is a method for modulating cell mechanics in a subject. The method comprises the steps of administering to the subject an effective amount of compound (V) or its derivatives or a mixture of their constituents, where the compound has the formula:

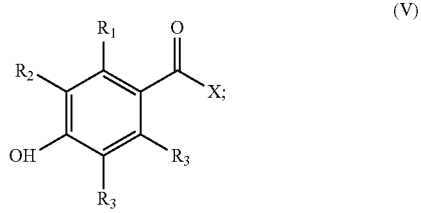

(V)

wherein $R_1$, $R_2$, $R_3$ and $R_4$ are independently represent H, OH, Halo, cyano, nitro, $C_1$-$C_6$ alkyl, carboxy $C_1$-$C_6$ alkyl, dicarboxy $C_1$-$C_6$ alkyl, $NR_5R_6$, wherein $R_5$ and $R_6$ are independently represent hydroxy, $C_1$ to $C_{10}$ alkyl, alkylamino, alkenyl, alkynyl, hydroxyalkyl, alkoxy, dialkylamino thioalkyl, thioalkenyl, thioalkynyl, aryloxy, acyloxy, thioacyl, amido, and sulphonamido, and wherein X is independently represent H, OH, $R_7$, $OR_7$, $NR_7R_8$, wherein $C_1$-$C_6$ alkyl, carboxy $C_1$-$C_6$ alkyl, dicarboxy $C_1$-$C_6$ alkyl, aryl, heteroaryl, alkenyl, alkynyl, hydroxyalkyl, alkoxy, dialkylamino thioalkyl, thioalkenyl, thioalkynyl, aryloxy, acyloxy, thioacyl, amido, and sulphonamido. Then modulating cell mechanics in the subject when compared to a reference subject that has not been administered the effective amount of compound (V). In addition, myosin II is activated in the subject compared to a reference subject that has not been administered the effective amount of compound (V). The compounds of the present invention may be administered by systemic delivery. For example, by oral, parenteral, intranasal, sublingual, rectal, and transdermal administration.

The methods of the present invention may further comprise the step of administering a bioactive agent such as a compound having a formula:

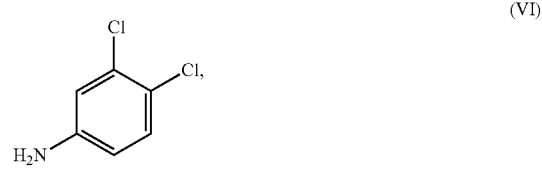

(VI)

a chemotherapy agent, or a combination thereof. The methods of the present invention may treat or prevent a subject that has a disease or at risk for getting a disease wherein the disease is treated or prevented by modulating the cell mechanics and/or activating myosin of the subject. An example of such a disease is cancer including pancreas or kidney cancer. The compound of formula V, may have the formula:

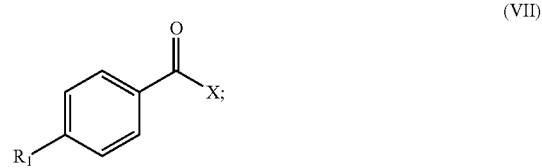

(VII)

wherein $R_1$ is OH, and wherein X is independently represent H, OH, $R_7$, $OR_7$, $NR_7R_8$, $C_1$-$C_6$ alkyl, carboxy $C_1$-$C_6$ alkyl, dicarboxy $C_1$-$C_6$ alkyl, aryl, heteroaryl, alkenyl, alkynyl, hydroxyalkyl, alkoxy, dialkylamino thioalkyl, thioalkenyl, thioalkynyl, aryloxy, acyloxy, thioacyl, amido, and sulphonamido.

Another embodiment of the present invention is a method for modulating cell mechanics in a subject. The method comprises the steps of administering an effective amount of compound (VIII) or its derivatives or a mixture of their constituents, where the compound has the formula:

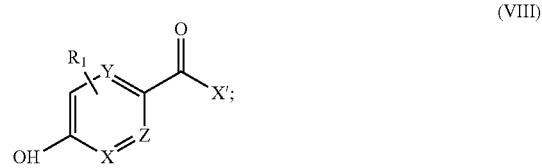

(VIII)

wherein X, Y, and Z can independently be N or C, with the proviso that X, Y, and Z cannot all be N, and wherein $R_1$ is H, OH, Halo, cyano, nitro, $C_1$-$C_6$ alkyl, carboxy $C_1$-$C_6$ alkyl, dicarboxy $C_1$-$C_6$ alkyl, $NR_2R_3$, wherein $R_2$ and $R_3$ are independently represent hydroxy, $C_1$ to $C_{10}$ alkyl, alkylamino, alkenyl, alkynyl, hydroxyalkyl, alkoxy, dialkylamino thioalkyl, thioalkenyl, thioalkynyl, aryloxy, acyloxy, thioacyl, amido, and sulphonamido, and wherein X' is independently represent H, OH, $R_7$, $OR_7$, $NR_7R_8$, wherein $R_7$ and $R_8$ are independently $C_1$-$C_6$ alkyl, carboxy $C_1$-$C_6$ alkyl, dicarboxy $C_1$-$C_6$ alkyl, aryl, heteroarylalkenyl, alkynyl, hydroxyalkyl, alkoxy, dialkylamino thioalkyl, thioalkenyl, thioalkynyl, aryloxy, acyloxy, thioacyl, amido, or and sulphonamido. Then modulating cell mechanics in the subject when compared to a reference subject that has not been administered the effective amount of compound (VIII). Also, myosin II is activated in the subject compared to a reference subject that has not been administered the effective amount of compound (VIII).

Another embodiment of the present invention is a compound having the formula:

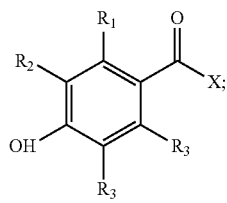

(V)

wherein $R_1$, $R_2$, $R_3$ and $R_4$ are independently represent H, OH, Halo, cyano, nitro, $C_1$-$C_6$ alkyl, carboxy $C_1$-$C_6$ alkyl, dicarboxy $C_1$-$C_6$ alkyl, $NR_5R_6$, wherein $R_5$ and $R_6$ are independently represent hydroxy, $C_1$ to $C_{10}$ alkyl, alkylamino, alkenyl, alkynyl, hydroxyalkyl, alkoxy, dialkylamino thioalkyl, thioalkenyl, thioalkynyl, aryloxy, acyloxy, thioacyl, amido, and sulphonamido, and wherein X is independently represent H, OH, $R_7$, $OR_7$, $NR_7R_8$, wherein $C_1$-$C_6$ alkyl, carboxy $C_1$-$C_6$ alkyl, dicarboxy $C_1$-$C_6$ alkyl, aryl, heteroaryl, alkenyl, alkynyl, hydroxyalkyl, alkoxy, dialkylamino thioalkyl, thioalkenyl, thioalkynyl, aryloxy, acyloxy, thioacyl, amido, and sulphonamido. The compound may be used in activating myosin II and/or modulating cell mechanics to treat a disease in a subject. The compound having formula 5 may have the formula:

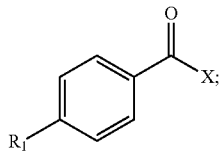

(VII)

wherein $R_1$ is OH, and wherein X is independently represent H, OH, $R_7$, $OR_7$, $NR_7R_8$, wherein $C_1$-$C_6$ alkyl, carboxy $C_1$-$C_6$ alkyl, dicarboxy $C_1$-$C_6$ alkyl, aryl, heteroaryl, alkenyl, alkynyl, hydroxyalkyl, alkoxy, dialkylamino thioalkyl, thioalkenyl, thioalkynyl, aryloxy, acyloxy, thioacyl, amido, and sulphonamido.

Another embodiment of the present invention is a compound of the formula:

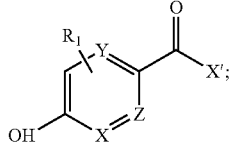

(VIII)

wherein X, Y, and Z can independently be N or C, with the proviso that X, Y, and Z cannot all be N, and wherein $R_1$ is H, OH, Halo, cyano, nitro, $C_1$-$C_6$ alkyl, carboxy $C_1$-$C_6$ alkyl, dicarboxy $C_1$-$C_6$ alkyl, $NR_2R_3$, wherein $R_2$ and $R_3$ are independently represent hydroxy, $C_1$ to $C_{10}$ alkyl, alkylamino, alkenyl, alkynyl, hydroxyalkyl, alkoxy, dialkylamino thioalkyl, thioalkenyl, thioalkynyl, aryloxy, acyloxy, thioacyl, amido, and sulphonamido, and wherein X' is independently represent H, OH, $R_7$, $OR_7$, $NR_7R_8$, wherein $R_7$ and $R_8$ are independently $C_1$-$C_6$ alkyl, carboxy $C_1$-$C_6$ alkyl, dicarboxy $C_1$-$C_6$ alkyl, aryl, heteroarylalkenyl, alkynyl, hydroxyalkyl, alkoxy, dialkylamino thioalkyl, thioalkenyl, thioalkynyl, aryloxy, acyloxy, thioacyl, amido, or sulphonamido. Then modulating cell mechanics in the subject when compared to a reference subject that has not been administered the effective amount of compound (VIII). Also, myosin II is activated in the subject compared to a reference subject that has not been administered the effective amount of compound (VIII).

Another embodiment of the present invention is a pharmaceutical composition for modulating cell mechanics of a disease in a subject comprising a compound having the formula:

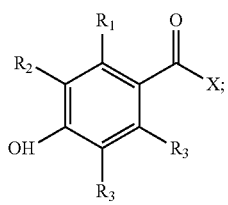

(V)

wherein $R_1$, $R_2$, $R_3$ and $R_4$ are independently represent H, OH, Halo, cyano, nitro, $C_1$-$C_6$ alkyl, carboxy $C_1$-$C_6$ alkyl, dicarboxy $C_1$-$C_6$ alkyl, $NR_5R_6$, wherein $R_5$ and $R_6$ are independently represent hydroxy, $C_1$ to $C_{10}$ alkyl, alkylamino, alkenyl, alkynyl, hydroxyalkyl, alkoxy, dialkylamino thioalkyl, thioalkenyl, thioalkynyl, aryloxy, acyloxy, thioacyl, amido, and sulphonamido, and wherein X is independently represent H, OH, $R_7$, $OR_7$, $NR_7R_8$, wherein $C_1$-$C_6$ alkyl, carboxy $C_1$-$C_6$ alkyl, dicarboxy $C_1$-$C_6$ alkyl, aryl, heteroaryl, alkenyl, alkynyl, hydroxyalkyl, alkoxy, dialkylamino thioalkyl, thioalkenyl, thioalkynyl, aryloxy, acyloxy, thioacyl, amido, and sulphonamido; wherein the pharmaceutical composition further comprises at least one pharmaceutically-acceptable carrier. This pharmaceutical composition may comprise the compound having the formula (V) having the formula:

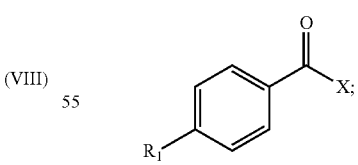

(VII)

wherein $R_1$ is OH, and wherein X is independently represent H, OH, $R_7$, $OR_7$, $NR_7R_8$, wherein $C_1$-$C_6$ alkyl, carboxy $C_1$-$C_6$ alkyl, dicarboxy $C_1$-$C_6$ alkyl, aryl, heteroaryl, alkenyl, alkynyl, hydroxyalkyl, alkoxy, dialkylamino thioalkyl, thioalkenyl, thioalkynyl, aryloxy, acyloxy, thioacyl, amido, and sulphonamido. In addition, the pharmaceutical compositions of the present invention may further comprises a compound having the formula:

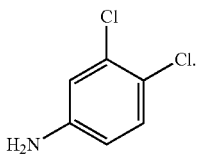

(VI)

Another embodiment of the present invention is a pharmaceutical composition for modulating cell mechanics of a disease in a subject comprising a compound having the formula:

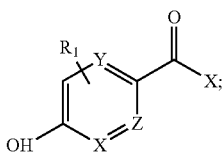

(VIII)

wherein X, Y, and Z can independently be N or C, with the proviso that X, Y, and Z cannot all be N, and wherein $R_1$ is H, OH, Halo, cyano, nitro, $C_1$-$C_6$ alkyl, carboxy $C_1$-$C_6$ alkyl, dicarboxy $C_1$-$C_6$ alkyl, $NR_2R_3$, wherein $R_2$ and $R_3$ are independently represent hydroxy, $C_1$ to $C_{10}$ alkyl, alkylamino, alkenyl, alkynyl, hydroxyalkyl, alkoxy, dialkylamino thioalkyl, thioalkenyl, thioalkynyl, aryloxy, acyloxy, thioacyl, amido, and sulphonamido, and wherein X is independently represent H, OH, $R_7$, $OR_7$, $NR_7R_8$, wherein $C_1$-$C_6$ alkyl, carboxy $C_1$-$C_6$ alkyl, dicarboxy $C_1$-$C_6$ alkyl, aryl, heteroaryl, alkenyl, alkynyl, hydroxyalkyl, alkoxy, dialkylamino thioalkyl, thioalkenyl, thioalkynyl, aryloxy, acyloxy, thioacyl, amido, and sulphonamido; wherein the pharmaceutical composition further comprises at least one pharmaceutically-acceptable carrier.

Another embodiment of the present invention is a method of treating or preventing cancer in a subject comprising the steps of: administering to a subject having cancer or at risk for cancer a pharmaceutical composition. The pharmaceutical composition comprises an agent selected from the group comprising a salt, solvate, or stereoisomer of compound (I) or its derivatives or a mixture of their constituents, where the compound has the formula:

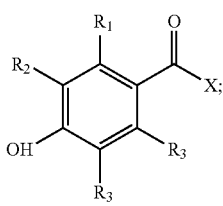

(V)

wherein $R_1$, $R_2$, $R_3$ and $R_4$ are independently represent H, OH, Halo, cyano, nitro, $C_1$-$C_6$ alkyl, carboxy $C_1$-$C_6$ alkyl, dicarboxy $C_1$-$C_6$ alkyl, $NR_5R_6$, wherein $R_5$ and $R_6$ are independently represent hydroxy, $C_1$ to $C_{10}$ alkyl, alkylamino, alkenyl, alkynyl, hydroxyalkyl, alkoxy, dialkylamino thioalkyl, thioalkenyl, thioalkynyl, aryloxy, acyloxy, thioacyl, amido, and sulphonamido, and wherein X is independently represent H, OH, $R_7$, $OR_7$, $NR_7R_8$, wherein $C_1$-$C_6$ alkyl, carboxy $C_1$-$C_6$ alkyl, dicarboxy $C_1$-$C_6$ alkyl, aryl, heteroaryl, alkenyl, alkynyl, hydroxyalkyl, alkoxy, dialkylamino thioalkyl, thioalkenyl, thioalkynyl, aryloxy, acyloxy, thioacyl, amido, and sulphonamido; and treating or preventing cancer in the subject. The compound of formula V, may have the formula:

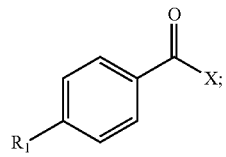

(VII)

wherein $R_1$ is OH, and wherein X is independently represent H, OH, $R_7$, $OR_7$, $NR_7R_8$, wherein $C_1$-$C_6$ alkyl, carboxy $C_1$-$C_6$ alkyl, dicarboxy $C_1$-$C_6$ alkyl, aryl, heteroaryl, alkenyl, alkynyl, hydroxyalkyl, alkoxy, dialkylamino thioalkyl, thioalkenyl, thioalkynyl, aryloxy, acyloxy, thioacyl, amido, and sulphonamido.

Another embodiment of the present invention is a method of treating or preventing cancer in a subject comprising the steps of administering to a subject having or at risk for cancer a pharmaceutical composition. The pharmaceutical composition comprises an agent selected from the group comprising a salt, solvate, or stereoisomer of compound (VIII) or its derivatives or a mixture of their constituents, where the compound has the formula:

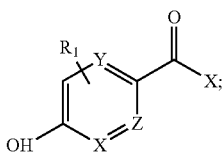

(VIII)

wherein X, Y, and Z can independently be N or C, with the proviso that X, Y, and Z cannot all be N, and wherein $R_1$ is H, OH, Halo, cyano, nitro, $C_1$-$C_6$ alkyl, carboxy $C_1$-$C_6$ alkyl, dicarboxy $C_1$-$C_6$ alkyl, $NR_2R_3$, wherein $R_2$ and $R_3$ are independently represent hydroxy, $C_1$ to $C_{10}$ alkyl, alkylamino, alkenyl, alkynyl, hydroxyalkyl, alkoxy, dialkylamino thioalkyl, thioalkenyl, thioalkynyl, aryloxy, acyloxy, thioacyl, amido, and sulphonamido, and wherein X is independently represent H, OH, $R_7$, $OR_7$, $NR_7R_8$, wherein $C_1$-$C_6$ alkyl, carboxy $C_1$-$C_6$ alkyl, dicarboxy $C_1$-$C_6$ alkyl, aryl, heteroaryl, alkenyl, alkynyl, hydroxyalkyl, alkoxy, dialkylamino thioalkyl, thioalkenyl, thioalkynyl, aryloxy, acyloxy, thioacyl, amido, and sulphonamido; and treating or preventing cancer in the subject.

Another embodiment of the present invention is an in vivo, large-scale and high-throughput screening method for identifying cell mechanical modulator, the screening method comprising the steps of: (a) obtaining cells and placing the cells on multiple-well substrate plates for cytokinesis; (b) contacting the cells on multiple-well substrate plates with compound candidates; and (c) monitoring and analyzing the cytokinesis and the growth of the cells. Suitable cells used in the screening methods of the present invention include those from Dictyostelium discoideum strains, both wild type and mutants. The screening methods of the present invention are capable of identifying cell mechanical modulators.

BRIEF DESCRIPTION OF THE DRAWINGS

FIG. 2(A-D) are a set of images and graphs showing the molecular structure of carbamate-7 and identification of carbamate-7 as a cytokinesis inhibitor affecting the myosin II-RacE pathway according to one embodiment of the present invention.

FIG. 4(A-G) are a set of images and graphs showing that 4-hydroxyacetophenone activates myosin II.

FIG. 5A: TIRF images of GFP-myosin II, GFP-3XAsp, and GFP-3XAla expressing myoI null cell-lines in DMSO compared to 10 min 500 nM 4-HAP treatment show an increase in BTFs across all three cell-lines. FIG. 5B shows quantification of 4-HAP time-course. GFP-S1 and GFP-S456L expressing cell-lines showed no changes over untreated samples FIG. 5A over the time-course of the experiment (FIG. 5B, right panel).

FIGS. 9(B-D): Plate type affects screening quality. Primary pilot screening was performed on COP plates (FIG. 9D), which showed a tighter distribution of multinucleate cells to mononucleate cells, as well as a tighter distribution of binucleate cells to mononucleate cells as compared to 96-well (FIG. 9B) and 384-well (FIG. 9C) Corning plates. The tighter distribution of untreated WT wells allowed for cytokinesis hits to be more readily identified in the following process: acquisition of (FIG. 9E) raw images of NLS-tdTomato expressing cells and conversion into (FIG. 9F) CIMPAQ-processed version. In both, the white box represents a zoomed quadrant, highlighting both the nuclear and cellular boundaries of a multinucleate (4 nuclei/cell) and several mononucleate cells.

FIGS. 10(D-E): CIMPAQ uses a threshold value for nuclear area to identify mitotic inhibitors.

FIG. 11(A-D) are figures and graphs showing characterization of carbamate-7 degradation.

FIG. 12(A-B) are a set of graphs showing reversibility of 4-HAP effect on myosin II cortical enrichment.

FIG. 13(A-B) are a set of graphs showing quantification of TIRF images which show an increase in myosin II localization in 4-HAP treated cells, independent of area changes. FIG. 13A: Dot plots of the raw data showing the fold-increase over the DMSO control at 7 min of 500 nM 4-HAP treatment, but not in a similar DMSO time course, 500 nM 3,4-DCA time course, or 500 nM 1,3-bis-(3,4-dichloro-phenyl)-urea time course. FIG. 13B: Dot plots of the raw data of the cell-surface contact area shows no change between time points for all compound treatments.

FIGS. 15(E-F): Quantification of TIRF images reveals no myosin II localization change in 4-HAP treated cortI::GFPmyo cells. FIG. 15(G-H): 4-HAP affects wild type and metastatic pancreatic cells in a myosin II-specific manner.

FIG. 23(A-C) Scoring analysis and differential expression patterns of mechanoresponsive and non-mechanoresponsive paralogs in patient-derived IHC data. (A) Schematic of scoring analysis of ducts from IHC data. Each analyzed duct is assigned an intensity/area value. Ducts with no staining are assigned 0/0, ducts with low intensity in less than 50% of the surface area of the duct are assigned a 1/1, ducts with low intensity staining in over 50% of the duct are given 1/2, ducts with high intensity staining in less than 50% of their surface area are assigned a 2/1, and those with high intensity in more than 50% of the duct are given a 2/2. These numbers are converted to an assigned value of 1, 2, 3, 4, and 5 respectively to be quantitatively assessed. The sample images shown below for each assigned value are from a single patient and stained with myosin IIC antibody. (B) Sample from a duct with PanIN progression shows similar pattern of expression across all stained proteins. Insets of normal (N), panIN (P), and cancerous (C) sections of the duct are presented. (FIG. 23C) Gene Expression Omnibus (GEO) data roughly correlates with the IHC data showing the upregulation of mechanoresponsive proteins of the PDAC mechanobiome. Normal (N) samples are compared to tumor samples (T) as normalized values to the average of the normal set within each gene. Medians are provided; *p<0.02, p<0.001, *p<0.0001.

FIG. 26(A-C) Method for quantifying actin structures at the cellular cortex. (26A) Sample spheroid illustrating the workflow to achieve the final linearized cortex used for quantifications. After background subtraction (i), the edge of the spheroid was traced (ii). Normal lines were drawn from each pixel on the border (iii) to generate a linearized version of the cortex. This image was then cropped and binarized. A Hough Transform was performed on the binarized image to detect lines representing the fluorescently labeled actin bands. (26B) From the Hough Transform we calculated a continuity score. The score is calculated by summing the lengths of the Hough lines and dividing by the number of individual Hough bands added to the length of the image. A high score indicates a more continuous actin band. The score for the control spheroids decreased upon treatment with 4-HAP, indicating an altered actin distribution upon 4-HAP treatment. The myo IIA knockdowns (shIIA) had the lowest score signifying the least continuous actin bands. Upon 4-HAP treatment, the continuity score for the shIIA cells increased significantly (p=0.01), indicating an increase in band continuity. The myo IIC (shIIC) knockdowns had a high score indicating a high degree of continuity, but were not affected by 4-HAP treatment indicating that 4-HAP requires myosin IIC for its action. (26C) From the binarized cortex, additional metrics can be used to describe the cytoskeletal structure including cortex coverage defined by (number of white pixels/total number of pixels). Higher cortex coverage is roughly proportional to how much of the cortex is covered by actin bands and how thick these bands are. Control spheroids treated with 4-HAP had decreased cortex coverage, indicating an altered actin distribution. The myo IIA knockdowns had the lowest actin band coverage, but when treated with 4-HAP, the coverage increased. The myo IIC knockdowns were unaffected by the treatment of 4-HAP, but had significantly higher actin band coverage compared to the myo IIA untreated knockdowns.

DETAILED DESCRIPTION OF THE INVENTION

I. In General

Figure 1A:
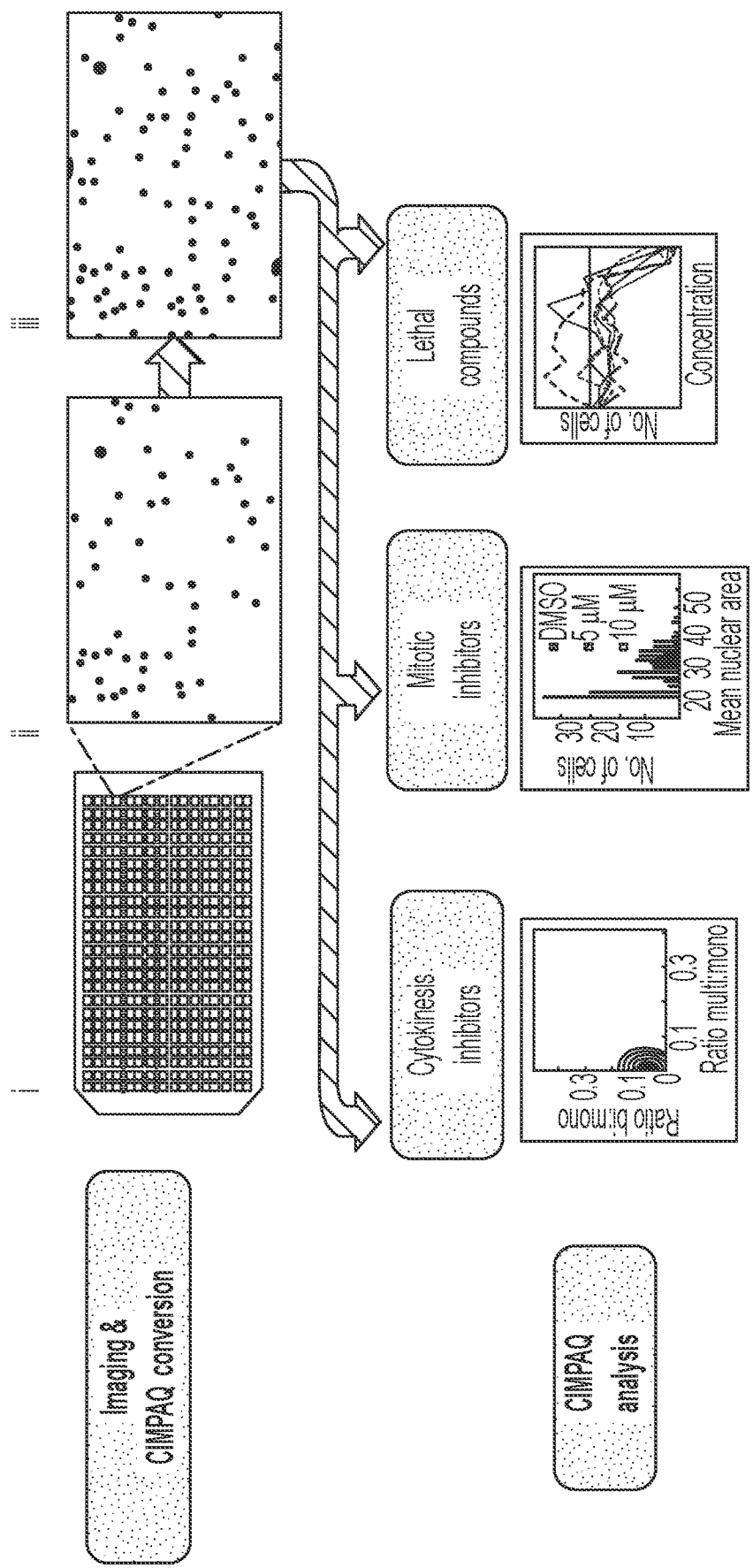
FIG. 1A shows workflow diagram of primary screening from 384-well plating (i) to raw data acquisition (ii) to CIMPAQ image conversion by segmentation (iii). Cytokinesis hits are identified in a 5-step process: Acquisition of FIG. 1A(ii) raw images of NLS-tdTomato expressing cells and are converted into FIG. 1A(iii) CIMPAQ-processed version.

Before the present materials and methods are described, it is understood that this invention is not limited to the particular methodology, protocols, materials, and reagents described, as these may vary. It is also to be understood that the terminology used herein is for the purpose of describing particular embodiments only, and is not intended to limit the scope of the present invention which will be limited only by any later-filed nonprovisional applications.

It must be noted that as used herein and in the appended claims, the singular forms "a", "an", and "the" include plural reference unless the context clearly dictates otherwise. As well, the terms "a" (or "an"), "one or more" and "at least one" can be used interchangeably herein. The terms "comprising" and variations thereof do not have a limiting meaning where these terms appear in the description and claims. Accordingly, the terms "comprising", "including", and "having" can be used interchangeably.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods and materials are now described. All publications and patents specifically mentioned herein are incorporated by reference for all purposes including describing and disclosing the chemicals, instruments, statistical analysis and methodologies which are reported in the publications which might be used in connection with the invention. All references cited in this specification are to be taken as indicative of the level of skill in the art. Nothing herein is to be construed as an admission that the invention is not entitled to antedate such disclosure by virtue of prior invention.

The terminology as set forth herein is for description of the embodiments only and should not be construed as limiting of the invention as a whole.

As used herein, the term "subject" or "individual" refers to a human or other vertebrate animal. It is intended that the term encompass "patients."

The term "pharmaceutically acceptable" as used herein means that the compound or composition or carrier is suitable for administration to a subject to achieve the treatments described herein, without unduly deleterious side effects in light of the necessity of the treatment.

The term "therapeutically effective amount" or "pharmaceutically appropriate dosage", as used herein, refers to the amount of the compounds or dosages that will elicit the biological or medical response of a subject, tissue or cell that is being sought by the researcher, veterinarian, medical doctor or other clinician.

As used herein, "pharmaceutically-acceptable carrier" includes any and all dry powder, solvents, dispersion media, coatings, antibacterial and antifungal agents, isotonic agents, absorption delaying agents, and the like. Pharmaceutically-acceptable carriers are materials, useful for the purpose of administering the compounds in the method of the present invention, which are preferably non-toxic, and may be solid, liquid, or gaseous materials, which are otherwise inert and pharmaceutically acceptable, and are compatible with the compounds of the present invention. Examples of such carriers include, various lactose, mannitol, oils such as corn oil, buffers such as PBS, saline, polyethylene glycol, glycerin, polypropylene glycol, dimethylsulfoxide, an amide such as dimethylacetamide, a protein such as albumin, and a detergent such as Tween 80, mono- and oligopolysaccharides such as glucose, lactose, cyclodextrins and starch.

The term "administering" or "administration", as used herein, refers to providing the compound or pharmaceutical composition of the invention to a subject suffering from or at risk of the diseases or conditions to be treated or prevented.

The term "systemic delivery", as used herein, refers to any suitable administration methods which may delivery the compounds in the present invention systemically. In one embodiment, systemic delivery may be selected from the group consisting of oral, parenteral, intranasal, inhaler, sublingual, rectal, and transdermal administrations.

A route of administration in pharmacology and toxicology is the path by which a drug, fluid, poison, or other substance is taken into the body. Routes of administration may be generally classified by the location at which the substance is applied. Common examples may include oral and intravenous administration. Routes can also be classified based on where the target of action is. Action may be topical (local), enteral (system-wide effect, but delivered through the gastrointestinal tract), or parenteral (systemic action, but delivered by routes other than the GI tract), via lung by inhalation.

A topical administration emphasizes local effect, and substance is applied directly where its action is desired. Sometimes, however, the term topical may be defined as applied to a localized area of the body or to the surface of a body part, without necessarily involving target effect of the substance, making the classification rather a variant of the classification based on application location. In an enteral administration, the desired effect is systemic (non-local), substance is given via the digestive tract. In a parenteral administration, the desired effect is systemic, and substance is given by routes other than the digestive tract.

The examples for topical administrations may include epicutaneous (application onto the skin), e.g., allergy testing or typical local anesthesia, inhalational, e.g. asthma medications, enema, e.g., contrast media for imaging of the bowel, eye drops (onto the conjunctiva), e.g., antibiotics for conjunctivitis, ear drops, such as antibiotics and corticosteroids for otitis externa, and those through mucous membranes in the body.

Enteral administration may be administration that involves any part of the gastrointestinal tract and has systemic effects. The examples may include those by mouth (orally), many drugs as tablets, capsules, or drops, those by gastric feeding tube, duodenal feeding tube, or gastrostomy, many drugs and enteral nutrition, and those rectally, various drugs in suppository.

The examples for parenteral administrations may include intravenous (into a vein), e.g. many drugs, total parenteral nutrition intra-arterial (into an artery), e.g., vasodilator drugs in the treatment of vasospasm and thrombolytic drugs for treatment of embolism, intraosseous infusion (into the bone marrow), intra-muscular, intracerebral (into the brain parenchyma), intracerebroventricular (into cerebral ventricular system), intrathecal (an injection into the spinal canal), and subcutaneous (under the skin). Among them, intraosseous infusion is, in effect, an indirect intravenous access because the bone marrow drains directly into the venous system. Intraosseous infusion may be occasionally used for drugs and fluids in emergency medicine and pediatrics when intravenous access is difficult.

Any route of administration may be suitable for the present invention. In one embodiment, the compound of the present invention may be administered to the subject via intravenous injection. In another embodiment, the compounds of the present invention may be administered to the subject via any other suitable systemic deliveries, such as oral, parenteral, intranasal, sublingual, rectal, or transdermal administrations.

In another embodiment, the compounds of the present invention may be administered to the subject via nasal systems or mouth through, e.g., inhalation.

In another embodiment, the compounds of the present invention may be administered to the subject via intraperitoneal injection or IP injection.

As used herein, the term "intraperitoneal injection" or "IP injection" refers to the injection of a substance into the peritoneum (body cavity). IP injection is more often applied to animals than to humans. In general, IP injection may be preferred when large amounts of blood replacement fluids are needed, or when low blood pressure or other problems prevent the use of a suitable blood vessel for intravenous injection.

In animals, IP injection is used predominantly in veterinary medicine and animal testing for the administration of systemic drugs and fluids due to the ease of administration compared with other parenteral methods.

In humans, the method of IP injection is widely used to administer chemotherapy drugs to treat some cancers, in particular ovarian cancer. Although controversial, this specific use has been recommended as a standard of care.

As used herein, the term "Dictyostelium discoideum" refers to a species of soil-living amoeba belonging to the phylum Mycetozoa. Commonly referred to as cellular slime mold, *D. discoideum* is a eukaryote that transitions from a collection of unicellular amoebae into a multicellular slug and then into a fruiting body within its lifetime. *D. discoideum* has a unique asexual lifecycle that consists of four stages: vegetative, aggregation, migration, and culmination. The life cycle of *D. discoideum* is relatively short, which allows for timely viewing of all life stages. The cells involved in the life cycle undergo movement, chemical signaling, and development, which are applicable to human cancer research. The simplicity of its life cycle makes *D. discoideum* a valuable model organism to study genetic, cellular, and biochemical processes in other organisms. In the present invention, Applicants use Dictyostelium *discoideum* as a model for cytokinesis. This simple protozoan performs cytokinesis and cell motility in a manner similar to human cells yet it is tractable for genetic, molecular, biochemical, and biophysical methods.

As used herein, the term "cytokinesis" refers to the process in which the cytoplasm of a single eukaryotic cell is divided to form two daughter cells. It usually initiates during the early stages of mitosis, and sometimes meiosis, splitting a mitotic cell in two, to ensure that chromosome number is maintained from one generation to the next. After cytokinesis two (daughter) cells will be formed that enter interphase to make exact copies of the (parent) original cell. In one aspect of the invention, Applicants use cytokinesis as a highly mechanical cell-shape change process to establish an in vivo, large-scale, high-throughput chemical screen for small molecule modulators of cell shape change.

As used herein, the term "myosin II", also known as conventional myosin, refers to the myosin type responsible for producing contraction, including in nonmuscle and muscle cells. Myosin II contains two heavy chains, each about 2000 amino acids in length, which constitute the head and tail domains. Each of these heavy chains contains the N-terminal head domain, while the C-terminal tails have a coiled-coil structure, which hold the two heavy chains together. Thus, myosin II has two heads. The intermediate neck domain is the region creating the angle between the head and tail. In nonmuscle cells, myosin II has three paralogs: myosin IIA (MYH9), myosin IIB (MYH10), and myosin IIC (MYH14). In smooth muscle, a single gene (MYH11) codes for the heavy chain of myosin II, but splice variants of this gene result in four distinct isoforms. Other myosin II paralogous proteins are found in cardiac and skeletal muscle.

Myosin II may also contain 4 light chains, resulting in 2 per head, weighing 20 ($MLC_{20}$) and 17 ($MLC_{17}$) kDa. These bind the heavy chains in the "neck" region between the head and tail. The $MLC_{20}$ is also known as the regulatory light chain and actively participates in muscle contraction. The $MLC_{17}$ is also known as the essential light chain. Its exact function is unclear, but is believed to contribute to the structural stability of the myosin, head along with $MLC_{20}$. Two variants of $MLC_{17}$ ($MLC_{17a/b}$) exist as a result of alternate splicing at the $MLC_{17}$ gene. In muscle cells, the long coiled-coil tails of the individual myosin molecules join together, forming the thick filaments of the sarcomere. The force-producing head domains stick out from the side of the thick filament, ready to walk along the adjacent actin-based thin filaments in response to the proper chemical signals.

As used herein, the term "cell mechanics" refers to a study of the structure and function of biological systems such as cells by means of the methods of mechanics.

As used herein, the term "mechanotransduction" refers to the process of sensing, transmitting, and converting physical forces into biochemical signals and integrating these signals into the cellular responses. Mechanotransduction generally refers to the many mechanisms by which cells convert mechanical stimulus into chemical activity. Mechanotransduction is responsible for a number of senses and physiological processes in the body, including proprioception, touch, balance, and hearing. At the cellular level, mechanotransduction is responsible for guiding processes such as cellular decision making, cell differentiation, and cell morphogenesis. The basic mechanism of mechanotransduction involves converting mechanical signals into electrical or chemical signals. For mechanochemical conversion, mechanical forces are transmitted through the plasma membrane through membrane-actin anchoring proteins and then propagated onto the cytoskeletal networks. Myosin II proteins along with other actin associated proteins are essential components of the mechanotransduction system. These proteins then can lead to the accumulation and/or activation of signaling molecules, including regulators of small GTPases and kinases, allowing for the mechanochemical conversion. For electrical signals, a mechanically gated ion channel makes it possible for sound, pressure, or movement to cause a change in the excitability of specialized sensory cells and sensory neurons. The stimulation of a mechanoreceptor causes mechanically sensitive ion channels to open and produce a transduction current that changes the membrane potential of the cell. Cellular responses to mechanotransduction are variable and give rise to a variety of changes and sensations that extend from molecular to cellular to tissue to organ and organ system levels.

As used herein, the term "derivative" refers to a substance which comprises the same basic carbon skeleton and functionality as the parent compound, but can also bear one or more substituents or substitutions of the parent compound. The derivative may also include salts, solvates and prodrugs of compounds of the invention.

As used herein, the term "constituent" refers to a substance or a mixture of substances, which are produced during a biochemical or chemical reaction (e.g., decomposition) of another precursor compound. In one specific embodiment of the present invention, the precursor compound is compound (I) or its derivatives.

II. The Invention

In one embodiment, the present invention discloses small molecules which may be used as activators of myosin II. These small molecules may promote myosin II activity and accumulation through modulation of motor mechanochemistry, assembly and sub-cellular localization pathways. These small molecules may be used to modulate cell and tissue mechanics. This class of molecules, which activate the contractile system of the cell, may be used for therapeutic and tissue engineering applications.

In one embodiment of the present invention, one of the myosin II activators is 4-acetylphenyl-(3,4-dichlorophenyl) carbamate, also named carbamate-7 (C7) (Formula I).

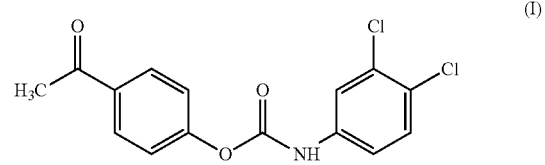 [SMILES: CC(=O)c1ccc(OC(=O)Nc2ccc(Cl)c(Cl)c2)cc1]

Example 2 shows that carbamate-7 may be used as a cytokinesis inhibitor affecting the myosin II—RacE pathway. The experimental results show that carbamate-7 may increase the fraction of binucleates at nM concentrations. Therefore, carbamate-7, or its derivatives or a mixture of their constituents may be used as a myosin II activator. Applicants' initial experiments on carbamate-7 suggested that it targets a key cytokinesis regulatory pathway.

In one embodiment, the present invention discloses a method for modulating cell mechanics of a disease condition in a subject comprising the step of administering an effective amount of a compound having the formula (I).

Any suitable administering method may be used in the present invention. In one embodiment, carbamate-7, or its derivatives or a mixture of their constituents may be administered by systemic delivery. In one specific embodiment, the method of administering by systemic delivery is selected from the group consisting of oral, parenteral, intranasal, sublingual, rectal, and transdermal administration.

In another embodiment, the present invention discloses a compound having formula I for use in activating myosin II to treat a disease condition in a subject by systemic delivery. Applicants envision that carbamate-7, or its derivatives or a mixture of their constituents, may be used in a combination of other known myosin II modulating compounds to modulate myosin II and activate it in the cell. Some of the exemplary myosin II modulating compounds may include Omecamtiv mecarbil (Cytokinetics, INC.), Blebbistatin, BDM, Calyculin A, Myosin light chain phosphorylation inhibitors including myosin light chain kinase (MLCK) inhibitors, such as ML-7, and Rho kinase (ROCK) inhibitors, such as Y-27632.

In one embodiment, the myosin II activator is 4-hydroxyacetophenone (4-HAP) (Formula II), or its derivatives or a mixture of their constituents.

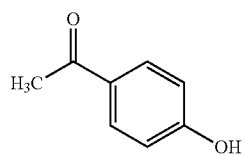

(II)

In one embodiment, the myosin II activator may include any compounds which can produce 4-HAP (Formula II) or its derivatives as one of the constituents upon decomposition of the compound.

Applicants' initial experiments (Example 4) show that carbamate-7 is unstable, which can degrade rapidly to form two major products, 4-hydroxyacetophenone (4-HAP) (Formula II) and 3,4-dichloroaniline (3,4-DCA) (Formula III).

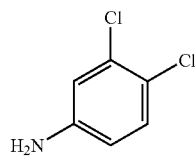

(III)

As shown in Examples 4 and 5, 4-HAP or its derivatives can increase the cortical localization of the mechanoenzyme myosin II, thereby increasing the cell's cortical tension. Activity of 4-HAP is independent of myosin heavy-chain phosphorylation, the primary regulator of bipolar thick-filament assembly. Furthermore, similar effects on myosin recruitment have been observed in mammalian cells, suggesting that 4-HAP or its derivatives may pharmacologically modify cell mechanics across phylogeny and disease states.

In one embodiment, the present invention discloses a method for modulating cell mechanics of a disease condition in a subject comprising the step of administering an effective amount of a compound having the formula (II).

Any suitable administering method may be used in the present invention. In one embodiment, 4-HAP or its derivatives may be administered by systemic delivery. In one specific embodiment, the method of administering by systemic delivery is selected from the group consisting of oral, parenteral, intranasal, sublingual, rectal, and transdermal administration.

In another embodiment, the present invention discloses a compound of 4-HAP or its derivatives having Formula II for use in activating myosin II to treat a disease condition in a subject by systemic delivery.

In one embodiment, the active compound of 4-HAP or its derivatives may be combined with other compounds for activating myosin II to treat a disease condition in a subject by systemic delivery.

For example, 3,4-dichloroaniline (3,4-DCA) by itself appears to have limited cellular effect. But, to have maximal cytokinesis inhibition, 3,4-DCA and 4-HAP or its derivatives work additively. Thus, 4-HAP or its derivatives may be used by itself or in combination with 3,4-DCA to differentially modulate cell division.

In one embodiment, Applicants envision that 4-HAP or its derivatives may be used in a combination with any other myosin II modulating compounds to modulate myosin II and activate it in the cell. 4-HAP or its derivatives may also be used with any other known myosin II modulating compounds. Some of the exemplary myosin II modulating compound may include Omecamtiv mecarbil (Cytokinetics, INC.), Blebbistatin, BDM, Calyculin A, Myosin light chain phosphorylation inhibitors including myosin light chain kinase (MLCK) inhibitors, such as ML-7, and Rho kinase (ROCK) inhibitors, such as Y-27632. Applicants envision that 4-HAP may be used in combination with other compounds that target other aspects of cell signaling, membrane receptors, ion channels, any of which target other cell and tissue related behaviors, including, but not limited to, cell growth, motility, migration, and invasion.

In one embodiment, the present invention discloses a method for modulating cell mechanics of a disease condition in a subject comprising administering by systemic delivery effective amounts of compounds 4-HAP or its derivatives and 3,4-DCA having the formula (II) and formula (III), respectively. In one embodiment, both compounds 4-HAP and 3,4-DCA may be administered at the same time. Effective amounts of compounds 4-HAP and 3,4-DCA may be initially mixed. The mixture may subsequently be administered by any suitable systemic delivery methods. In another embodiment, effective amounts of compounds 4-HAP or its derivatives and 3,4-DCA may be individually administered by any suitable systemic delivery methods.

In one embodiment, the present invention also discloses other small molecule compounds which may be used as myosin II activators and/or and cytokinesis modulators. Using the Dictyostelium Drug Discovery Platform (3DP), Applicants have identified other small molecule compounds as cytokinesis modulators. For example, 4-phenyl-2-butanone (4-nitrophenyl) hydrazone (Formula IV), may also inhibit cell division but through a different pathway from those of 4-HAP. A genetic selection for suppressors of 4-phenyl-2-butanone (4-nitrophenyl) hydrazone inhibition identified ATP synthase β-subunit as a genetic suppressor, which is particularly interesting as angiostatins are known to target $F_1F_0$ ATP synthase.

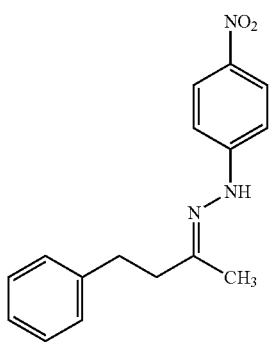

(IV)

In one embodiment, the present invention disclose a method for modulating cell mechanics of a disease condition in a subject comprising the step of administering by systemic delivery an effective amount of a compound having the formula (IV).

Any suitable administering method may be used in the present invention. In one embodiment, 4-phenyl-2-butanone (4-nitrophenyl) hydrazone may be administered by systemic delivery. In one specific embodiment, the method of administering by systemic delivery is selected from the group consisting of oral, parenteral, intranasal, sublingual, rectal, and transdermal administration.

In one embodiment, Applicants envision that 4-phenyl-2-butanone (4-nitrophenyl) hydrazone may be used in a combination with any other myosin II modulating compounds to modulate myosin II and activate it in the cell. For example, 4-phenyl-2-butanone (4-nitrophenyl) hydrazone may be combined with carbamate-7, or its derivatives or a mixture of their constituents, or 4-HAP or its derivatives as discussed above to modulate myosin II and activate it in the cell. 4-phenyl-2-butanone (4-nitrophenyl) hydrazone may also be used with any other known myosin II modulating compounds. Some of the exemplary myosin II modulating compound may include Omecamtiv mecarbil (Cytokinetics, INC.), Blebbistatin, BDM, Calyculin A, Myosin light chain phosphorylation inhibitors including myosin light chain kinase (MLCK) inhibitors, such as ML-7, and Rho kinase (ROCK) inhibitors, such as Y-27632.

The present invention also encloses pharmaceutical compositions comprising one or more active compounds of this invention in association with a pharmaceutically acceptable carrier. Preferably these compositions are in unit dosage forms such as tablets, pills, capsules, powders, granules, sterile parenteral solutions or suspensions, metered aerosol or liquid sprays, drops, ampoules, auto-injector devices or suppositories; for oral, parenteral, intranasal, sublingual or rectal administration, or for administration by inhalation or insufflation. It is also envisioned that the compounds of the present invention may be incorporated into transdermal patches designed to deliver the appropriate amount of the drug in a continuous fashion.

For preparing solid compositions such as tablets, the principal active ingredient is mixed with a pharmaceutically acceptable carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture for a compound of the present invention, or a pharmaceutically acceptable salt thereof. When referring to these preformulation compositions as homogeneous, it is meant that the active ingredient is dispersed evenly throughout the composition so that the composition may be easily subdivided into equally effective unit dosage forms such as tablets, pills and capsules. The tablets or pills of the novel composition can be coated or otherwise compounded to provide a dosage affording the advantage of prolonged action. For example, the tablet or pill can comprise an inner dosage and an outer dosage component, the latter being in the form of an envelope over the former. The two components can be separated by an enteric layer which, serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, suitably flavored syrups, aqueous or oil suspensions, and flavored emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone or gelatin.

The compounds of the present invention are particularly useful when formulated in the form of a pharmaceutical injectable dosage, including a compound described and claimed herein in combination with an injectable carrier system. As used herein, injectable and infusion dosage forms (i.e., parenteral dosage forms) include, but are not limited to, liposomal injectables or a lipid bilayer vesicle having phospholipids that encapsulate an active drug substance. Injection includes a sterile preparation intended for parenteral use.

Five distinct classes of injections exist as defined by the USP: emulsions, lipids, powders, solutions and suspensions. Emulsion injection includes an emulsion comprising a sterile, pyrogen-free preparation intended to be administered parenterally. Lipid complex and powder for solution injection are sterile preparations intended for reconstitution to form a solution for parenteral use. Powder for suspension injection is a sterile preparation intended for reconstitution to form a suspension for parenteral use. Powder lyophilized for liposomal suspension injection is a sterile freeze dried preparation intended for reconstitution for parenteral use that is formulated in a manner allowing incorporation of liposomes, such as a lipid bilayer vesicle having phospholipids used to encapsulate an active drug substance within a lipid bilayer or in an aqueous space, whereby the formulation may be formed upon reconstitution. Powder lyophilized for solution injection is a dosage form intended for the solution prepared by lyophilization ("freeze drying"), whereby the process involves removing water from products in a frozen state at extremely low pressures, and whereby subsequent addition of liquid creates a solution that conforms in all respects to the requirements for injections. Powder lyophilized for suspension injection is a liquid preparation intended for parenteral use that contains solids suspended in a suitable fluid medium, and it conforms in all respects to the requirements for Sterile Suspensions, whereby the medicinal agents intended for the suspension are prepared by lyophilization. Solution injection involves a liquid preparation containing one or more drug substances dissolved in a suitable solvent or mixture of mutually miscible solvents that is suitable for injection.

Solution concentrate injection involves a sterile preparation for parenteral use that, upon addition of suitable solvents, yields a solution conforming in all respects to the requirements for injections. Suspension injection involves a liquid preparation (suitable for injection) containing solid particles dispersed throughout a liquid phase, whereby the particles are insoluble, and whereby an oil phase is dispersed throughout an aqueous phase or vice-versa. Suspension liposomal injection is a liquid preparation (suitable for injection) having an oil phase dispersed throughout an aqueous phase in such a manner that liposomes (a lipid bilayer vesicle usually containing phospholipids used to encapsulate an active drug substance either within a lipid bilayer or in an aqueous space) are formed. Suspension sonicated injection is a liquid preparation (suitable for injection) containing solid particles dispersed throughout a liquid phase, whereby the particles are insoluble. In addition, the product may be sonicated as a gas is bubbled through the suspension resulting in the formation of microspheres by the solid particles.

The parenteral carrier system includes one or more pharmaceutically suitable excipients, such as solvents and co-solvents, solubilizing agents, wetting agents, suspending agents, thickening agents, emulsifying agents, chelating agents, buffers, pH adjusters, antioxidants, reducing agents, antimicrobial preservatives, bulking agents, protectants, tonicity adjusters, and special additives.

Therapeutic Methods

Combinations of the compounds described above may be administered to a subject in a single dosage form or by separate administration of each active agent. The agents may be formulated into a single tablet, pill, capsule, or solution for parenteral administration and the like. Individual therapeutic agents may be isolated from other therapeutic agent(s) in a single dosage form. Formulating the dosage forms in such a way may assist in maintaining the structural integrity of potentially reactive therapeutic agents until they are administered. Therapeutic agents may be contained in segregated regions or distinct caplets or the like housed within a capsule. Therapeutic agents may also be provided in isolated layers in a tablet.

Alternatively, the therapeutic agents may be administered as separate compositions, e.g., as separate tablets or solutions. One or more active agent may be administered at the same time as the other active agent(s) or the active agents may be administered intermittently. The length of time between administrations of the therapeutic agents may be adjusted to achieve the desired therapeutic effect. In certain instances, one or more therapeutic agent(s) may be administered only a few minutes (e.g., about 1, 2, 5, 10, 30, or 60 min) after administration of the other therapeutic agent(s). Alternatively, one or more therapeutic agent(s) may be administered several hours (e.g., about 2, 4, 6, 10, 12, 24, or 36 h) after administration of the other therapeutic agent(s). In certain embodiments, it may be advantageous to administer more than one dosage of one or more therapeutic agent(s) between administrations of the remaining therapeutic agent(s). For example, one therapeutic agent may be administered at 2 hours and then again at 10 hours following administration of the other therapeutic agent(s). The therapeutic effects of each active ingredient should overlap for at least a portion of the duration, so that the overall therapeutic effect of the combination therapy is attributable in part to the combined or synergistic effects of the combination therapy.

The dosage of the active agents will generally be dependent upon a number of factors including pharmacodynamic characteristics of each agent of the combination, mode and route of administration of active agent(s), the health of the patient being treated, the extent of treatment desired, the nature and kind of concurrent therapy, if any, and the frequency of treatment and the nature of the effect desired. In general, dosage ranges of the active agents often range from about 0.001 to about 250 mg/kg body weight per day. However, some variability in this general dosage range may be required depending upon the age and weight of the subject being treated, the intended route of administration, the particular agent being administered and the like. Since two or more different active agents are being used together in a combination therapy, the potency of each agent and the interactive effects achieved using them together must be considered. Importantly, the determination of dosage ranges and optimal dosages for a particular mammal is also well within the ability of one of ordinary skill in the art having the benefit of the instant disclosure.

Dosage ranges for agents may be as low as 5 ng/d. In certain embodiments, about 10 ng/day, about 15 ng/day, about 20 ng/day, about 25 ng/day, about 30 ng/day, about 35 ng/day, about 40 ng/day, about 45 ng/day, about 50 ng/day, about 60 ng/day, about 70 ng/d, about 80 ng/day, about 90 ng/day, about 100 ng/day, about 200 ng/day, about 300 ng/day, about 400 ng/day, about 500 ng/day, about 600 ng/day, about 700 ng/day, about 800 ng/day, about 900 ng/day, about 1 µg/day, about 2 µg/day, about 3 µg/day, about 4 µg/day, about 5 µg/day, about 10 µg/day, about 15 µg/day, about 20 µg/day, about 30 µg/day, about 40 µg/day, about 50 µg/day, about 60 µg/day, about 70 µg/day, about 80 µg/day, about 90 µg/day, about 100 µg/day, about 200 µg/day, about 300 µg/day, about 400 µg/day, about 500 µg/day, about 600 µg/day, about 700 µg/day, about 800 µg/day, about 900 µg/day, about 1 mg/day, about 2 mg/day, about 3 mg/day, about 4 mg/day, about 5 mg/day, about 10 mg/day, about 15 mg/day, about 20 mg/day, about 30 mg/day, about 40 mg/day, or about 50 mg/day of an agent of the invention is administered.

In certain embodiments, the agents of the invention are administered in pM or nM concentrations. In certain embodiments, the agents are administered in about 1 pM, about 2 pM, about 3 pM, about 4 pM, about 5 pM, about 6 pM, about 7 pM, about 8 pM, about 9 pM, about 10 pM, about 20 pM, about 30 pM, about 40 pM, about 50 pM, about 60 pM, about 70 pM, about 80 pM, about 90 pM, about 100 pM, about 200 pM, about 300 pM, about 400 pM, about 500 pM, about 600 pM, about 700 pM, about 800 pM, about 900 pM, about 1 nM, about 2 nM, about 3 nM, about 4 nM, about 5 nM, about 6 nM, about 7 nM, about 8 nM, about 9 nM, about 10 nM, about 20 nM, about 30 nM, about 40 nM, about 50 nM, about 60 nM, about 70 nM, about 80 nM, about 90 nM, about 100 nM, about 200 nM, about 300 nM, about 400 nM, about 500 nM, about 600 nM, about 700 nM, about 800 nM, or about 900 nM concentrations. A dosage range of the present compounds for administration to animals, including humans, is from about 0.001 nM to about 500 mM. A preferred dosage range is 0.1 nM to 100 µM. A more preferred dosage range is 1 nM to 10 µM. The most preferred dosage range is 1 nM to 1 µM.

It may be advantageous for the pharmaceutical combination to be comprised of a relatively large amount of the first component compared to the second component. In certain instances, the ratio of the first active agent to second active agent is about 200:1, 190:1, 180:1, 170:1, 160:1, 150:1, 140:1, 130:1, 120:1, 110:1, 100:1, 90:1, 80:1, 70:1, 60:1, 50:1, 40:1, 30:1, 20:1, 15:1, 10:1, 9:1, 8:1, 7:1, 6:1, or 5:1. It further may be preferable to have a more equal distribution of pharmaceutical agents. In certain instances, the ratio of the first active agent to the second active agent is about 4:1, 3:1, 2:1, 1:1, 1:2, 1:3, or 1:4. It also may be advantageous for the pharmaceutical combination to have a relatively large amount of the second component compared to the first component. In certain instances, the ratio of the second active agent to the first active agent is about 30:1, 20:1, 15:1, 10:1, 9:1, 8:1, 7:1, 6:1, or 5:1. In certain instances, the ratio of the second active agent to first active agent is about 100:1, 90:1, 80:1, 70:1, 60:1, 50:1, or 40:1. In certain instances, the ratio of the second active agent to first active agent is about 200:1, 190:1, 180:1, 170:1, 160:1, 150:1, 140:1, 130:1, 120:1, or 110:1. A composition comprising any of the above-identified combinations of first therapeutic agent and second therapeutic agent may be administered in divided doses about 1, 2, 3, 4, 5, 6, or more times per day or in a form that will provide a rate of release effective to attain the desired results. The dosage form may contain both the first and second active agents. The dosage form may be administered one time per day if it contains both the first and second active agents.

For example, a formulation intended for oral administration to humans may contain from about 0.1 mg to about 5 g of the first therapeutic agent and about 0.1 mg to about 5 g of the second therapeutic agent, both of which are compounded with an appropriate and convenient amount of carrier material varying from about 5 to about 95 percent of the total composition. Unit dosages will generally contain between about 0.5 mg to about 1500 mg of the first therapeutic agent and 0.5 mg to about 1500 mg of the second therapeutic agent. The dosage may be about 25 mg, 50 mg, 100 mg, 200 mg, 300 mg, 400 mg, 500 mg, 600 mg, 800 mg, or 1000 mg, etc., up to about 1500 mg of the first therapeutic agent. The dosage may be about 25 mg, 50 mg, 100 mg, 200 mg, 300 mg, 400 mg, 500 mg, 600 mg, 800 mg, or 1 000 mg, etc., up to about 1500 mg of the second therapeutic agent.

The small molecule compounds, e.g., carbamate-7, 4-hydroxyacetophenone, and 4-phenyl-2-butanone (4-nitrophenyl) hydrazone, are useful to develop drugs that modulate myosin II, activating it in the cell, or modulating cytokinesis, perhaps through the ATP synthase β-subunit. Such compounds will have anti-cancer and/or anti-metastatic potential, be used to guide stem cell differentiation, and/or have therapeutic potential for a host of degenerative diseases such as motor neuron disease.

In one aspect, the present invention discloses an in vivo, large-scale and high-throughput method of screening by targeting cell mechanics to discover novel therapeutics for treating a disease condition related to cell mechanics defects. Applicants appreciate that in a disease condition such as a cancer, altered cell mechanics are a hallmark of metastatic efficiency. Applicants envision that one therapeutic approach is to increase cellular elasticity, which would in turn reduce metastatic potential and act downstream of cancer-inducing genetic alterations. Such chemical modulators will be powerful for a host of other applications of cell and tissue engineering. Additionally, modifications of the described compounds that may be caged and then uncaged in cells may be useful for directing the compounds to particular cells. Such applications might be useful for creating cells within a population that have differential mechanics or alternatively, homogenizing the mechanics of cells within the population.

The screening technology also can be adapted to a host of available mutant cell lines, which can increase the diversity of modulators that may be identified. Further as *D. discoideum* is an entire organism, this removes the ambiguity of how human cell-lines vary from the normal primary cells and how they become highly divergent between laboratory stocks.

Finally, the screening approach may be used to identify small molecule protectors of cell viability for the protection against toxic chemical agents. For example, one embodiment would be to screen for chemical protectors of smoke, such as from cigarettes, which is the leading cause of chronic obstructive pulmonary disease, the third leading cause of death in the U.S.

Applicants designed a live-cell, high-throughput chemical screen to identify mechanical modulators. Specifically, Applicants use cytokinesis as an evolutionarily conserved, highly mechanical cell-shape change platform to establish an in vivo, large-scale, high-throughput chemical screen for small molecule modulators of cell shape change.

In one embodiment, the present screen method searches for compounds that would provide a correcting function rather than simply killing cells (i.e., do no harm by minimizing side effects). In one embodiment, the present screen method identifies chemicals as highly potent, subtle modulators, rather than those that would completely abolish cell division.

In one embodiment, the present screen method analyzes and identifies compounds on the basis of their cytokinesis inhibitory activity, mitotic inhibitory activity, or lethality. Specifically, the present screen method identifies small molecules as novel cytokinesis inhibitors, mitotic inhibitors, and lethal compounds.

In one embodiment, the screening method comprises the steps of: (a) obtaining cells and place the cells on multiple-well substrate plates for cytokinesis; (b) contacting the cells on multi-well substrate plates with compound candidates; and (c) monitoring and analyzing the cytokinesis of the cells.

Any cell types suitable for analyzing cytokinesis as appreciated by one skilled in the art can be used in the present invention. In one specific embodiment, the cell type may be *Dictyostelium discoideum* strains. The cells may be placed on a multi-well substrate plate. In one embodiment, a polymer substrate plate with multi-wells may be used. Specifically, multi-well Cyclo Olegin Polymer (COP) plates are used for their optical characteristics that generated a tighter distribution of nuclei/cell counts.

In one preferred embodiment, the cells may be engineered to include nuclear reporters. In one specific embodiment, the nuclear reporters may include NLS-tdTomato which is optimal for live cell imaging in normal growth media over multiple time points, and that allows for the number of nuclei in each cell and nuclear area to be discerned.

The cells on the substrate plate may be contacted with compound candidates. In one specific embodiment, the present screen method is designed to test a large amount of compound candidates. For example, over 22,000 compounds from the ChemBridge Divert-SET library were screened.

The cytokinesis and growth of the cells may then be monitored and analyzed. In one embodiment, the cytokinesis and growth of the cells may then be monitored and analyzed by an imaging technique. A suitable imaging technique may include fluorescence, Raman, UV-Vis, IR or any other imaging technique appreciated by one skilled in the art. In one specific embodiment, the imaging technique is TIRF imaging. In one embodiment, the imaging technique is a confocal imaging technique. In one embodiment, the imaging technique uses a high content imager.

Specifically, Applicants developed a processing and analysis platform called Cytokinesis Image Processing Analysis Quantification (CIMPAQ), to maximize data collection from a single screen and to perform in-house data analysis. In one embodiment, by using CIMPAQ, one can analyze high content imaging data to identify cell viability, and cytokinetic and mitotic defects of Dictyostelium cells. By respectively counting cells, one can further determine the number of nuclei per cell, and measure the nuclear size of the cells. The Examples show the detail of the platform of CIMPAQ and methods of using such a platform. In the original embodiment of CIMPAQ, the program uses a single reporter—NLS-tdTomato—to track the nuclei and cytoplasmic volumes by using watershed to identify the different cell compartments. CIMPAQ can be readily adapted to other reporters that mark structures and organelles at the plasma membrane or cytoplasm in addition to the nucleus for further assay development.

In one embodiment, cytokinesis properties of the cells such as the binucleate to mononucleate ratio, and the multinucleate to mononucleate ratio may be used to determine cytokinesis inhibition of the corresponding compound candidates. For example, an increase in the binucleate to mononucleate ratio, and an increase of the multinucleate to mononucleate ratio may both indicate mild cytokinesis inhibition of the corresponding compounds.

The Examples shows the detail of this method and the live-cell, high-throughput chemical screen. By using the method and the chemical screen, Applicants identify small molecule compounds as mechanical modulators. Specifically, Applicants identify compounds such as 4-hydroxyacetophenone (4-HAP) as discussed above, which enhances the cortical localization of the mechanoenzyme myosin II, independent of myosin heavy-chain phosphorylation, thus increasing cellular cortical tension.

EXAMPLES

Figure 1B:
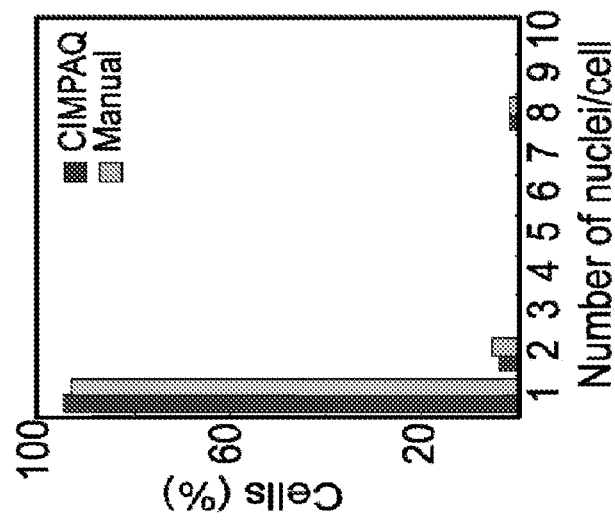
FIG. 1B shows sample histogram of a single well showing the distribution of nuclei per cell counts demonstrating high agreement between manual counts and CIMPAQ analysis. The Cartesian coordinates defined by the ratio of bi- to mono-nucleated cells and the ratio of multi- to mononucleated cells of the untreated WT wells are fitted to a two dimensional Gaussian distribution in FIG. 1C. From this distribution, contour lines for all standard deviations from the control mean are determined for a given plate as shown in FIG. 1D.
Figure 1C:
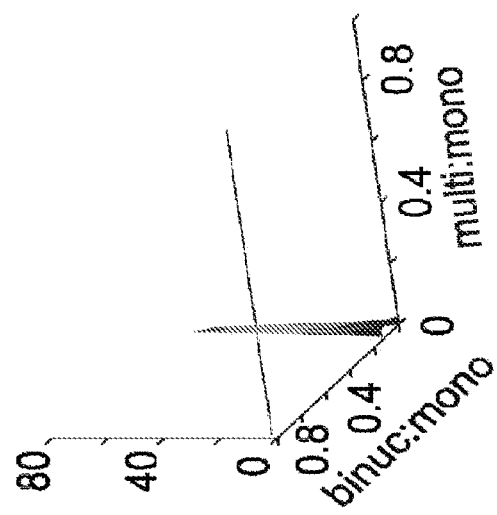
FIG. 1(A-D) are a set of diagrams and graphs showing CIMPAQ processes of high-throughput data and identification of mechanical modulators, mitotic inhibitors, and lethal compounds.
Figure 1D:
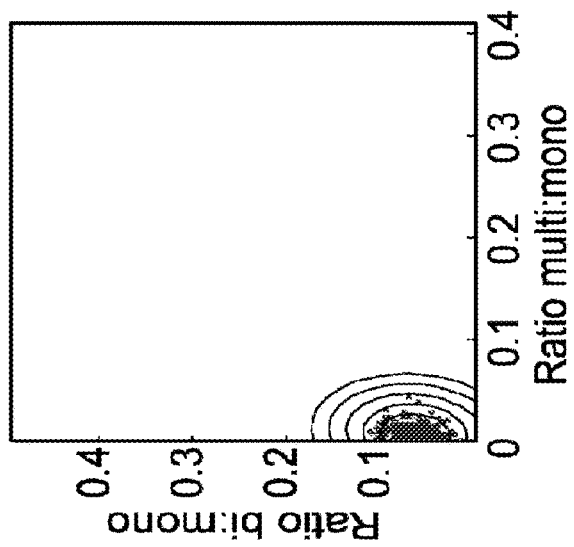

Example 1. CIMPAQ Processes of High-Throughput Data and Identification of Mechanical Modulators, Mitotic Inhibitors, and Lethal Compounds FIG. 1(A-D) are a set of diagrams and graphs showing CIMPAQ processes of high-throughput data and identification of mechanical modulators, mitotic inhibitors, and lethal compounds. FIG. 1A shows workflow diagram of primary screening from 384-well plating (i) to raw data acquisition (ii) to CIMPAQ image conversion by segmentation (iii). Cytokinesis hits are identified in a 5-step process: Acquisition of FIG. 1A(ii) raw images of NLS-tdTomato expressing cells and conversion into FIG. 1A (iii) CIMPAQ-processed version FIG. 1B shows sample histogram of a single well showing the distribution of nuclei per cell counts demonstrating high agreement between manual counts and CIMPAQ analysis. The Cartesian coordinates defined by the ratio of bi- to mono-nucleated cells and the ratio of multi- to mononucleated cells of the untreated WT wells are fitted to a two dimensional Gaussian distribution in FIG. 1C. From this distribution, contour lines for all standard deviations from the control mean are determined for a given plate as shown in FIG. 1D.

Figure 2B:
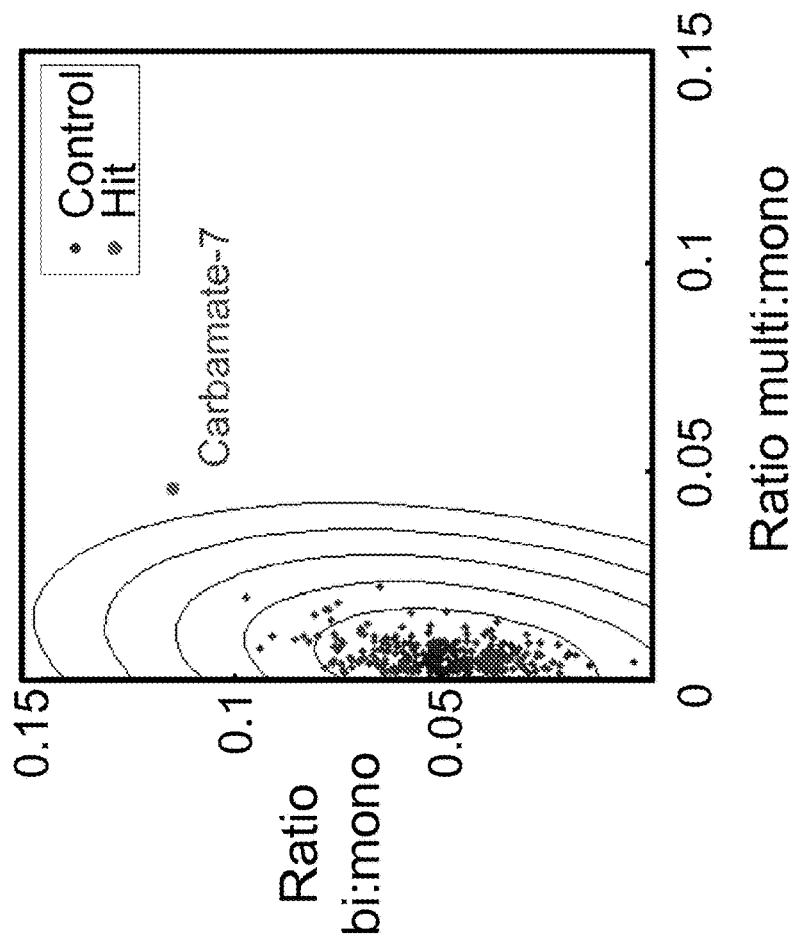
In FIG. 2B, cells treated with carbamate-7 (red) showed a shift in the nuclei/cell distribution over six standard deviations from the control data (blue), in primary screening.
Figure 2A:
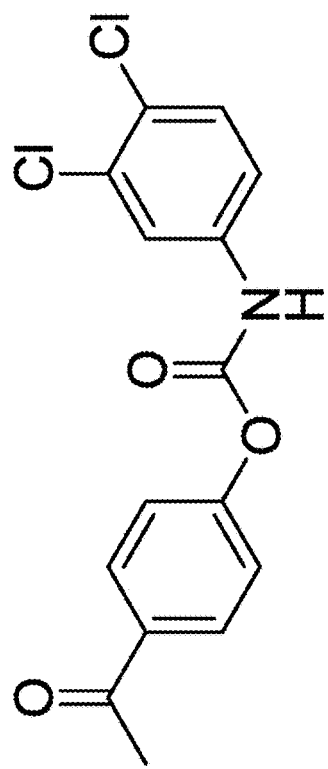
FIG. 2A shows the structure of the putative carbamate-7.
Figure 2D:
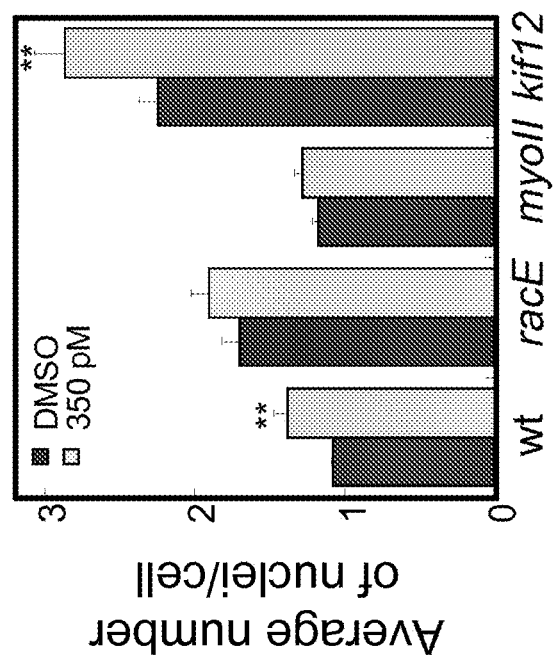
In FIG. 2D, results from synthetic lethality experiments show a statistically significant difference in the average number of nuclei/cell between untreated and treated samples in wild-type and kif12 null strains (**$p<0.0001$), but not myoI or racE null strains. Error bars represent SEM.
Figure 2C:
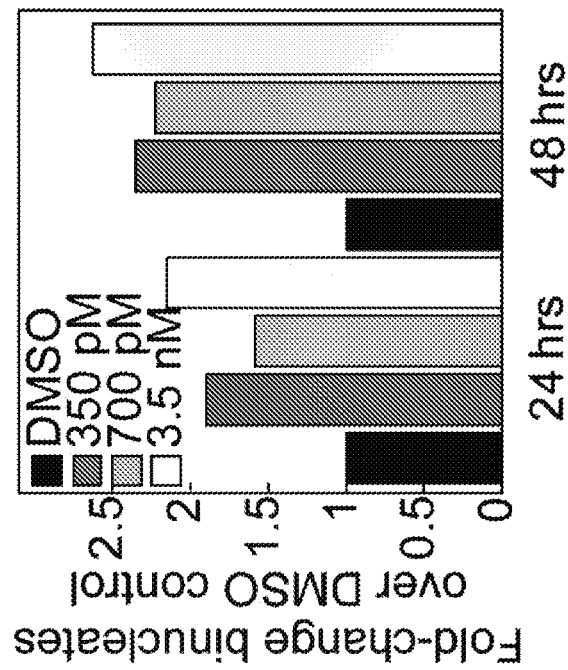
FIG. 2C shows that partial dose response curves reveal that carbamate-7 increases the fraction of binucleates at nM concentrations.

Example 2. Identification of Carbamate-7 as a Cytokinesis Inhibitor Affecting the Myosin II-Race Pathway FIG. 2(A-D) are a set of images and graphs showing the molecular structure of carbamate-7 and identification of carbamate-7 as a cytokinesis inhibitor affecting the myosin II-RacE pathway according to one embodiment of the present invention. FIG. 2A shows the structure of the putative carbamate-7. In FIG. 2B, cells treated with carbamate-7 (red) showed a shift in the nuclei/cell distribution over six standard deviations from the control data (blue), in primary screening. FIG. 2C shows that partial dose response curves reveal that carbamate-7 increases the fraction of binucleates at nM concentrations. In FIG. 2D, results from synthetic lethality experiments show a statistically significant difference in the average number of nuclei/cell between untreated and treated samples in wild-type and kif12 null strains (**$p<0.0001$), but not myoI or RacE null strains. Error bars represent SEM.

Example 3. Myosin II Cortical Dynamics Affected by Treatment with Carbamate-7

FIG. 3(A-D) are a set of images and graphs showing that myosin II cortical dynamics affected by treatment with carbamate-7 according to one embodiment of the present invention. FIG. 3A: Structural Illuminated Micrographs of myoII:GFP myoII cells show an increase in the amount and variability of myosin II bipolar thick filaments in 500-nM carbamate-7 treated (right panels) versus untreated (left panels) cells. In both, the white box represents a zoomed in region, shown to the right of the main images. FIG. 3B: Total Internal Reflection Microscopy (TIRF) images of cells treated with increasing amounts of carbamate-7 show increase of cortical GFP-myosin II, quantified in FIG. 3C. FIG. 3D: Sedimentation assay shows increase of non-monomeric myosin II in 700-nM carbamate-7 treated over untreated cells (n=3). FIG. 3E: Cortical tension measurements show a 1.4-fold increase in cells acutely treated with carbamate-7. Error bars represent SEM.

Example 4. 4-Hydroxyacetophenone Activates Myosin II

FIG. 4(A-G) are a set of images and graphs showing that 4-hydroxyacetophenone activates myosin II. FIG. 4A: Carbamate-7 degrades in DMSO to give three distinct chemical species-3,4-dichloroaniline, 4-hydroxacetophenone, and 1,2-bis-(3,4-dichloro-phenyl)-urea. FIG. 4B: Both 3,4-DCA and 4-HAP are required for the shift in binucleation observed from mixtures of carbamate-7 in DMSO, obtained commercially from ChemBridge (CB) and synthesized (syn) in house. FIG. 4C: Myosin II is enriched at the cortex in 4-HAP and both samples only. FIG. 4D: Histogram shows the relative myosin II intensities of the cortex to the cytoplasm. FIG. 4E: TIRF images show an increase in the amount and length of GFP-myosin II BTFs. FIG. 4F: 500 nM 4-HAP shows significant localization of GFP-myosin II within 10 minutes of treatment. FIG. 4G: There is a 1.5-fold increase in cortical tension of cells acutely treated with 500 nM 4-HAP. The change in effective tension (Teff) is dependent on myosin II. Neither the myoII nor S456L myosin cells show an increase in Teff. Error bars represent SEM.

Figure 5A:
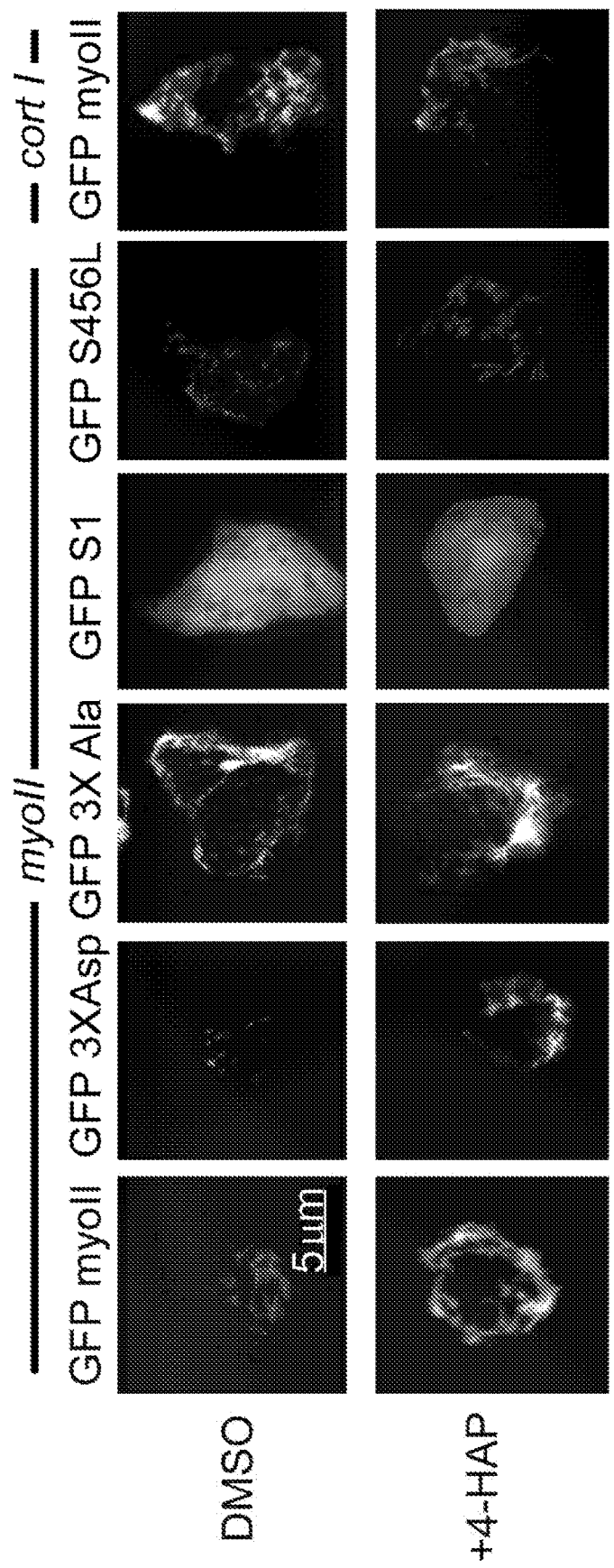
FIG. 5A-B is a set of images and graphs showing that myosin II activation by 4-HAP requires the normal power stroke and ADP-release step.
Figure 5B:
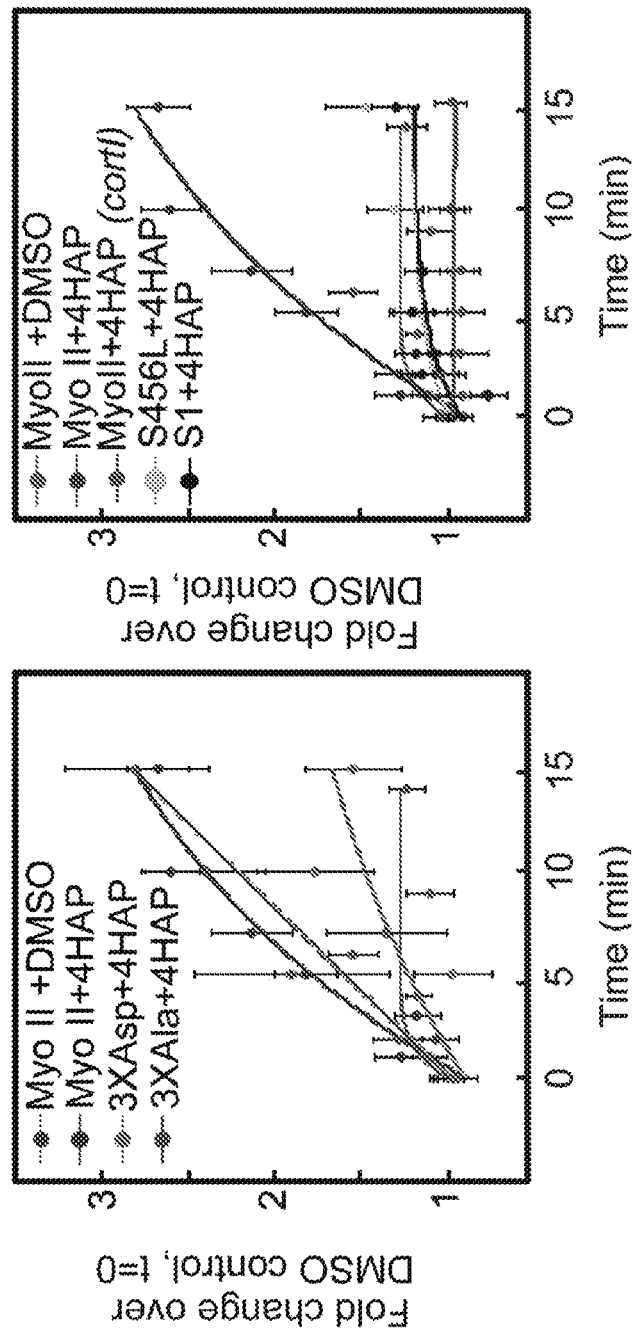

Example 5. Myosin II Activation by 4-HAP Requires the Normal Power Stroke and ADP-Release Step FIG. 5A-5B is a set of images and graphs showing that myosin II activation by 4-HAP requires the normal power stroke and ADP-release step. FIG. 5A: TIRF images of GFP-myosin II, GFP-3XAsp, and GFP-3XAla expressing myoI null cell-lines in DMSO compared to 10 min 500 nM 4-HAP treatment show an increase in BTFs across all three cell-lines. FIG. 5B shows quantification of 4-HAP time course. GFP-S1 and GFP-S456L expressing cell-lines showed no changes over untreated samples FIG. 5A over the time-course of the experiment (FIG. 5B, right panel).

Example 6. Model of Myosin II Activation by 4-HAP

Figure 6:
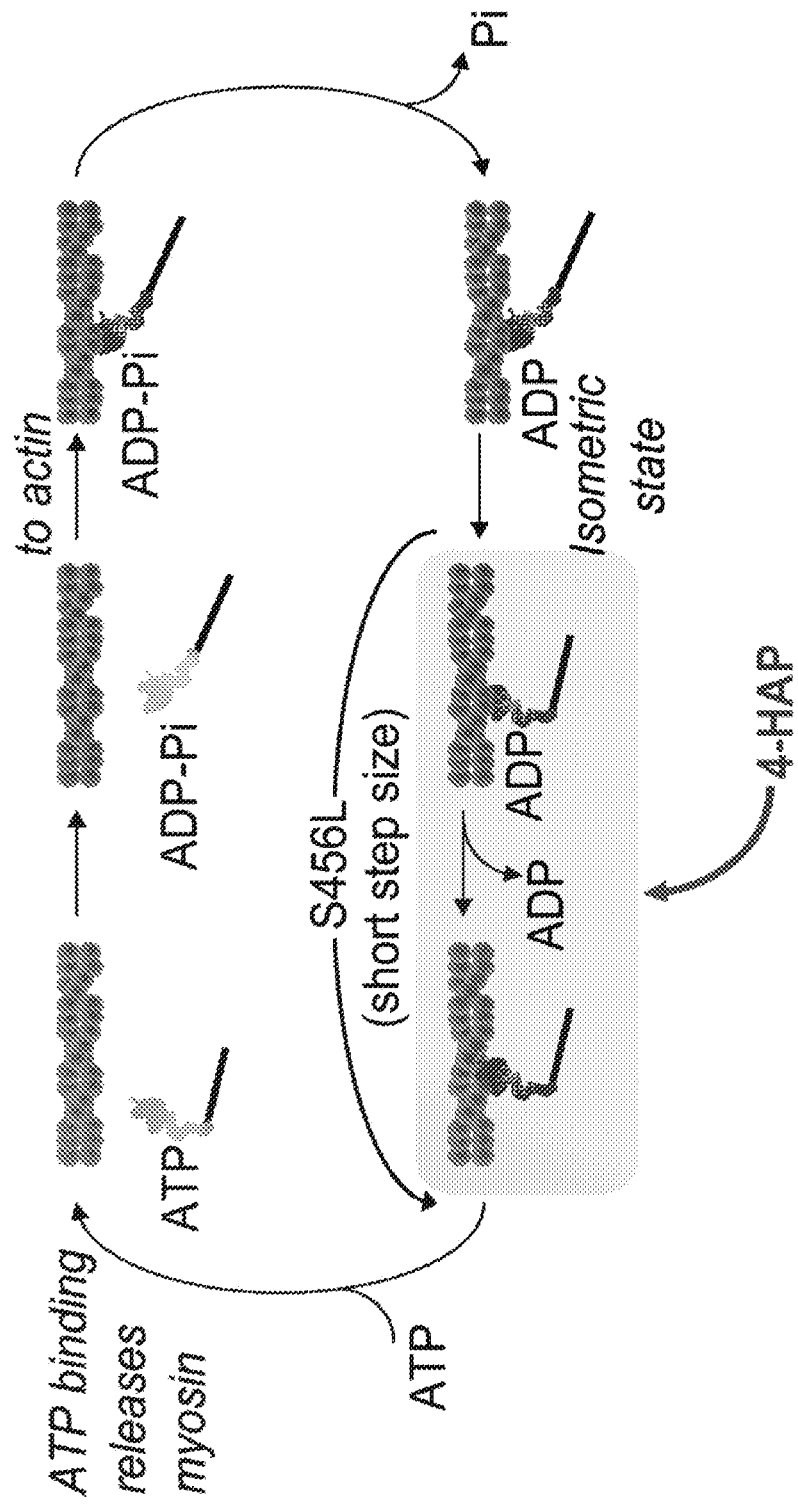
FIG. 6 is a diagram showing model of myosin II activation by 4-HAP.

FIG. 6 is a diagram showing model of myosin II activation by 4-HAP.

Figure 7:
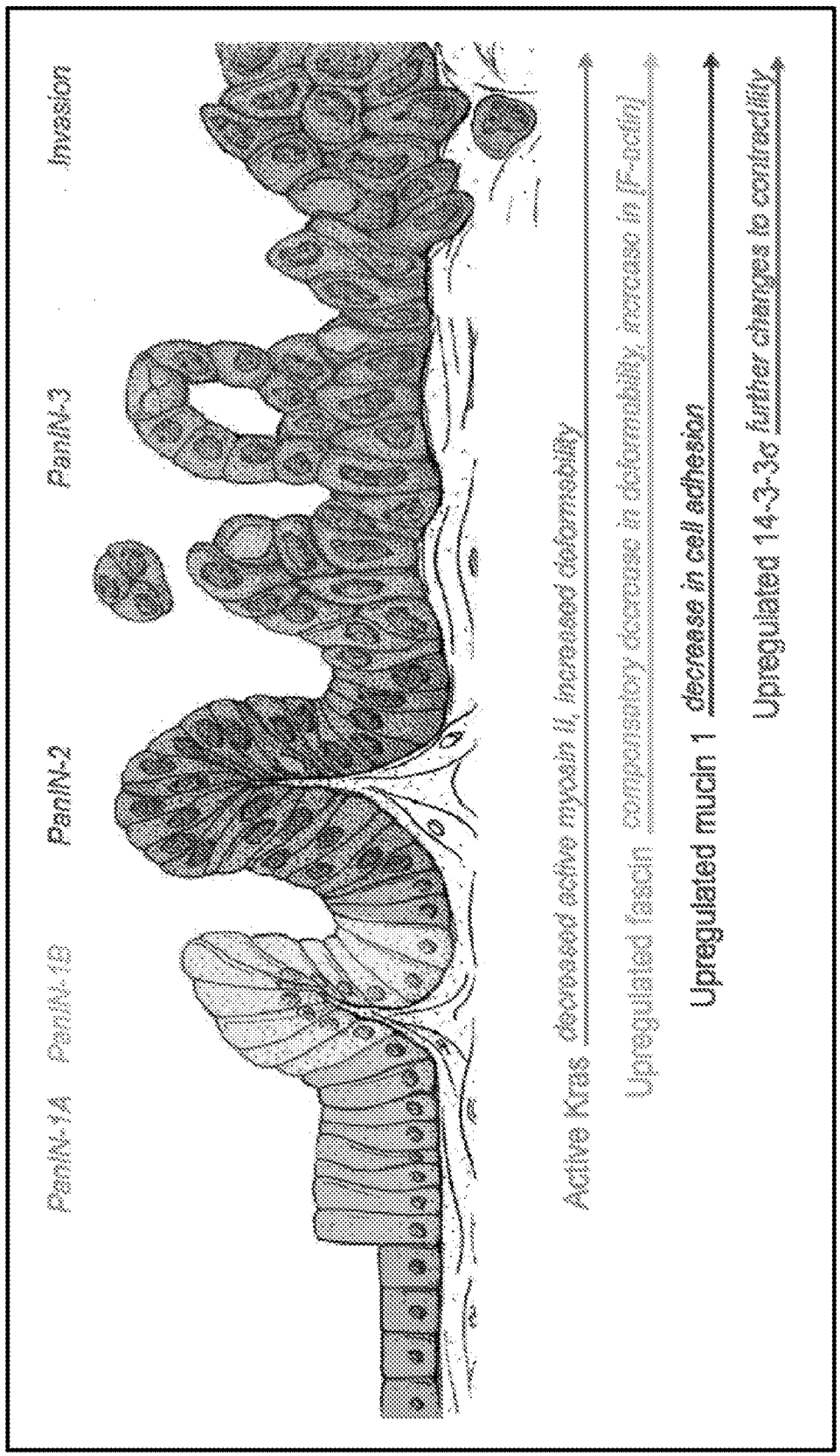
FIG. 7 is a systemic diagram showing PDAC progression likely dependent on changing mechanical landscape.

Example 7. PDAC Progression Likely Dependent on Changing Mechanical Landscape FIG. 7 is a systemic diagram showing PDAC progression likely dependent on changing mechanical landscape.

Figure 8C:
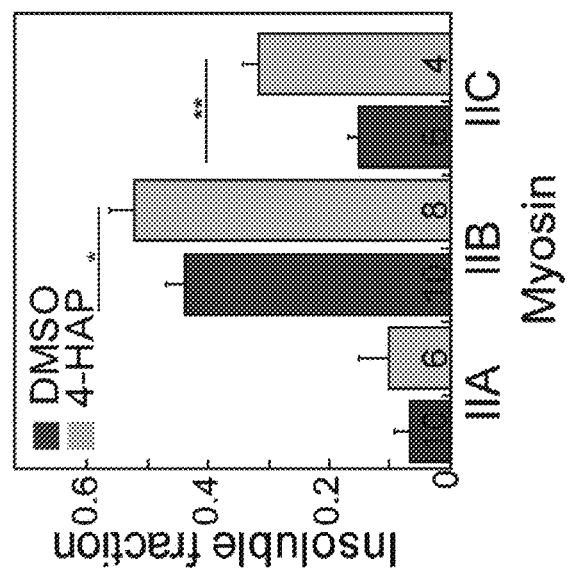
FIG. 8C: Sedimentation assay shows increases in assembled myosin IIB and IIC in HEK293 cells.
Figure 8B:
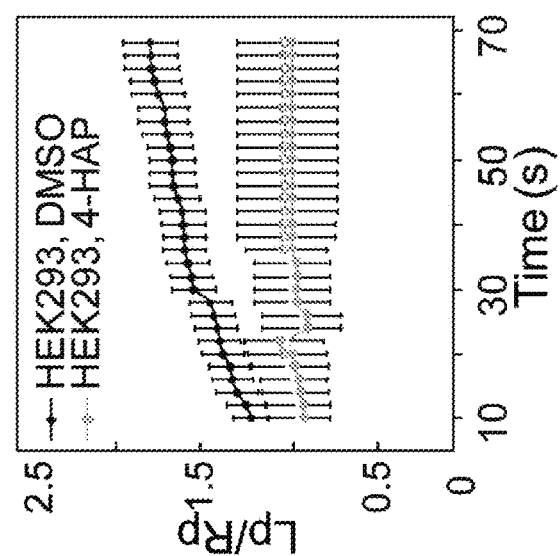
FIG. 8(A-I) are a set of images and graphs showing 4-HAP decreases the deformability of human cells and turns the mechanical profile of pancreatic cancer cells to more WT-like mechanics, decreasing their invasive capacity.
FIG. 8A: Micrographs from FIG. 8B creep tests show that 4-HAP stiffens the soft HEK293 cells (creep tests at 0.15 nN/$\mu m^2$); region of aspiration, Lp; radius of pipette, Rp.
FIG. 8D: Similarly, micrographs of aspirated cells show that 4-HAP tunes the deformability of metastatic PDAC, ASPC-1 cells.
FIG. 8E: Creep tests demonstrate that the WT pancreatic cell line HPDE is stiffer than the metastatic PDAC cell-line, ASPC-1 and that 4-HAP stiffens ASPC-1 cells, shifting them towards HPDE-like mechanics (creep tests at 0.25 nN/$\mu m^2$); region of aspiration, Lp; radius of pipette, Rp.
FIG. 8F: 4-HAP increases assembled myosin IIC in ASPC-1 cells, and HPDE cells (FIG. 15H); n provided on bars; *$p=0.04$, $p=0.007$, *$p=0.005$.
FIG. 8G: 4-HAP does not alter the cortical tension of HL-60 cells which lack the myosin IIB and IIC paralogs. All experiments presented here were performed using cell treated with 500 nM 4-HAP for 1 hr. Migration (FIG. 8H) and invasion (FIG. 8) assays of ASPC-1 cells show a dose-dependent decrease upon 4-HAP treatment. n provided on bars; **$p<0.0001$, *$p=0.01$ for migration assay; *$p=0.02$ for invasion assay.
Figure 8A:
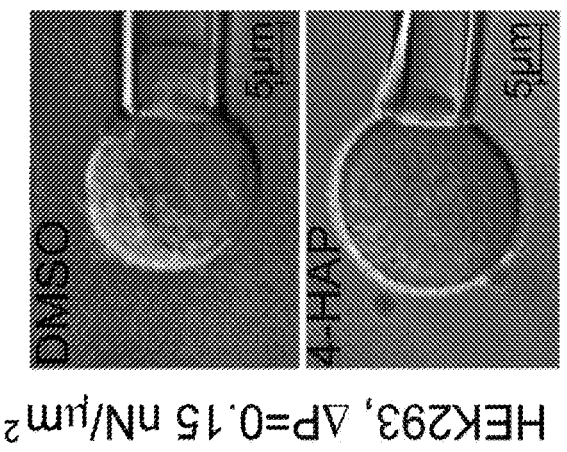
Figure 8F:
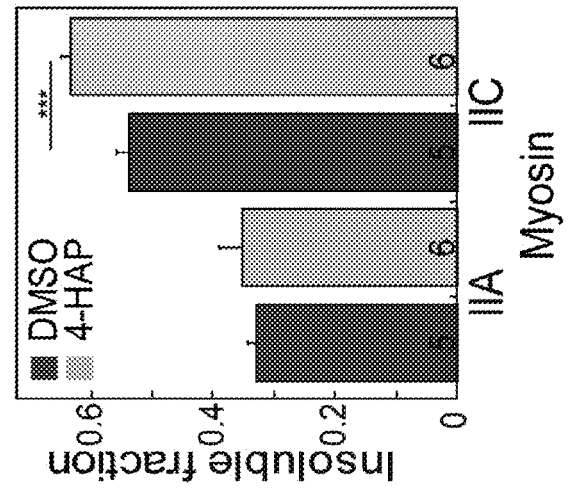
Figure 8E:
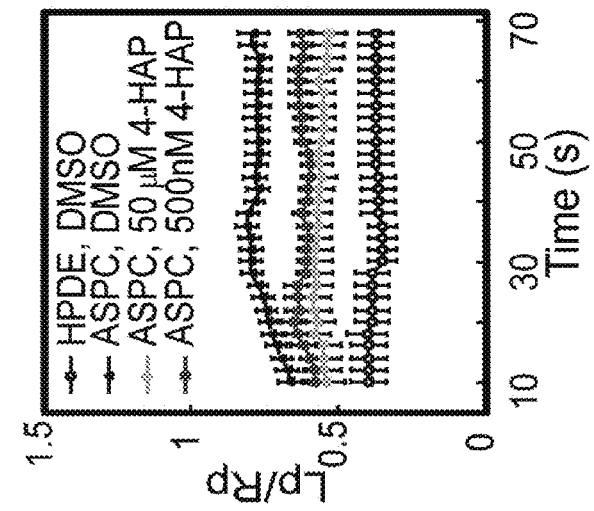
Figure 8D:
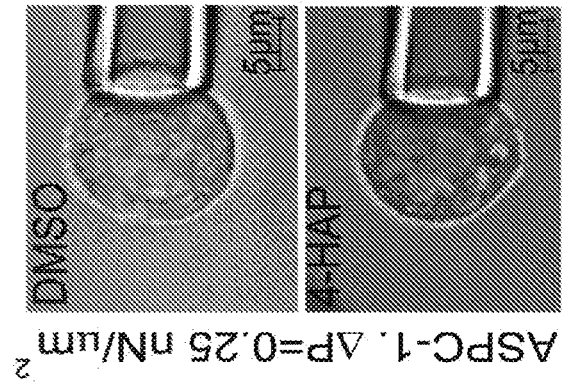
Figure 8I:
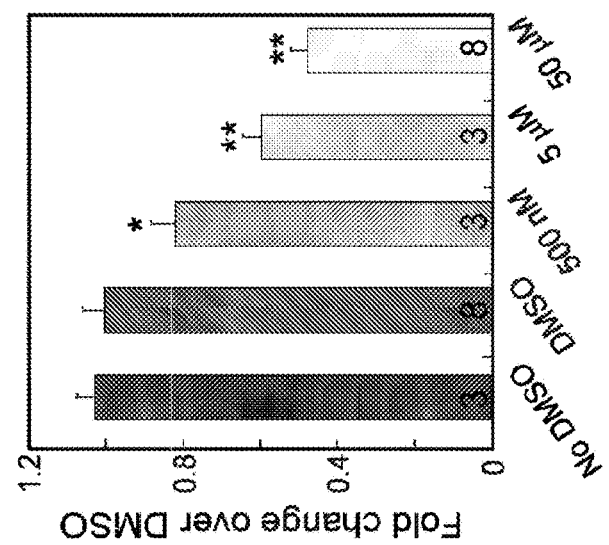
Figure 8H:
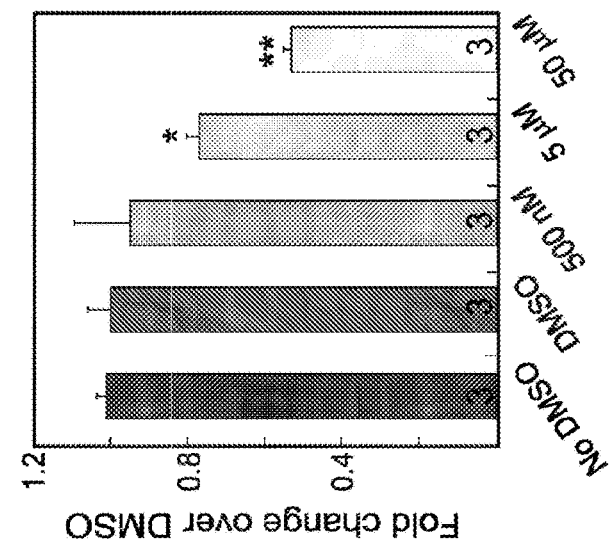
Figure 8G:
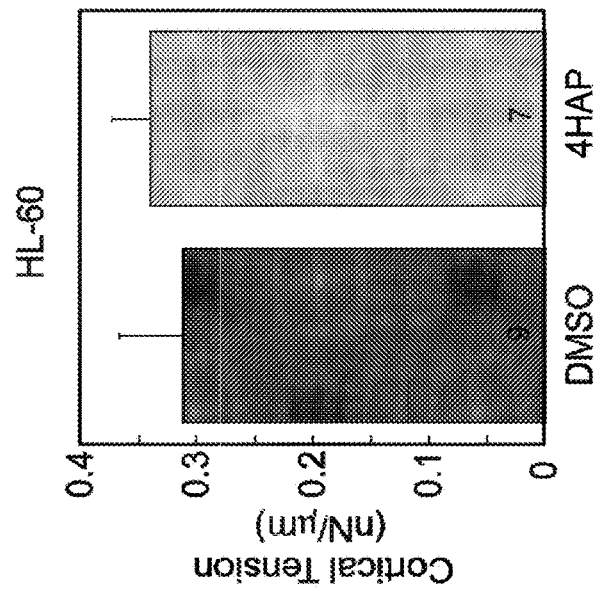

Example 8. 4-HAP Restores PDAC Mechanics Towards Wild Type (WT) Mechanics, Working Through Myosin IIB and IIC FIG. 8A-8I are a set of images and graphs showing 4-HAP decreases the deformability of human cells and turns the mechanical profile of pancreatic cancer cells to more WT-like mechanics, decreasing their invasive capacity. FIG. 8A: Micrographs from FIG. 8B creep tests show that 4-HAP stiffens the soft HEK293 cells (creep tests at 0.15 nN/$\mu$m$^2$); region of aspiration, Lp; radius of pipette, Rp. FIG. 8C: Sedimentation assay shows increases in assembled myosin IIB an IIC in HEK293 cells. FIG. 8D: Similarly micrographs of aspirated cells show that 4-HAP tunes the deformability of metastatic PDAC, ASPC-1 cells. FIG. 8E: Creep tests demonstrate that the WT pancreatic cell line HPDE is stiffer than the metastatic PDAC cell-line, ASPC-1 and that 4-HAP stiffens ASPC-1 cells, shifting them towards HPDE-like mechanics (creep tests at 0.25 nN/$\mu$m$^2$); region of aspiration, Lp; radius of pipette, Rp. FIG. 8F: 4-HAP increases assembled myosin IIC in ASPC-1 cells, and HPDE cells (FIG. 15H): n provided on bars; *p=0.04, p=0.007, *p=0.005. FIG. 8G: 4-HAP does not alter the cortical tension of HL-60 cells which lack the myosin IIB and IIC paralogs. All experiments presented here were performed using cell treated with 500 nM 4-HAP for 1 hr. Migration (FIG. 8H) and invasion (FIG. 8) assays of ASPC-1 cells show a dose-dependent decrease upon 4-HAP treatment. n provided on bars; **p<0.0001, *p=0.01 for migration assay; *p=0.02 for invasion assay.

Example 9. Methods

CIMPAQ Work Flow

Figure 9A:
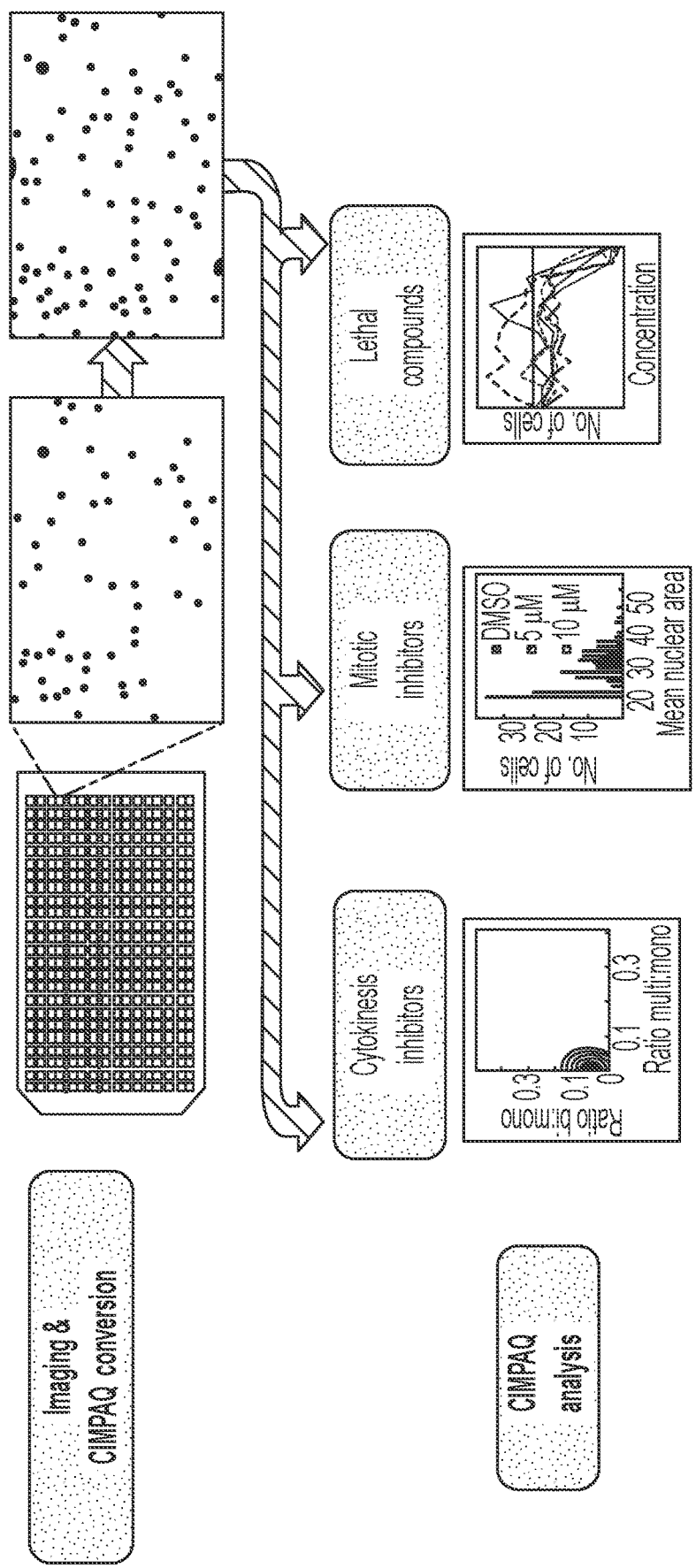
FIG. 9A: Overview work-flow diagram of primary screening from 384-well plating to raw data acquisition to CIMPAQ image conversion by segmentation. CIMPAQ analyzes the segmented data to identify and rank-order cytokinesis inhibitors, mitotic inhibitors, and lethal compounds.
Figure 9D:
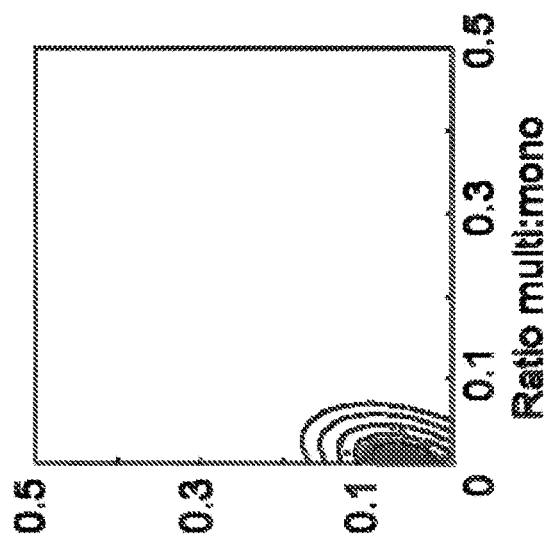
FIG. 9(A-I) are diagrams and graphs showing that CIMPAQ processes high-throughput data and identifies cytokinesis inhibitors.
FIG. 9G: Sample histogram of a single well showing the distribution of nuclei per cell counts demonstrating high agreement between manual counts and CIMPAQ analysis. Over 50,000 cells have been manually counted to cross compare with CIMPAQ output.
FIG. 9H: The Cartesian coordinates defined by the ratio of binucleate (2 nuclei/cell) to mononucleate cells and the ratio of multinucleate (>2 nuclei/cell) to mononucleate cells of the untreated WT wells are fitted to a two dimensional Gaussian distribution. From this distribution, contour lines for all standard deviations from the control mean are determined for a given plate (FIG. 9I). Each blue dot represents one untreated control well from a 384-well plate.
Figure 9C:
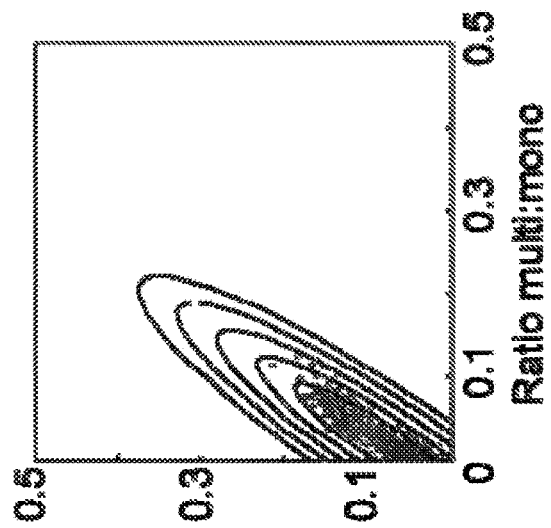
Figure 9B:
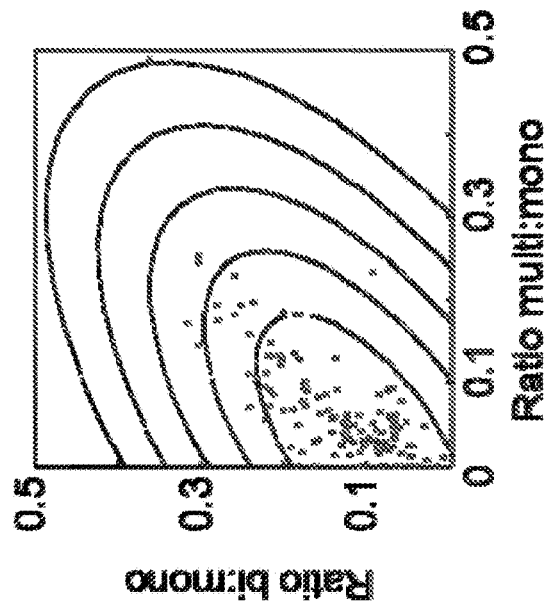

An overview of the primary screen, including CIMPAQ analysis, is presented in FIG. 9A.

Screen Development and CIMPAQ Analysis

NLS-tdTomato expressing *Dictyostelium* cells were challenged with 5 M compounds from the ChemBridge DivertSET library and imaged over three days. Raw data was segmented by CIMPAQ, a designed analytical platform, which rank ordered hits based on their cytokinesis or mitotic inhibitory activity, or lethality. Hits were confirmed through a dose-dependent secondary screening.

Cell Strains and Culture

*Dictyostelium discoideum* strains used in this study are listed in Table 1. *Dictyostelium* strains were grown at 22° C. in Hans' enriched HL-5 media or ForMedium, with either G418 or hygromycin for selection. Cells grown for primary and secondary chemical screening were cultured in enriched HL-5 media (1.4XHL-5 enriched with 8% FM) with penicillin and streptomycin at 22° C. in 384-well Cyclo Olegin Polymer (COP) plates (Aurora Biotechnologies, Vancouver, British Columbia). These plates were chosen for their optical characteristics that generated a tighter distribution of nuclei/cell counts, preferable to other plates we tested [FIGS. 9(B-D)]. All other cells were cultured in ForMedium with penicillin and streptomycin at 22° C. on 10-cm Petri dishes (Robinson D N, et al., 2000) or grown in suspension in 200-ml flasks. The myoII null cells (Ruppel K M, et al., 1995), racE null cells (Gerald N, et al., 1998), cort null cells (Robinson D N, et al., 2000), and kif12 null cells (Lakshmikanth G, et al., 2004) have been described previously. NLS-tdTomato was prepared by cloning the sequence in the pLD1 vector. Transformation of all strains was achieved by electroporation using a Genepulser-II electroporator (Bio-Rad, Hercules, Calif.).

TABLE 1

Strains used in the Application.

| Strain | Genotype | Experimental Applications |
|---|---|---|
| WT control | Ax3(Rep orf+) | Compound testing, MPA |
| Ax3::NLS-tdTomato | Ax3(Rep orf+)::NLS-tdTomato, G418$^R$ pLD1 | Compound testing |
| cortI$^{1151}$ | cortI$^{1151}$ (HS1151) | CIMPAQ testing |
| racE | $\Delta$racE | Compound testing |
| myoII | myoII (HS1) | Compound testing, MPA, western blot |
| kif12 | kif12 (Rep orf+) | Compound testing |
| myoII::GFPmyoII; RFPtub | myoII (HS1)::GFPmyoII, G418$^R$: pBIG; RFP-$\alpha$-Tubulin, Hyg$^R$: pDRH | SIM, TIRF, compound testing, sedimentation assay, MPA |
| myoII::GFP3XAsp; RFPtub | myoII (HS1)::GFP3XAla, G418$^R$: pBIG; RFP-$\alpha$-tubulin, Hyg$^R$: pDRH | TIRF, compound testing |
| myoII::GFP3XAla; RFPtub | myoII (HS1)::GFP3XAsp, G418$^R$: pBIG; RFP-$\alpha$-tubulin, Hyg$^R$: pDRH | TIRF, compound testing |
| myoII::GFPS456L; RFPtub | myoII (HS1)::GFPS456L, G418$^R$: pBIG; RFP-$\alpha$-tubulin, Hyg$^R$: pDRH | TIRF, compound testing |
| myoII::GFPS1; RFPtub | myoII (HS1)::GFPS1, G418$^R$: pBIG; RFP-$\alpha$-tubulin, Hyg$^R$: pDRH | TIRF, compound testing |

TABLE 1-continued

Strains used in the Application.

| Strain | Genotype | Experimental Applications |
|---|---|---|
| cortl$^{1151}$::GFPmyoII; RFPtub | cortl$^{1151}$ (HS$^{1151}$)::GFPmyoII, GFPmyoII, G418$^R$: pBIG; RFP-α-tublin, Hyg$^R$: pDRH | TIRF, compound testing |

Transformed cells were selected with 10-15 μg/ml G418, 15-50 μg/ml hygromycin, or both when two plasmids were transformed together. E For drug treatment, cells were pre-incubated with 0.1% DMSO for 4 hrs before treatment. A1.7 cells were grown according to standard cell culture methods in DMEM high glucose (Gibco, Grand Island, N.Y.) with 1% penicillin and streptomycin and 10% FBS on cell culture petri dishes.

HPDE and ASPC-1 cells were grown according to standard cell culture methods, respectively in Keratinocyte media (Gibco, Grand Island, N.Y.), with 1% penicillin and streptomycin or RPMI 1640, L-Glutamine media (Gibco, Grand Island, N.Y.), supplemented with 1% penicillin and streptomycin, sodium pyruvate, 10% EFBS and 0.2% insulin. HL-60 cells were grown in RPMI supplemented with 1% antibiotic-antimycotic mix (Invitrogen), 25 mM HEPES (Invitrogen) and 20% EFBS. For drug treatment, cells were pre-incubated with 0.1% DMSO overnight. In accordance with NIH guidelines, cell lines were authenticated using short tandem repeat STR profiling in the genetic recourses core facility at Johns Hopkins University.

Micropipette Aspiration and Microscopy

Micropipette aspiration was used for cortical tension and creep response measurements. Confocal imaging was performed on a Zeiss 510 Meta with a 63× (numerical aperture [NA] 1.4) objective (Carl Zeiss, Jena, Germany). Epifluorescence and TIRF imaging was performed in a 22° C. temperature controlled room with an Olympus IX81 microscope using a 40× (NA 1.3) or 60× (NA 1.49) objective and a 1.4× optovar (Olympus, Center Valley, Pa.), as previously described. Image analysis was performed with ImageJ (rsb.info.nih.gov/ij).

In Vitro Protein Assays

The sedimentation assays were used to assess myosin II assembly in cells. The assembly assay used purified proteins (N-terminal 6×His tag (SEQ ID NO: 1), fused to the mCherry fluorophore, fused to the assembly domains of Dictyostelium myosin II (residues 1533-1823), human myosin IIA (residues 1722-1960), and human myosin IIB (residues 1729-1976), and 6×His-tagged (SEQ ID NO: 1) fused Dictyostelium 14-3-3). Purified chicken nonmuscle IIB heavy meromyosin (HMM) was used for in vitro motility.

Primary and Secondary Chemical Library Screening

Ax3::NLS-tdTomato cells were plated on 384-well COP plates with a MicroFloSelect microplate dispenser (BioTek, Winooski, Vt.) at volumes of 80 μl with a cell concentration of 1000 cells/ml for the 24- and 48-hr time points and at the same volume with a cell concentration of 220 cells/ml for the 72-hr time point. Each plate contained four rows of untreated cells with 0.2% DMSO. For the remaining wells, 5 M of each small molecule maintained at the Johns Hopkins ChemCORE facility, was added, with a final DMSO concentration of 0.2%. Almost half of the ChemBridge DivertSET library, which is a 50,000 compound chemical diversity library, was screened over a three-day period on a Becton Dickinson Pathway 855 Bioimager System using a 20× objective (NA 0.75). Each image consisted of a montage of four images collected around the center of the well, resulting in a total size of 1344×1024 pixels per image.

Secondary chemical screening was carried out in quadruplicate, with identical culturing conditions as to the primary screen. 14 mM stocks of each compounds dissolved in 100% DMSO were diluted to the following final concentrations: 350 μM, 3.5 nM, 35 nM, 350 nM, 3.5 μM, and 35 μM.

CIMPAQ Processing, Analysis, and Hit Identification

Figure 9G:
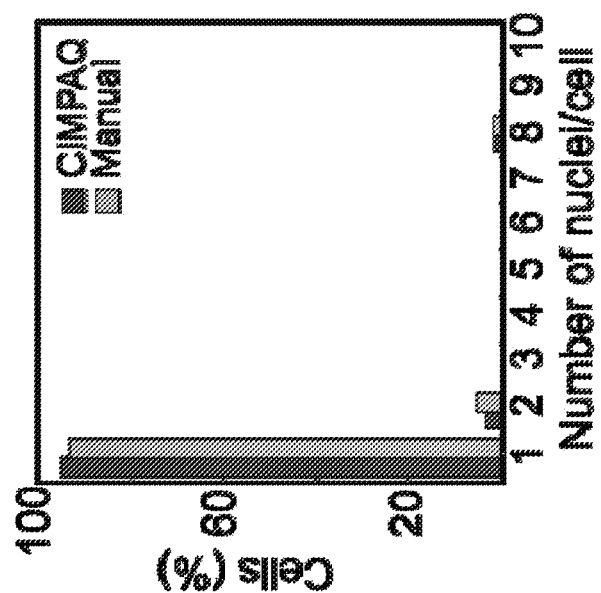
Figure 9F:
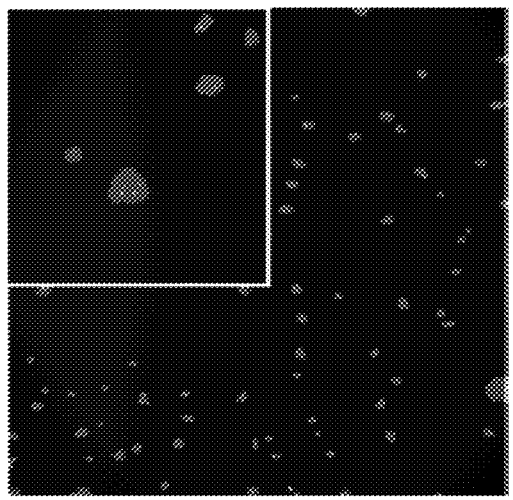
Figure 9E:
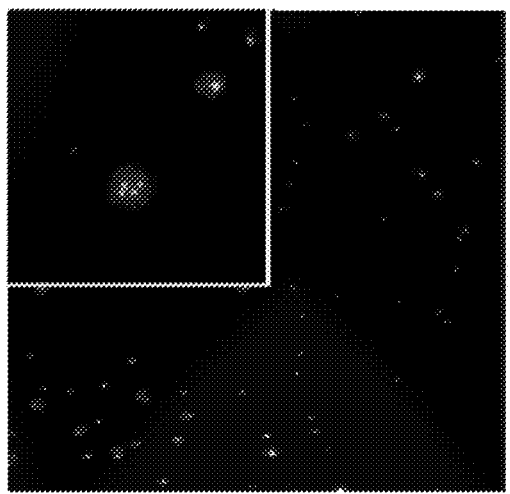

Image Processing Using CIMPAQ:

Raw image files from both the primary and secondary screening were processed through CIMPAQ (FIGS. 9E and 9F). The single wavelength fluorescence images were converted from 16-bit format to 8-bit format. The MATLAB Image Processing Toolbox was utilized to segment the images in order to identify the nuclei and cytoplasm. The number of nuclei within each segmented cell was quantified to produce a histogram of nuclei per cell for each image (FIG. 9G). All segmented cells that were coincident with the image edge were disregarded.

Figure 9I:
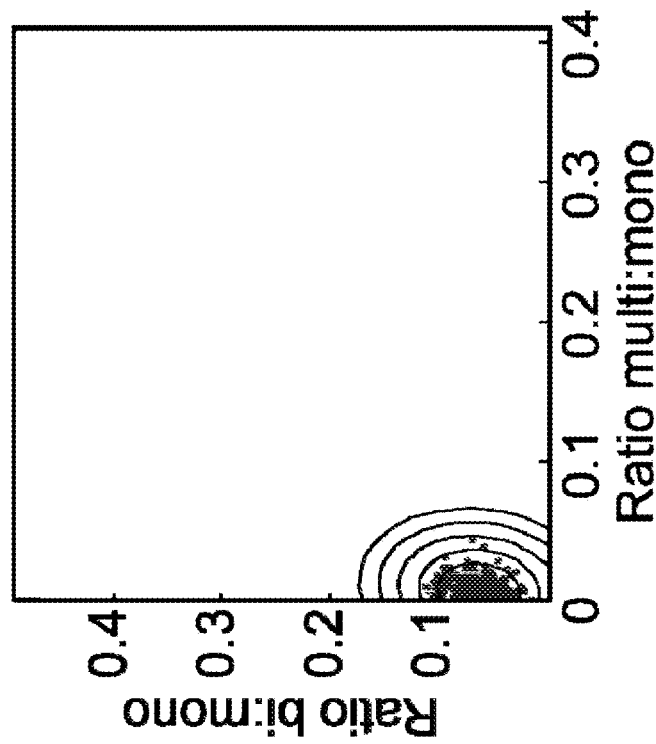
Figure 9H:
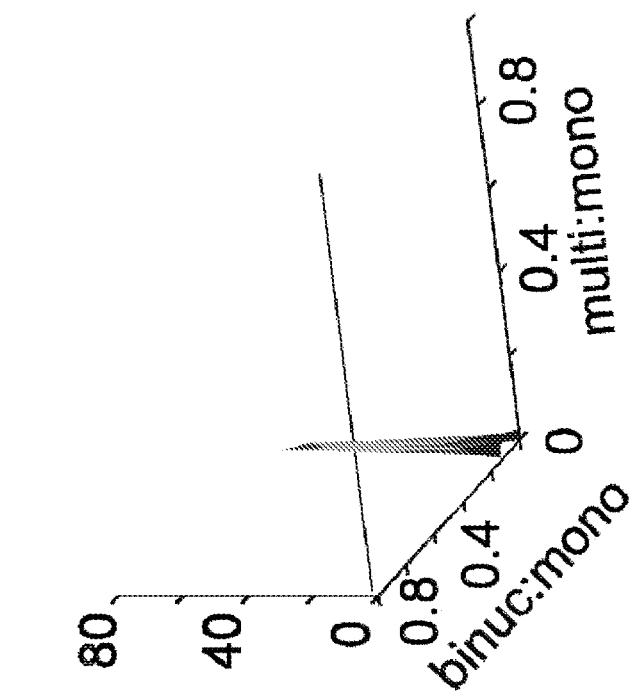

Image analysis using CIMPAQ: From the histogram of nuclei per cell count, the ratio of the number of multinucleate cells to the number of mononucleate cells and the ratio of the number of binucleate cells to the number of mononucleate cells were computed. Multinucleate cells are defined as cells that contain >2 nuclei. The distribution of both ratios across multiple wells were simultaneously visualized using a scatter plot, with the ratio of multinucleate cells to mononucleate cells plotted on the x-axis and the ratio of binucleate cells to mononucleate cells plotted on the y-axis (FIGS. 9H and 9I). Other information such as the average number of nuclei per cell, the mean nuclear area, and the normalized histogram with respect to total cell number were also computed.

Hit identification using CIMPAQ: Compounds that generate an increase in the number of multinucleate (>2 nuclei/cell) cells are considered cytokinesis inhibitors. Because nearly all cultured cells, including Dictyostelium, have a low background (typically <5% for WT) of non-mononucleate cells, CIMPAQ spreads the data for each sample by determining the ratio (bi:mono) of binucleate (2 nuclei/cell) to mononucleate cells and the ratio (multi:mono) of multinucleate (>2 nuclei/cell) to mononucleate cells. These two ratios then define a set of Cartesian coordinates, describing the effect of each compound on a given cell-line. The coordinates for each compound are plotted on a two-dimensional graph. CIMPAQ fits the control data to a two-dimensional Gaussian distribution (FIG. 9H) and determines the contour lines for two standard deviations (2SD), 3SD, etc. from the control mean (FIG. 9I).

Hit compounds are rank-ordered based on how many SDs away they are from the untreated wells. To fit the nuclei/cell ratios, we utilized the MATLAB Statistics and Optimization Toolboxes and fitted the ratios data from the control wells with a bivariate Gaussian function. The fitted parameters of the Gaussian function were used to assign a metric number to each sample well. The metric number is defined as the value of the Gaussian function when evaluated at the ratio values computed for a sample well of interest:

metric number=$f$(ratio multi:mono sample,ratio bi:mono sample)

where $f(x,y)$=fitted Gaussian function

Based on the definition, a smaller metric number corresponds to larger deviations of the ratio pair from the control mean ratios. The cutoff for a well to be considered a hit was that the ratio pair had to be >2 standard deviations from the control mean ratios. All identified hits were further categorized by the number of standard deviations away from the control mean ratios.

Figure 10A:
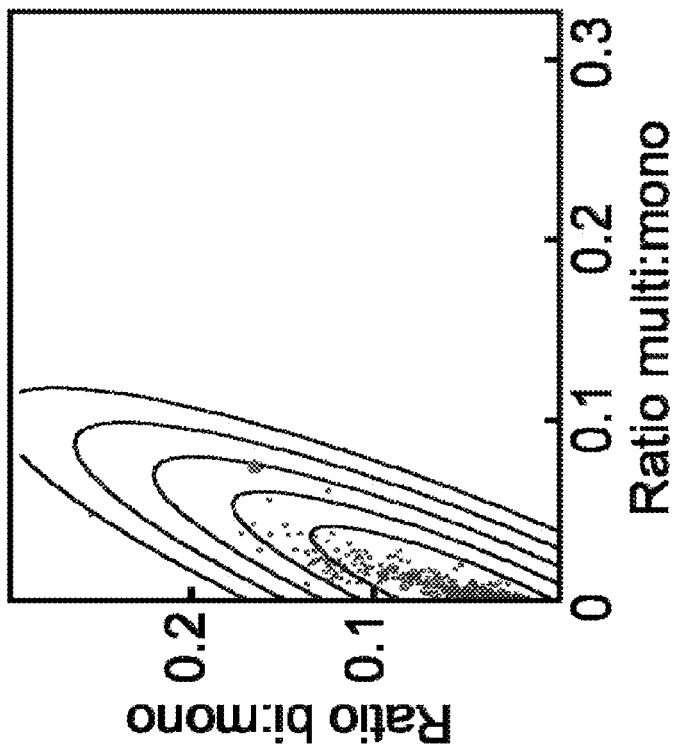
FIG. 10A: CIMPAQ identified 86% of wells plated with cortexillin I null cells, which are deficient in cytokinesis (cort null wells, red; WT wells, blue).

To assess the efficacy of CIMPAQ in identifying cytokinesis inhibitors, a 384-well plate containing primarily the AX3::NLS-tdTomato cell line, was randomly seeded with cortexillin I null (a cytokinesis mutant) cells transformed with the NLS-tdTomato construct. CIMPAQ was able to identify 86% of the cortexillin I-containing wells (FIG. 10A).

Mitotic Inhibitors:

Early mitotic inhibitors were identified using a simple threshold value where the average nuclear area is greater than 28 pixels. Untreated WT control cells had a tight nuclear area of 22 pixels. This threshold value reliably identified cells treated for 24 hrs and 48 hrs with 5 M and 10 M nocodazole, a known microtubule destabilizing agent [FIGS. 10(D-F)].

Lethal Compounds:

Lethal compounds were identified based on the total number of cells detected in the acquired image. Wells that had significantly fewer cells compared to the control (>2 SDs difference, typically 10% of average number of cells from all untreated wells) were counted as wells that contain a lethal compound at the 5 M concentration used in the primary screening. Because data was collected over three days, growth inhibitors were also identified using similar metrics.

Figure 10B:
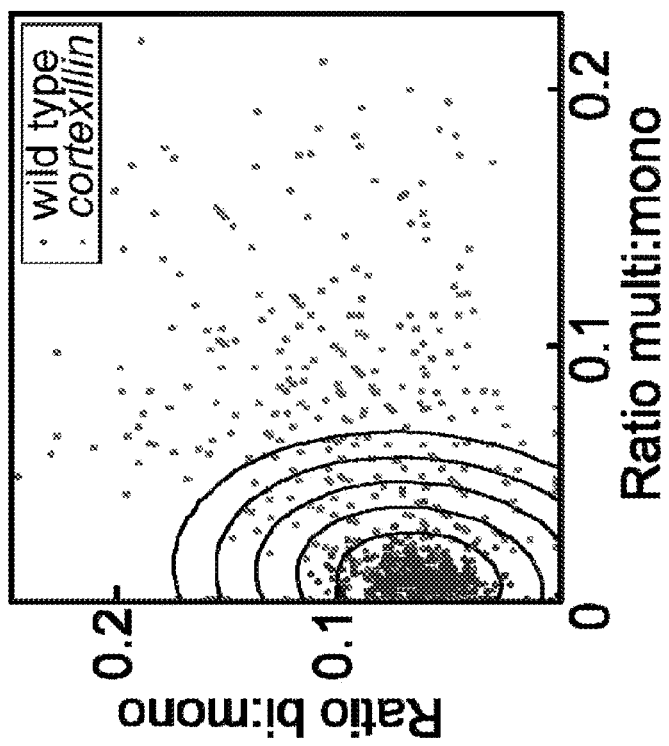
FIG. 10B: A sample CIMPAQ plot of hit compound (red) from the primary screen of the BIOMOL kinase collection, which is ranked 4 standard deviations away from the control data (blue).
Figure 10E:
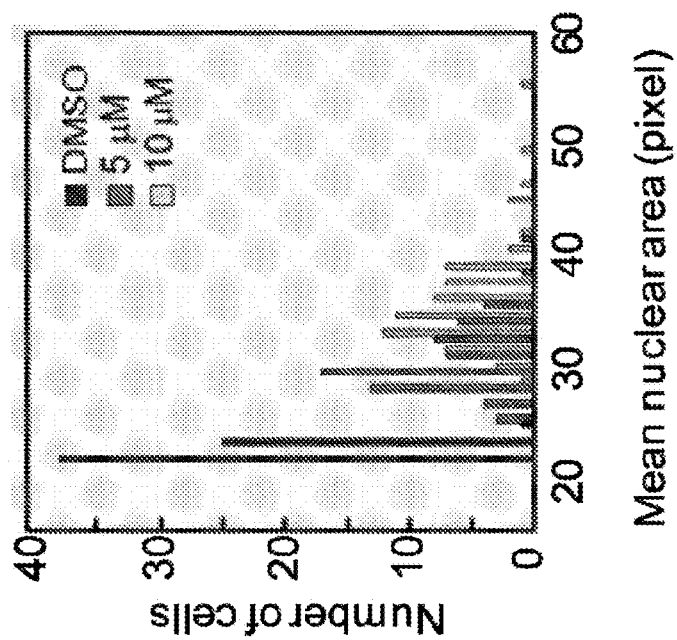
FIG. 10(A-E) are diagrams and graphs showing validation of CIMPAQ efficiency for cytokinesis and mitotic inhibitors.
FIG. 10D: Raw images of 10 M nocodazole-treated cells are processed by CIMPAQ (FIG. 10E). CIMPAQ uses a simple threshold of 28 pixels for the mean nuclear area to identify early mitotic inhibitors. Distributions of the nuclear area of untreated cells (dark gray), 5-µM nocodazole-treated cells (medium gray, middle), and 10-µM nocodazole-treated cells (light gray) are shown.
Figure 10D:
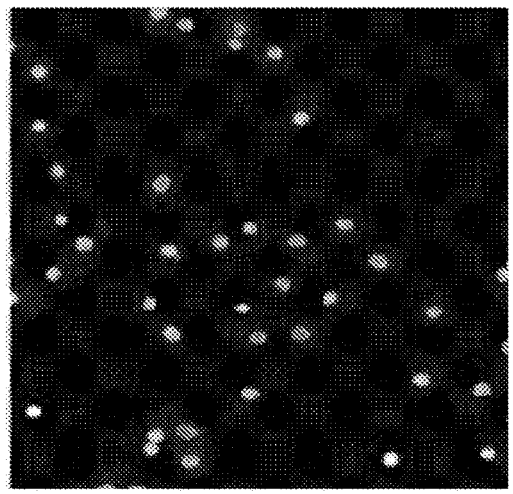
Figure 10C:
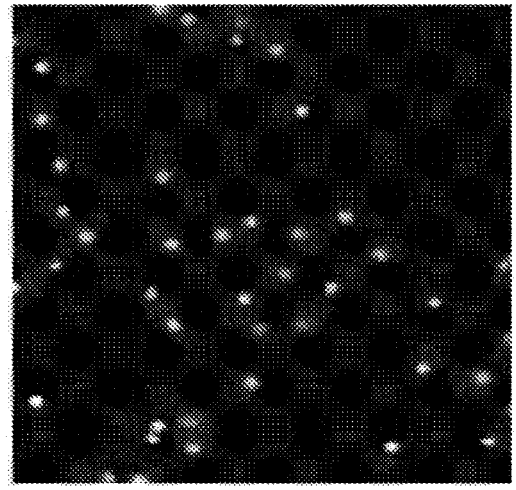

Library Testing of CIMPAQ:

To test CIMPAQ, original pilot screens were performed on two parts of the BIOMOL collection—84 protein kinase inhibitors and 70 ion channel inhibitors (data summary of hits from these collections are listed in Tables 2 and 3; sample CIMPAQ output, FIG. 10B). In each of these setups, manual counts were compared with CIMPAQ-generated numbers. Overall, over 50,000 nuclei/cell distributions were manually counted for cross-validation of the CIMPAQ software.

TABLE 2

CIMPAQ hits identified from the kinase inhibitor collection.

| | CAS number | Name | Pathway affected |
|---|---|---|---|
| Cytokinesis inhibitors (non-lethal) | 24386-93-4 | 5-Iodotubercidin | Inhibits ERK2, adenosine kinase, CK1, CK2, and insulin receptor kinase |
| | 62004-35-7 | LFM-A13 | Tyrosine kinase inhibitor |
| Cytokinesis inhibitors (lethal, 5 days) | 220904-83-6 | GW 5074 | A benzylidine oxindole derivative that inhibits the Raf/MEK/ERK2 kinase cascade by blocking the kinase activity of c-Raf1 |
| | 446-72-0 | Genistein | Isoflavin that inhibits tyrosine kinase and has been previously reported to inhibit cytokinesis |
| | 63177-57-1 | Erbstatin analog | EGF receptor tyrosine kinase inhibitor; known IC50 (0.5 μg/ml); efficiently delays onset EGF-induced DNA synthesis |
| | 4452-06-6 | ZM 449829 | JAK-3 tyrosine kinase inhibitor; binds competitively to Jak3 ATP site; inhibits STAT-5 phosphorylation and T-cell proliferation |
| Lethal at 5 μM | 167869-21-8 | PD-98059 | MAP kinase inhibitor |
| | 10537-47-0 | Tyrphostin 9 | PDGF receptor tyrosine kinase |
| | 172889-26-8 | PP1 | Src family tyrosine kinase inhibitor |
| | | AG-370 | PDGF receptor kinase inhibitor |
| | 548-04-9 | Hypericin | Protein kinase C inhibitor |
| Lethal at 10 μM | | 2-Hydroxy-5-(2,5-dihydroxy benzylamino) benzoic acid | Inhibits CAM Kinase II, EGF receptor tyrosine kinase, and pp60 kinase |
| | 6865-14-1 | Palmitoyl-DL-carnitine Cl | PKC inhibitor |

TABLE 3

CIMPAQ hits identified from the ion channel collection.

| | CAS number | Name | Pathway affected |
|---|---|---|---|
| Cytokinesis inhibitors (non-lethal) | 6151-40-2 | Quinidine | Sodium channel blocker |
| | 21306-56-9 | QX-314 | Sodium channel blocker |
| | 29094-61-9 | Glipizide | Potassium channel blocker |
| | 113558-89-7 | E-4031 | Potassium channel blocker |
| Cytokinesis inhibitors (lethal, 5 days) | 54527-84-3 | Nicardinpin | Calcium channel blocker |
| | 2062-78-4 | Pimozide | Calcium channel blocker |
| | 107254-86-4 | NPPB | Miscellaneous channel |

TABLE 3-continued

CIMPAQ hits identified from the ion channel collection.

| | CAS number | Name | Pathway affected |
|---|---|---|---|
| Lethal at 5 µM | 52665-69-7 | Antibiotic A-23187 | Intracellular calcium blocker |
| | 130495-35-1 | SKF-96365 | Calcium channel blocker |
| | 74764-40-2 | Bepridil | Calcium channel blocker |
| | 113317-61-6 | Niguldipine | Calcium channel blocker |

Imaging and Image Analysis

Imaging conditions during primary screen are described above. All other image analysis was performed as previously described (Kee Y S, et al., 2012). Cells were transferred from Petri dishes (with 0.1% DMSO incubation in growth media of 4 hrs) to imaging chambers and allowed to adhere for 20 min in growth media with 0.1% DMSO. After the cells adhered, the growth media was replaced with 2-(N-morpholino)ethanesulfonic acid (MES) starvation buffer (50 mM MES, pH 6.8, 2 mM $MgCl_2$, 0.2 mM CaCl2) with 0.1% DMS. Confocal imaging was performed on aZeiss 510 Meta with a 63× (numerical aperture [NA] 1.4) objective (Carl Zeiss, Jena, Germany). Epifluorescence and TIR imaging was performed in a 22° C. temperature controlled room with an Olympus IX81 microscope using a 40× (NA 1.3) or 60× (NA 1.8) objective and a 1.4× optovar (Olympus, Center Valley, Pa.), as previously described. Image analysis was performed with ImageJ (rsb.info.nih.gov/ij). Many data sets were independently analyzed by multiple investigators.

Micropipette Aspiration Assay, Cortical Tension Measurements, and Creep Tests

The instrumental and experimental setups have been previously described (Effler J C, et al., 2006; Kee Y-S, et al., 2013). Micropipette aspiration assays were all carried out in growth media with 0.1% DMSO. For cortical tension measurements of *Dictyostelium* cells, pressure was applied to the cell cortex with a micropipette (2-3 m radius, Rp) to the equilibrium pressure ($\Delta P$) where the length of the cell inside the pipette (Lp) was equal to Rp. The effective cortical tension ($T_{eff}$) was calculated by applying the Young-Laplace equation: $\Delta P=2Teff(1/Rp-1/Rc)$, where Rc is the radius of the cell and $\Delta P$ is the equilibrium pressure when Lp=Rp (Derganc J, et al., 2000; Octtaviani E, et al., 2006). For creep tests on mammalian strains, a constant aspiration stress was applied over 60 s. The micropipette radius was 3.5-4.5 m. For quantification, the Lp/Rp ratio values was measured every two seconds and plotted as a function of time. A10.7 and HEK293 cells could only be aspirated at a low pressure range (0.15 nN/µm$^2$), while HPDE, ASPC-1, and HL-60 cells could be aspirated at higher pressure ranges (0.25 nN/µm$^2$) because they were stiffer.

Sedimentation Assay

*Dictyostelium* Sedimentation Protocol:

The sedimentation protocol was modified from Yumura et al. (Yumura S, et al., 2005) 1.5×10$^6$ cells were pelleted for 5 min at 2000 rpm. The pellet was washed in MES starvation buffer (50 mM MES, pH 6.8, 0.2 M $CaCl_2$), 2 mM $MgCl_2$) and then resuspended in Buffer A (0.2 M MES, pH 6.8, 2.5 mM EGTA 5 mM $MgCl_2$, 0.5 mM ATP) and incubated on ice for 5 min. An equal volume of Buffer B (Buffer A+1% Triton X-100+protease inhibitor cocktail) was added, and the samples were vortexed for 5 s, followed by 5 min of incubation on ice. The supernatant, after a 10,000 g spin for 2 min at 4° C., was transferred to a fresh tube. The Triton-insoluble pellet was dissolved in 50 µl sample buffer and heated for 5 min at 100° C. 2× volume −20° C. acetone was added to the supernatant which was subsequently incubated on ice for 10 min and then centrifuged at 10000 g for 10 min at 4° C. The Triton-soluble fraction was dissolved in 50 µl sample buffer and heated for 5 min at 100° C. Samples were loaded on a 15% SDS-polyacrylamide gel.

Mammalian Cell Sedimentation Protocol:

Sedimentation protocol was adapted from the protocol above. 3×10$^6$ cells were pelleted for 5 min at 2000 rpm and washed in 1 ml PBS. The pellet was resuspended in 100 µl lysis buffer (50 mM PIPES, pH 6.8, 46 mM NaCl, 2.5 mM EGTA, 1 mM $MgCl_2$, 1 mM ATP, 0.5% Triton X-100, and protease inhibitors—PI cocktail, PMSF, TLCK, Aprotinin). Samples were vortexed briefly and incubated on ice for 20 min, followed by centrifugation at 15,000 g for 5 min at 4° C.

Pellet was resuspended in 100 µl lysis buffer minus Triton X-100, and both pellet and supernatant fractions were heated to 100° C. for 3 min with RNaseA. Samples were incubated at 37° C. for 30 min and then heated to 100° C. in sample buffer for 5 min. Samples were loaded on a 15% SDS-polyacrylamide gel. Western blot analyses of phospho-myosin IIA was performed on whole cell lysates of cells treated as above in lysate buffer with 10 mM NaF.

Assembly Assay

Protein Purification:

Bacterial expression plasmids coding for an N-terminal 6×His tag (SEQ ID NO: 1), fused to the mCherry fluorophore, fused to the assembly domains of *Dictyostelium* myosin II (residues 1533-1823), human myosin IIA (residues 1722-1960), or human myosin IIB (residues 1729-1976) were generated using standard cloning techniques.

*Dictyostelium* 14-3-3 was also expressed in bacteria as a 6×His-tagged (SEQ ID NO: 1) fusion protein (Zhou Q et al., 2010). Proteins were expressed in BL-21 Star™ (DE3) (Invitrogen) *E. coli* in LB shaking culture overnight at room temperature. Bacteria were harvested by centrifugation and lysed by lysozyme treatment followed by sonication, and the lysate was clarified by centrifugation. Polyethyleneimine (PEI) was added to a final concentration of 0.1% to precipitate nucleic acids, which were then removed by centrifugation. 14-3-3 precipitated in the PEI pellet, which was resuspended in column running buffer (10 mM HEPES, pH 7.1, 500 mM NaCl, 10 mM imidazole), clarified by centrifugation and filtration, and run on a Ni-NTA metal affinity column to obtain high-purity 14-3-3. The myosin constructs remained in the PEI supernatant and were precipitated by adding ammonium sulfate to 50% saturation and centrifuging. The pellet was resuspended in column running buffer and run on a Ni-NTA metal affinity column, followed by a sizing column. Protein purity was verified by SDS-PAGE followed by Coomassie Blue staining, and concentration was quantified by UV absorbance using the calculated extinction coefficient for each protein's amino acid sequence.

Assembly Assay:

In vitro assembly of myosin was conducted according to the method of Zhou et al, 2010 (Zhou Q et al., 2010), with a number of modifications. The protein concentration for each species in the tube was increased to 1 M to ensure that the smaller protein was adequately visible by Coomassie Blue staining, and the incubation time and temperature was adjusted to 30 min at the physiological temperature for each myosin species (22° C. for *Dictyostelium* myosin, 37° C. for human myosins). These temperatures were also used during the centrifugation step.

Motility Assay

The chicken non-muscle IIB (NMIIB) HMM construct (residues 1-1228, GenBank™ accession number M93676, no splice insert) was purified as previously described (Norstrom M F, et al., 2010). Motility assays were performed at 22° C. and imaged on Zeiss Axiovert 200 microscope with an Andor Luca camera. The flow cells were constructed using a glass slide, two pieces of double-sided tape, and nitrocellulose-coated coverslip. Flow cells were incubated with 0.05 mg/ml green fluorescent protein antibodies (MP Biomedicals, 0.05 mg/ml in assay buffer (AB) without DTT: 25 mM KCl, 25 mM Imidazole·HCl, pH 7.5, 1 mM K·EGTA, 4 mM $MgCl_2$; 2 min incubation time), followed by a bovine serum albumin block (1 mg/ml in AB—as above with 10 mM DTT; 6 min incubation time). NMIIB was added to the flow cell at a concentration of 420 nM and incubated for 2 min. The flow cell was rinsed with AB and then incubated for 2 min with 50 nM F-actin in AB, stabilized with TRITC-phalloidin (American Peptide Company). The flow cell was washed again with AB. Finally, Motility Buffer was added, and actin filaments were visualized. Motility Buffer for "None" (control) contained 2 mM ATP, 2 mM free $Mg^{2+}$, 0.086 mg/ml glucose oxidase, 0.014 mg/ml catalase, and 0.09 mg/ml glucose in AB. Motility Buffers with compounds contained 0.0036% (v/v) DMSO, and 500 nM 4-HAP, 500 nM 3,4-DCA, or 250 nM of 4-HAP and 250 nM 3,4-DCA as indicated for each experiment.

Chemistry

Synthesis of 4-acetylphenyl (3,4-dichlorophenyl)carbamate

To a mixture of 4-hydroxyacetophenone (250 mg, 1.8 mmol) in dichloromethane (4.6 mL) at room temperature was added 3,4 dichlorophenyl isocyanate (380 mg, 2.0 mmol) in one portion, followed by addition of iPr2NEt (32 µL, 0.18 mmol) in one portion. A white precipitate formed immediately upon addition of iPr2NEt. Dichloromethane (2 mL) was added to enable more efficient stirring of the thick white mixture. The reaction was complete within 1 hr as determined by TLC analysis. The reaction mixture was partitioned between water and chloroform in a separatory funnel, and the aqueous layer was extracted with chloroform (3×10 mL). Organic layers were combined and dried over sodium sulfate. Purification of carbamate-7 was carried out on a Grace Reveleris flash chromatography system using a linear gradient (100% hexanes→100% ethyl acetate).

The carbamate product precipitated from fractions and was collected for NMR characterization. 1H NMR analysis in methanol-d4 indicated the isolated carbamate (129 mg, 20%) is identical to commercial carbamate-7 (ChemBridge) in all respects. 1H NMR (500 MHz, methanol-d4) δ 7.84-7.94 (m, 2H), 7.73 (d, J=2.04 Hz, 1H), 7.39 (d, J=8.80 Hz, 1H), 7.32 (dd, J=2.52, 8.80 Hz, 1H), 6.77-6.88 (m, 2H), 2.52 (s, 3H).

Degradation of Carbamate-7 (5180622) in DMSO:

Upon standing in methanol, the product obtained above degraded within 2.5 hr, as determined by TLC analysis. Degradation appeared more rapid in DMSO, the solvent used to generate stock solutions for biological evaluation. Thus, carbamate-7 obtained either by chemical synthesis or commercially from ChemBridge was dissolved in DMSO (1 mg/mL), and a time course to study its degradation was initiated immediately upon solvation. To stop the degradation reaction such that the product distribution could be captured at early time points, aliquots (40 µL) were rapidly frozen into Eppendorf tubes incubating on dry ice. HPLC analysis on a Beckman Gold Nouveau HPLC System was performed on each sample immediately upon thawing. Carbamate-7 (5180622) degradation products were eluted at 3 mL/min from a Grace Alltima C18 column (length=53 mm, ID=7 mm, particle size=3 µM) over a linear gradient (5:95 acetonitrile/100 mM $NH_4OAc$ (pH 6.8) to 100% 100 mM $NH_4OAc$ (pH 6.8) over 15 min). An HPLC stack plot depicting carbamate-7 degradation over time (FIG. 11B) is displayed at 254 nm.

Figure 11A:
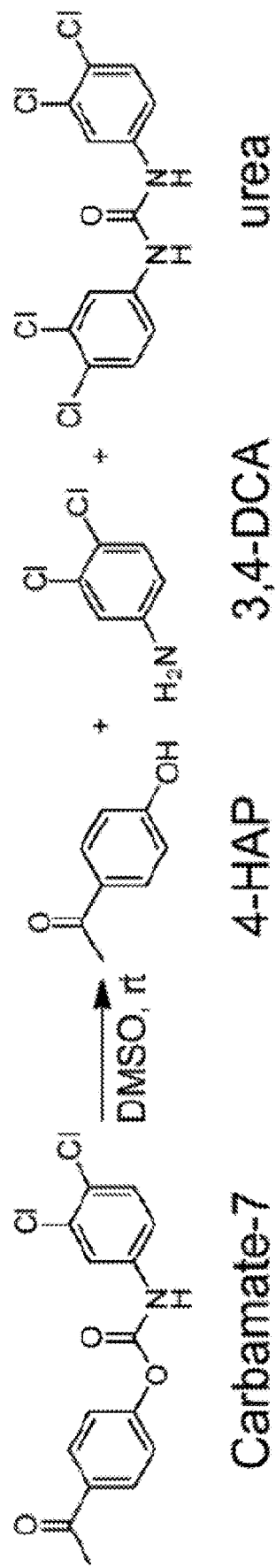
FIG. 11A: Degradation of carbamate-7 produces 3,4-dichloroaniline (3,4-DCA), 4-hydroxyacetophenone (4-HAP) and N,N'-bis(3,4-dichlorophenyl)urea (urea).
Figure 11B:
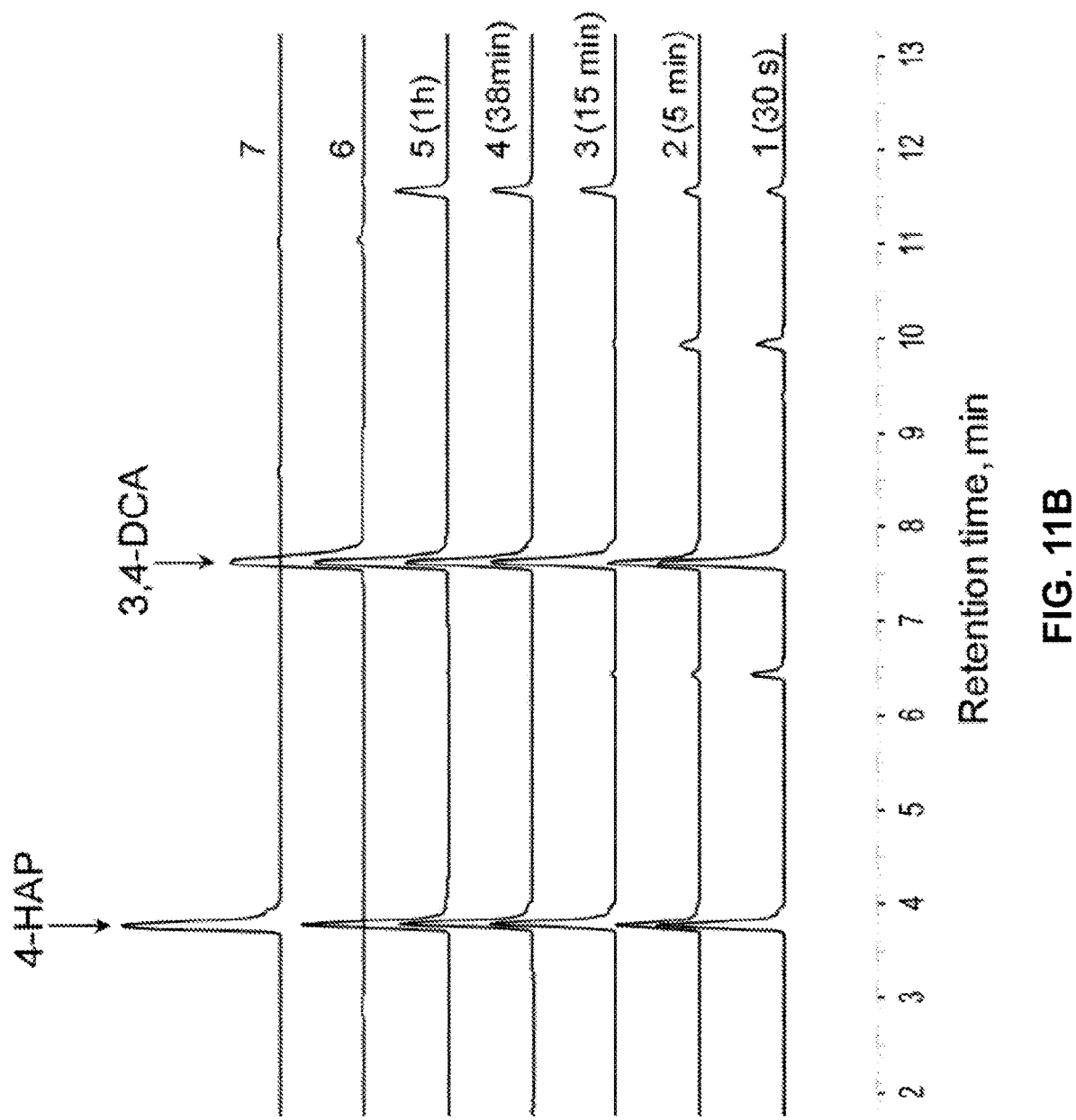
FIG. 11B: HPLC stack plot showing degradation of synthetic and commercial (Source—Chembridge) carbamate-7 in DMSO, and comparison of degradation products to authentic 3,4-DCA and 4-HAP.
Figure 11C:
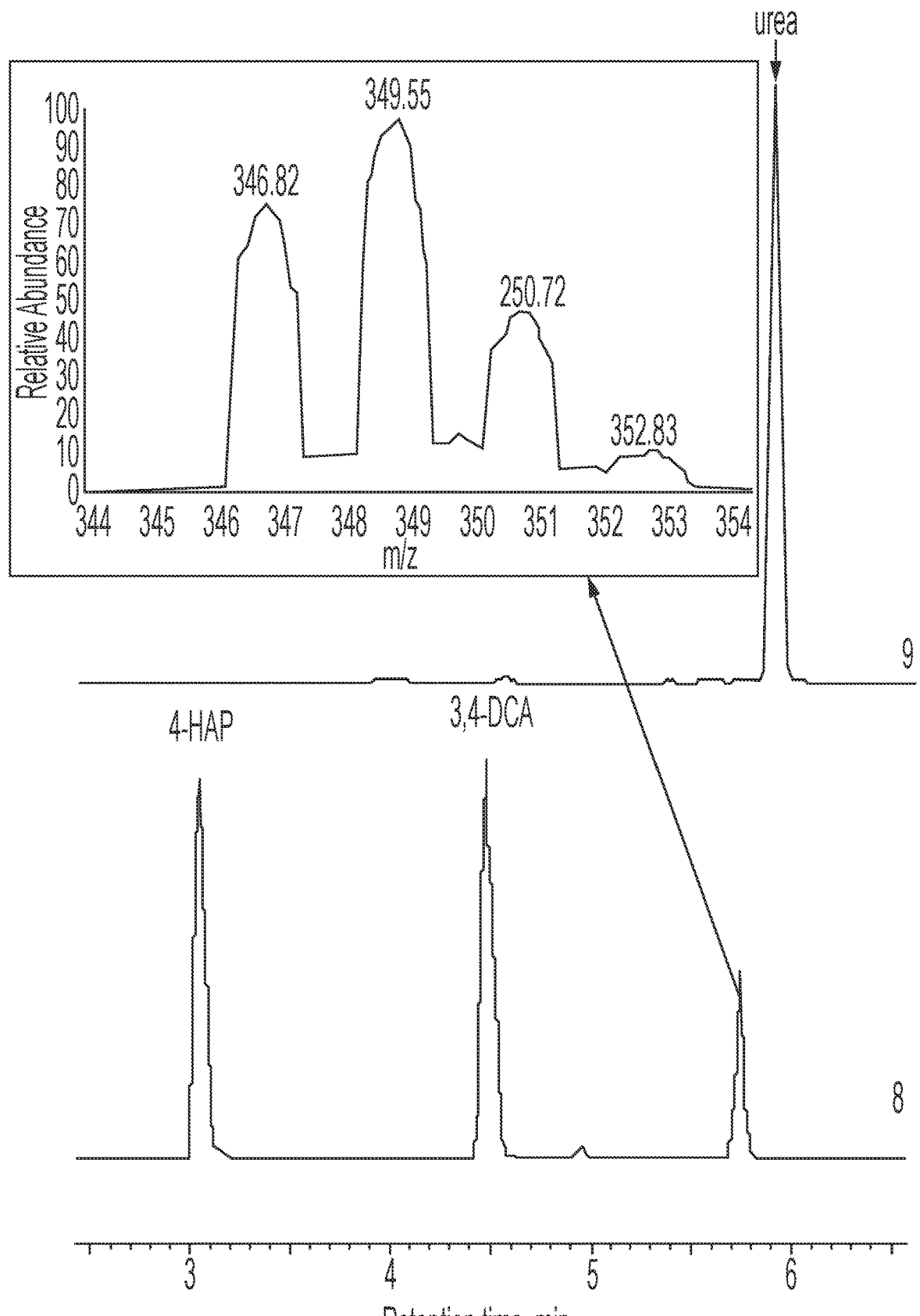
FIG. 11C: Comparison of the urea degradation product to authentic N,N'-bis(3,4-dichlorophenyl)urea by HPLC analysis. The presence of the urea was also confirmed by mass spectrometry analysis (FIG. 11C, inset) which shows the characteristic isotopic distribution for N,N'-bis(3,4-dichlorophenyl) urea.

Synthetic and commercial carbamate-7 exhibit identical reactivity in DMSO to give 4-hydroxyacetophenone (4-HAP), 3,4-dichloroaniline (3,4-DCA) and N,N'-Bis(3,4-dichlorophenyl)urea (FIG. 11A). Comparison of the urea product to authentic N,N'-Bis(3,4-dichlorophenyl) urea was performed using a linear gradient (5:95 acetonitrile/100 mM $NH_4OAc$ (pH 6.8) to 100% 100 mM $NH_4OAc$ (pH 6.8) over 5 min). The urea was also confirmed by mass spectrometry analysis using a Thermo Scientific™ TSQ Vantage triple quadrupole mass spectrometer interfaced with a Dionex u3000 uHPLC. Parent mass analysis and isotopic distribution of the urea was confirmed by direct infusion for Q1 analysis in negative ion mode. Confirmation of the urea was further confirmed via characteristic fragmentation patterns determined using product ion (MS-MS) analysis monitoring in negative ion mode (FIG. 11C).

Migration Assay

Cells were starved with serum-reduced media for 24 hr, harvested from flasks with trypsin/EDTA, washed with media containing 1% FBS, and resuspended at cell density of $2-5\times10^5$ cells/ml. 0.2 ml of cells were placed in the upper chamber of transwell (BD Biosciences), with 20% FBS-containing media in the lower well and incubated at 37° C. for 24 hr. Both sides of the transwell contained 4-HAP at the appropriate concentration, with final DMSO concentration at 0.0025%. The transwells were MeOH-fixed and stained with 0.5% crystal violet for 20 min, followed by counting from six random microscopic fields.

Invasion Assay

Cells were treated as in migration assay, but plated in transwells containing 2 mg/ml Matrigel (BD Biosciences).

Statistical Analyses

Data sets were collected and analyzed using Kaleida-Graph (Synergy Software, Reading, Pa.). Analysis of variance (ANOVA) or Student t-tests were performed using KaleidaGraph. For all experiments, p values <0.05 were considered significant and calculated p values are included on the graphs, in the text, and/or in the figure legends.

Example 10. Pharmacological Activation of Myosin II to Correct Cell Mechanics Defects Current approaches to cancer treatment focus on targeting signal transduction pathways. Here, we develop an alternative system for targeting cell mechanics for the discovery of novel therapeutics. We designed a live-cell, high-throughput chemical screen to identify mechanical modulators. We characterized 4-hydroxyacetophenone (4-HAP), which enhances the cortical localization of the mechanoenzyme myosin II, independent of myosin heavy-chain phosphorylation, thus increasing cellular cortical tension.

To shift cell mechanics, 4-HAP requires myosin II, including its full power stroke. We further demonstrated that invasive pancreatic cancer cells are more deformable than normal pancreatic ductal epithelial cells, a mechanical profile that was partially corrected with 4-HAP, which also decreased the invasion and migration of these cancer cells.

Overall, 4-HAP modifies nonmuscle myosin II-based cell mechanics across phylogeny and disease states and provides proof-of-concept that cell mechanics offers a rich drug target space, allowing for possible corrective modulation of tumor cell behavior.

Carbamate-7 Affects the RacE/14-3-3/Myosin II Pathway

We developed a processing and analysis platform called Cytokinesis Image Processing Analysis Quantification (CIMPAQ), to maximize data collection from a single screen and to perform in-house data analysis. CIMPAQ allows us to analyze high content imaging data to identify cell viability, and cytokinetic and mitotic defects of *Dictyostelium* cells, by respectively counting cells, determining the number of nuclei per cell, and measuring the nuclear size (see FIG. 1A, and FIGS. 9E-9I, and FIG. 10 for a complete description outlining the criteria for CIMPAQ hit identification). To ensure that a full frequency distribution of all of these parameters could be extracted, each sample well contained over 400 cells per time point. This approach led to richer, more statistically relevant data sets over those normally collected for high-throughput screens. We developed and used a nuclear reporter (NLS-tdTomato) that is optimal for live cell imaging in normal growth media over multiple time points, and that allows for the number of nuclei in each cell and nuclear area to be discerned.

Proof-of-principle pilot screens were conducted (FIG. 10; Tables 1 and Table 2) and compared with manual nuclei/cell counts (FIG. 9G). Over 22,000 compounds from the ChemBridge Divert-SET library were screened using CIMPAQ. Approximately 15% of the screened compounds inhibited cell growth and 25 affected cytokinesis. Here, we focus on carbamate-7 (FIG. 2A), treatment with which resulted in an increase in the binucleate to mononucleate ratio, as well as the multinucleate to mononucleate ratio (both indicative of mild cytokinesis inhibition) at six standard deviations over untreated cells (FIG. 2B). A dose sensitivity analysis identified an increase in binucleate cells in the low nM range suggesting late mitotic or early cytokinesis failure, which became particularly evident at 48 hours (FIG. 2C).

To assess whether carbamate-7 affects known cytokinesis pathways, we targeted two spatially distinct modules—one at the equatorial plane of a dividing cell regulated by spindle signals and the mechanosensory system of myosin II/cortexillin I, and the second at the polar cortex regulated by the RacE/14-3-3/Myosin II pathway (Zhou Q et al., 2010). In a chemical-genetic epistasis analyses, we challenged mutant cell lines targeting both modules with carbamate-7. In the kinesin 6 (encoded by the kif12 locus) null cell line, cytokinesis inhibition by carbamate-7 occurred as in WT, suggesting that carbamate-7 affects a parallel cytokinesis pathway independent of the spindle signaling cascade involving kinesin 6. By contrast, carbamate-7 did not increase binucleation or multi-nucleation in myoII and racE null cell lines relative to the untreated controls. These results suggest that carbamate-7 likely works through the RacE/14-3-3/Myosin II pathway (FIG. 2D).

Figure 3A:
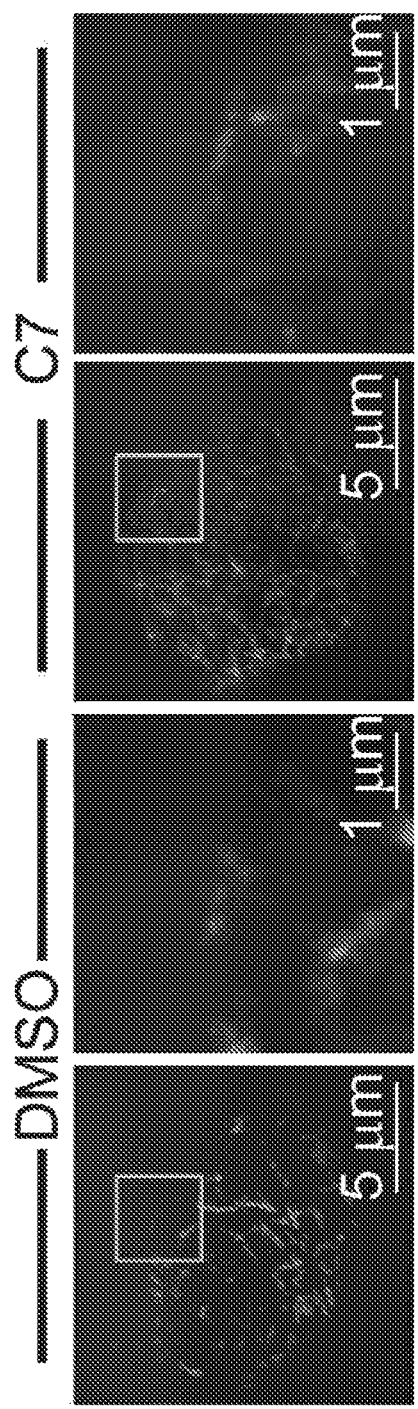
FIG. 3A: Structural Illuminated Micrographs of myoII:GFP myoII cells show an increase in the amount and variability of myosin II bipolar thick filaments in 500-nM carbamate-7 treated (right panels) versus untreated (left panels) cells. In both, the white box represents a zoomed in region, shown to the right of the main images.
Figure 3B:
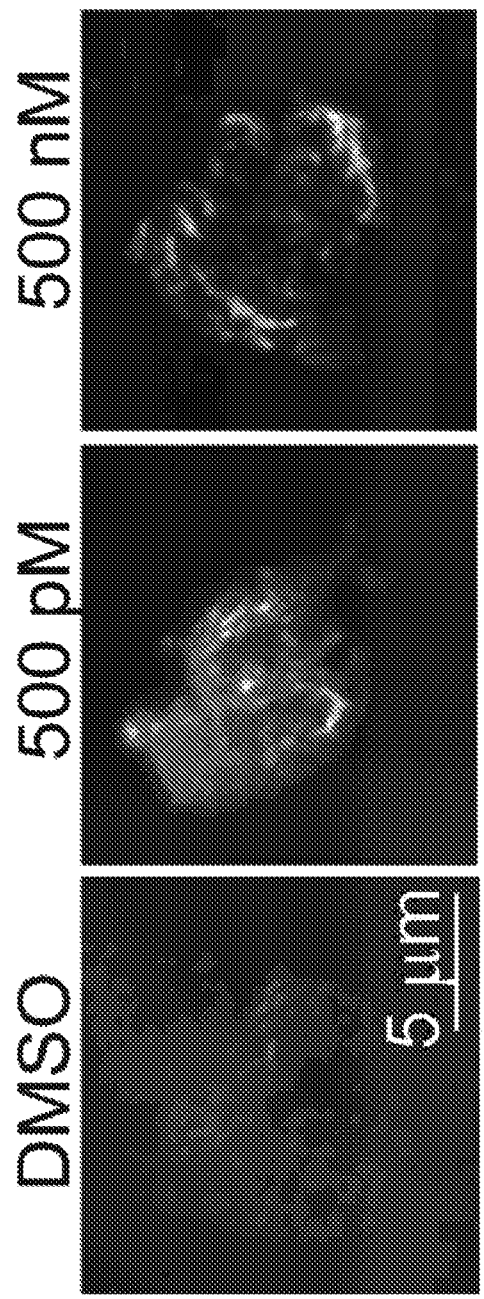
FIG. 3B: Total Internal Reflection Microscopy (TIRF) images of cells treated with increasing amounts of carbamate-7 show increase of cortical GFP-myosin II, quantified in FIG. 3C.
Figure 3C:
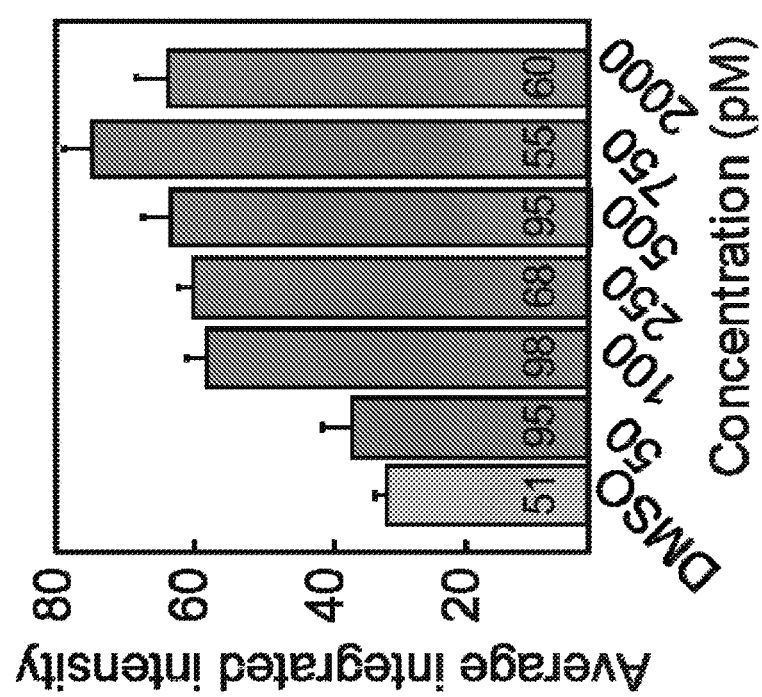
FIG. 3(A-E) area set of images and graphs showing that myosin II cortical dynamics affected by treatment with carbamate-7 according to one embodiment of the present invention.
FIG. 3D: Sedimentation assay shows increase of non-monomeric myosin II in 700-nM carbamate-7 treated over untreated cells (n=3).
FIG. 3E: Cortical tension measurements show a 1.4-fold increase in cells acutely treated with carbamate-7. Error bars represent SEM.
Figure 3D:
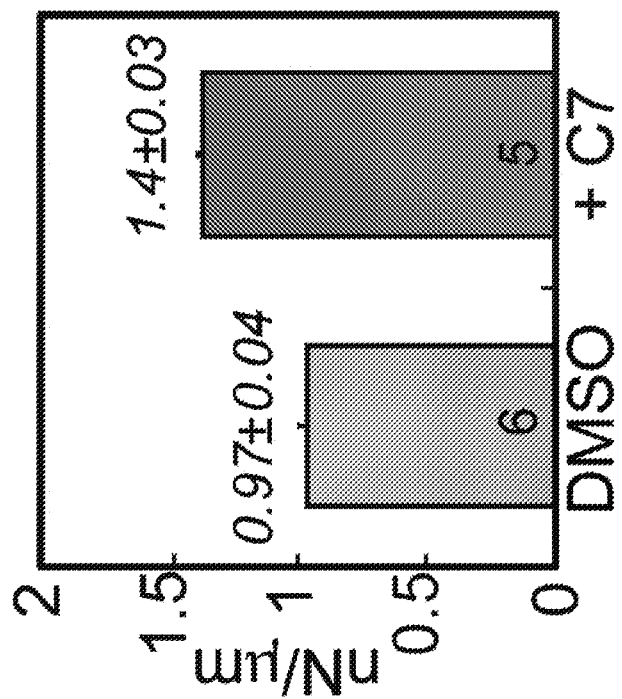
Figure 3E:
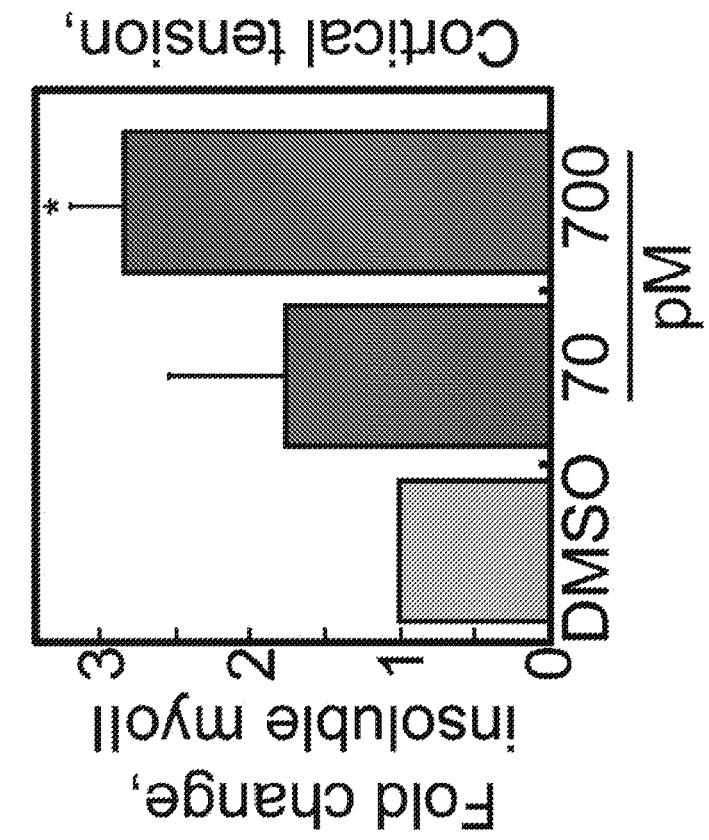

Epifluorescence and Structured Illumination Microscopy (SIM) studies of mCherry-racE and GFP-myosin II in their respective rescued cell lines challenged with carbamate-7 revealed no change in racE localization, but a significant increase in GFPmyosin II cortical accumulation (FIG. 3A). A dose-dependent assessment of carbamate-7 on myosin II localization using Total Internal Reflection Microscopy (TIRF) exposed an increase in the myosin II functional unit, the bipolar thick filament (BTF), at the cortex in the 500 µM range (FIGS. 3B and 3C). These results were corroborated with in vitro sedimentation assays showing an increase in the BTF-containing Triton-X-100-insoluble fraction (FIG. 3D). Because myosin II is a known effector of cell mechanics, both in *Dictyostelium* as well as other organisms (Zhou Q et al., 2010; Reichl E M, et al., 2007; Reichl E M, et al., 2008; Betapudi V, et al., 2006; Betapudi V, et al., 2011; Heisenberg C P, et al., 2013), we next queried whether the increase in cortical localization would impact the mechanical properties of the cell. Using micropipette aspiration (MPA) assays, we determined that acute treatment with 700 µM carbamate-7 led to a 1.4-fold increase in the cell's cortical tension (FIG. 3E), providing direct evidence that our screen successfully identified a modulator of cell mechanics.

Carbamate-7 Chemistry

Figure 4B:
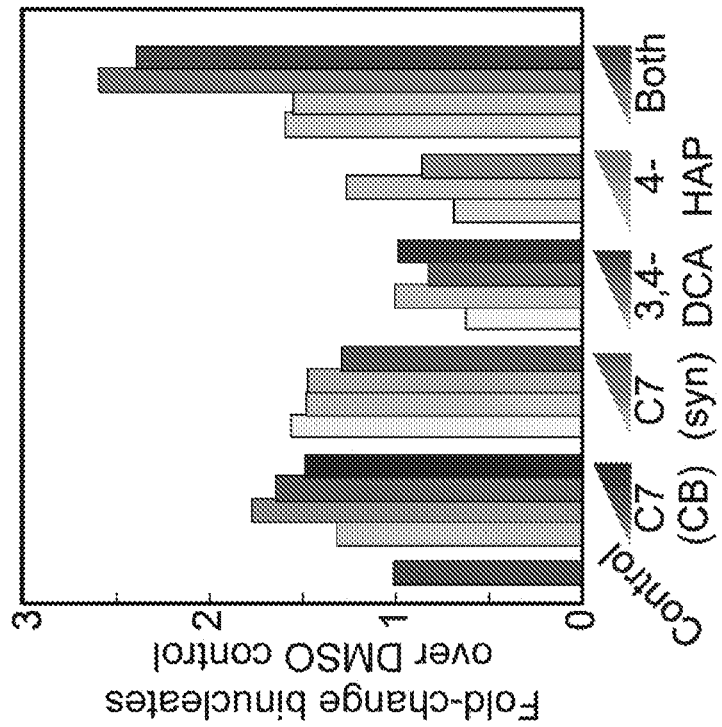
FIG. 4B: Both 3,4-DCA and 4-HAP are required for the shift in binucleation observed from mixtures of carbamate-7 in DMSO, obtained commercially from ChemBridge (CB) and synthesized (syn) in house.
Figure 4A:
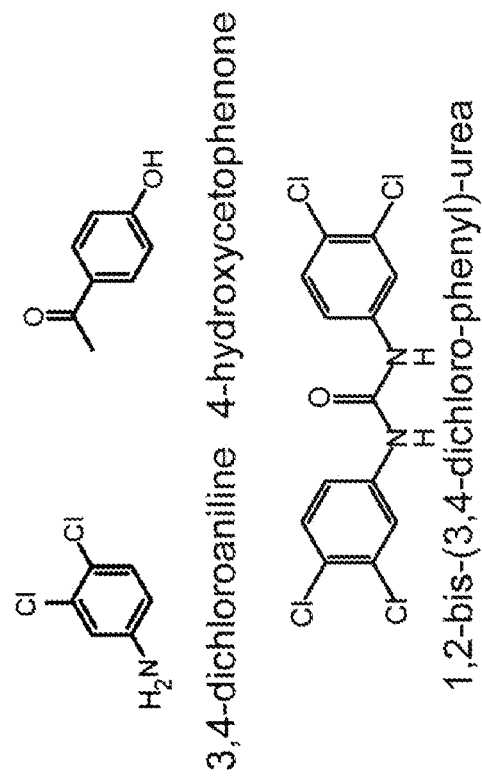
FIG. 4A: Carbamate-7 degrades in DMSO to give three distinct chemical species-3,4-dichloroaniline (3,4-DCA), 4-hydroxacetophenone (4-HAP), and 1,2-bis-(3,4-dichloro-phenyl)-urea.

The hit 5180622 (carbamate-7) was described as 4-acetylphenyl(3,4-dichlorophenyl) carbamate in the ChemBridge Divert-SET library. To validate the identity and activity of the putative carbamate-7, we synthesized and characterized an authentic sample of 4-acetylphenyl(3,4-dichlorophenyl) carbamate from 4-hydroxyacetophenone (4-HAP) and 3,4-dichlorophenyl isocyanate (FIG. 11A). Interestingly, the carbamate was unstable during purification, raising questions about its stability in the ChemBridge Divert-SET library. HPLC analysis to assess the stability of the carbamate in DMSO showed complete conversion of the carbamate to two major products, 3,4-dichloroaniline (3,4-DCA) and 4-hydroxyacetophenone (4-HAP), within 15 minutes (FIG. 11B). N,N'-Bis(3,4-dichlorophenyl)urea also appeared as a minor degradation product in DMSO. Stock solutions of carbamate-7 were subsequently analyzed and found to contain a mixture of 4-HAP, 3,4-DCA and the urea (FIG. 4A). No 4-acetylphenyl(3,4-dichlorophenyl) carbamate could be detected in the commercial stock solutions.

4-HAP Works Through Myosin II

Figure 4C:
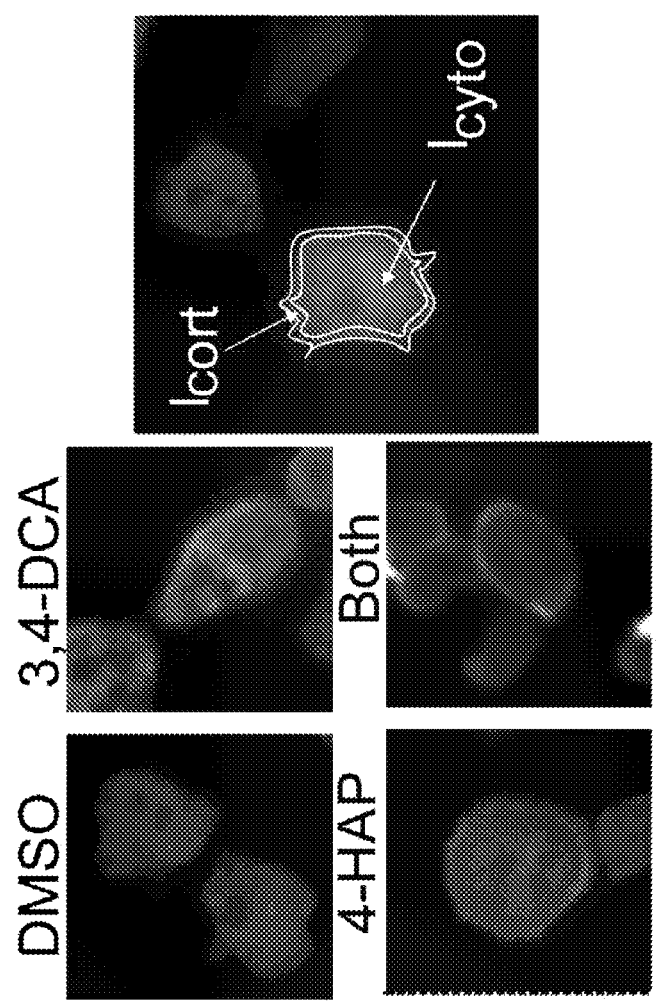
FIG. 4C: Myosin II is enriched at the cortex in 4-HAP and both samples only.
Figure 4D:
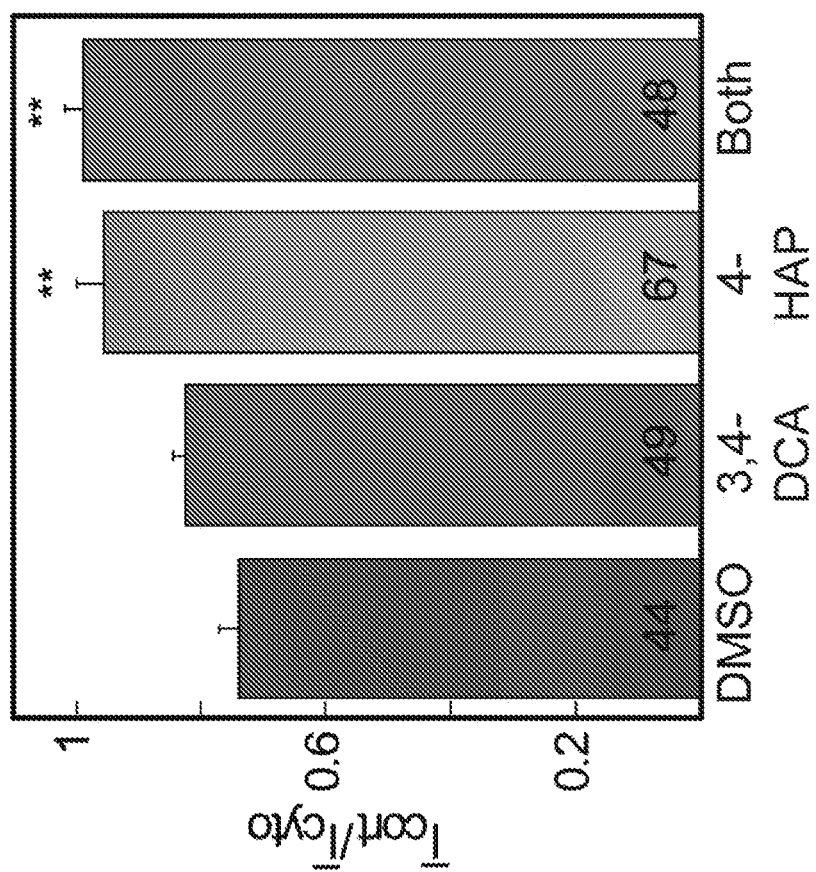
FIG. 4D: Histogram shows the relative myosin II intensities of the cortex to the cytoplasm.
Figure 11D:
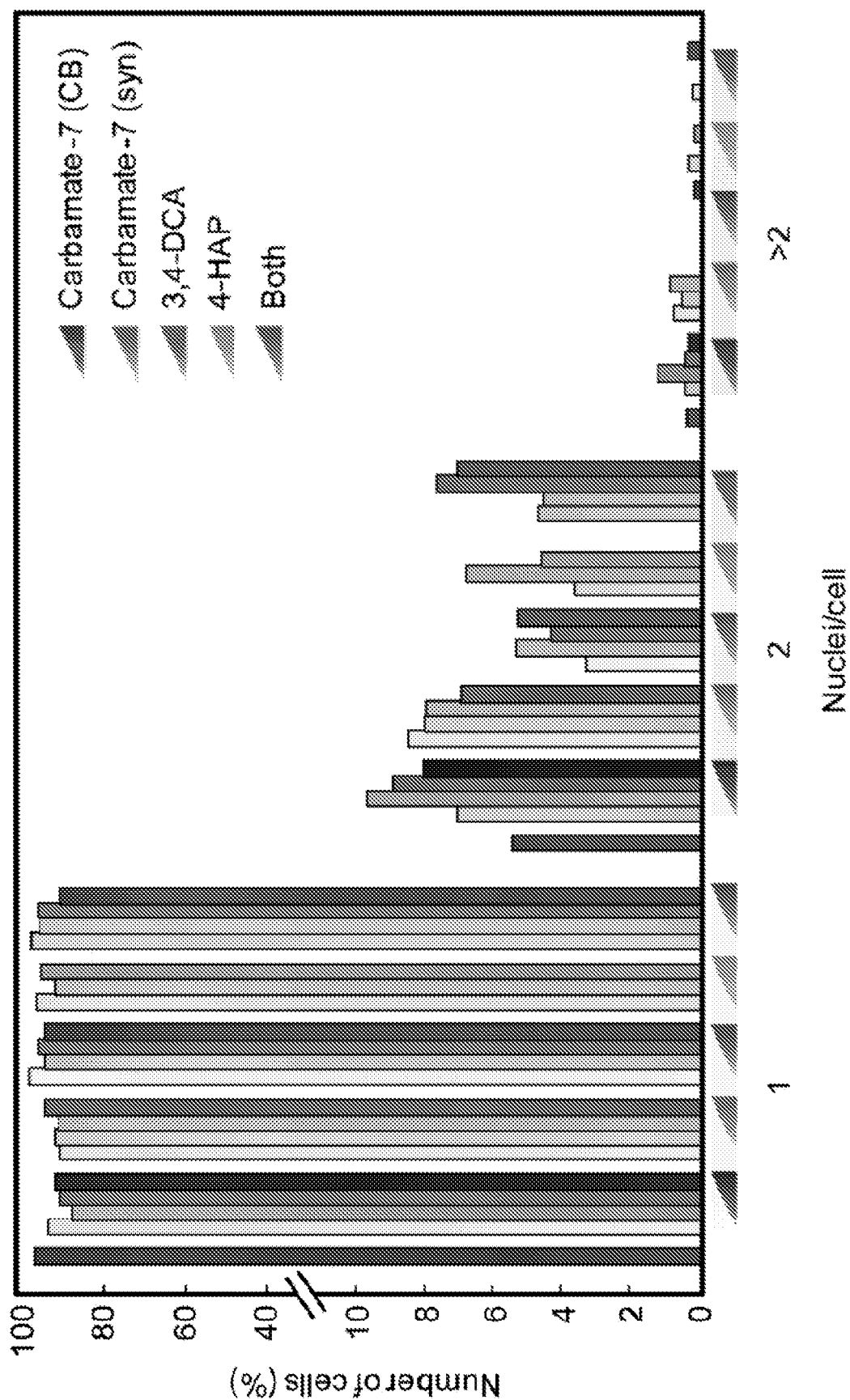
FIG. 11D: Full nuclei per cell distribution of carbamate-7 and breakdown products. 3,4-DCA and 4-HAP together show an increase in binucleates and a decrease in mononucleates, consistent with the results from C-7 treatment (CB: ChemBridge; syn: synthesized). Compound concentrations (nM): 1, 500, 1000, 5000. 5000 nM 4-HAP was lethal and is therefore not shown. n=400-1441 cells/condition.

As the degradation products arising from carbamate-7 appeared to be stable for >24 hours at 22° C., studies were carried out to determine which of these components displayed the biological activity identified above. We show with nuclei/cell distributions over a 500 µM to 5 M concentration range that none of the degradation products alone is sufficient for cytokinesis inhibition, but that a 1:1 combination of 3,4-DCA and 4-HAP increased binucleation 2.5-fold over control cells (FIG. 4B, see FIG. 11D for full curve). We then analyzed the cortical enrichment of myosin II in cells treated with each compound and found that 4-HAP alone drives myosin II relocalization (FIGS. 4C and 4D). These results imply that we have identified a compound combination that works on two separate, yet related pathways involved in cytokinesis.

Figure 4E:
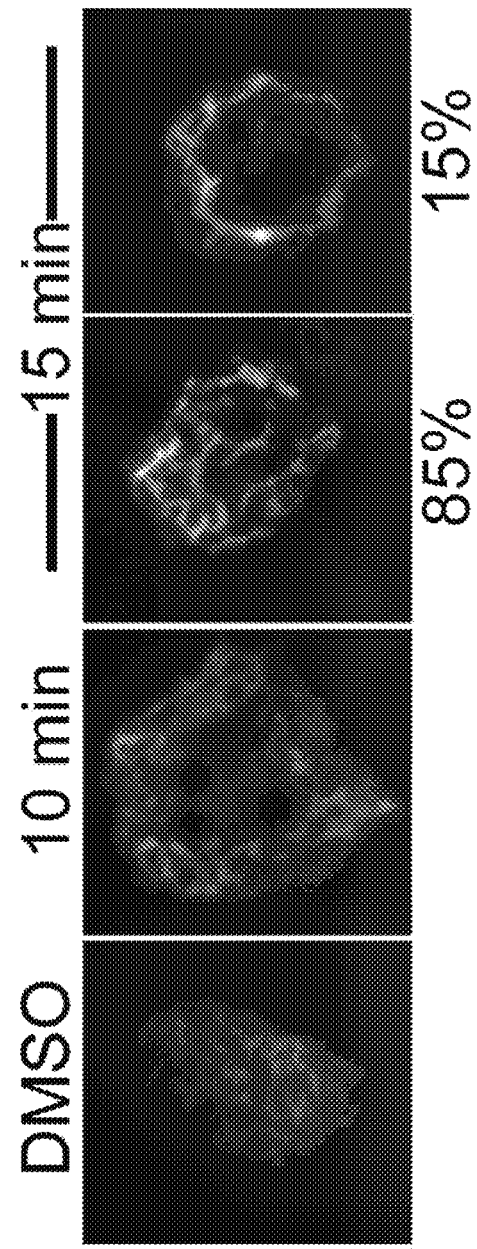
FIG. 4E: TIRF images show an increase in the amount and length of GFP-myosin II BTFs.
Figure 4F:
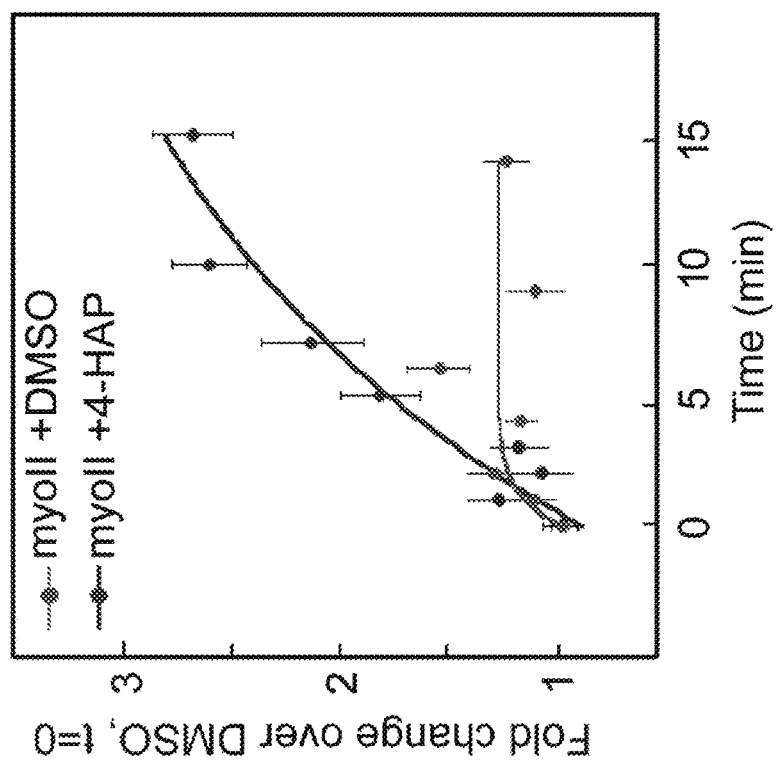
FIG. 4F: 500 nM 4-HAP shows significant localization of GFP-myosin II within 10 minutes of treatment.
Figure 4G:
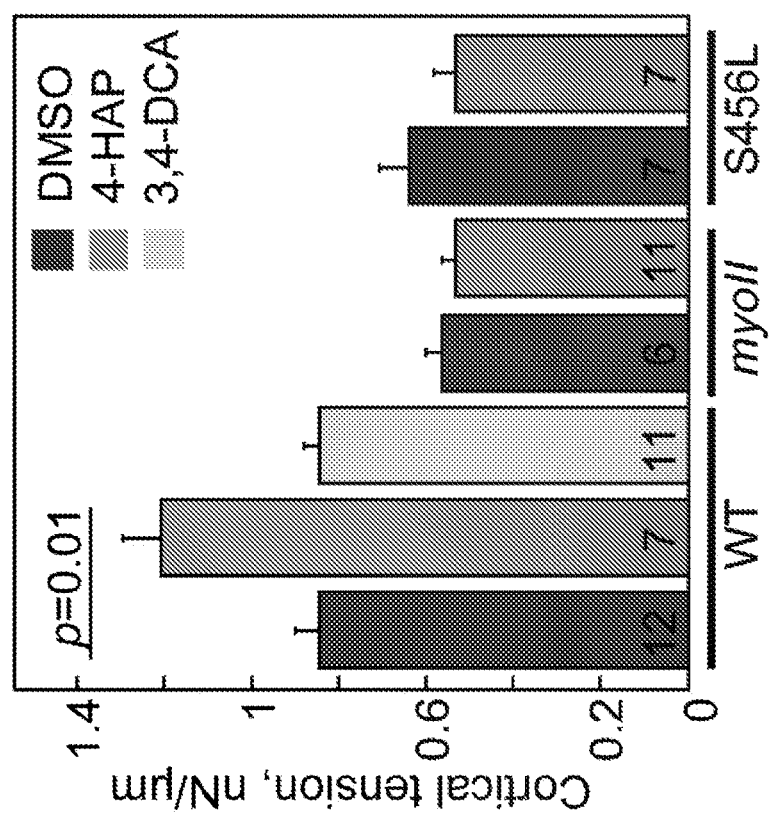
FIG. 4G: There is a 1.5-fold increase in cortical tension of cells acutely treated with 500 nM 4-HAP. The change in effective tension (Teff) is dependent on myosin II. Neither the myoI or S456L myosin cells show an increase in Teff. Error bars represent SEM.
Figure 12A:
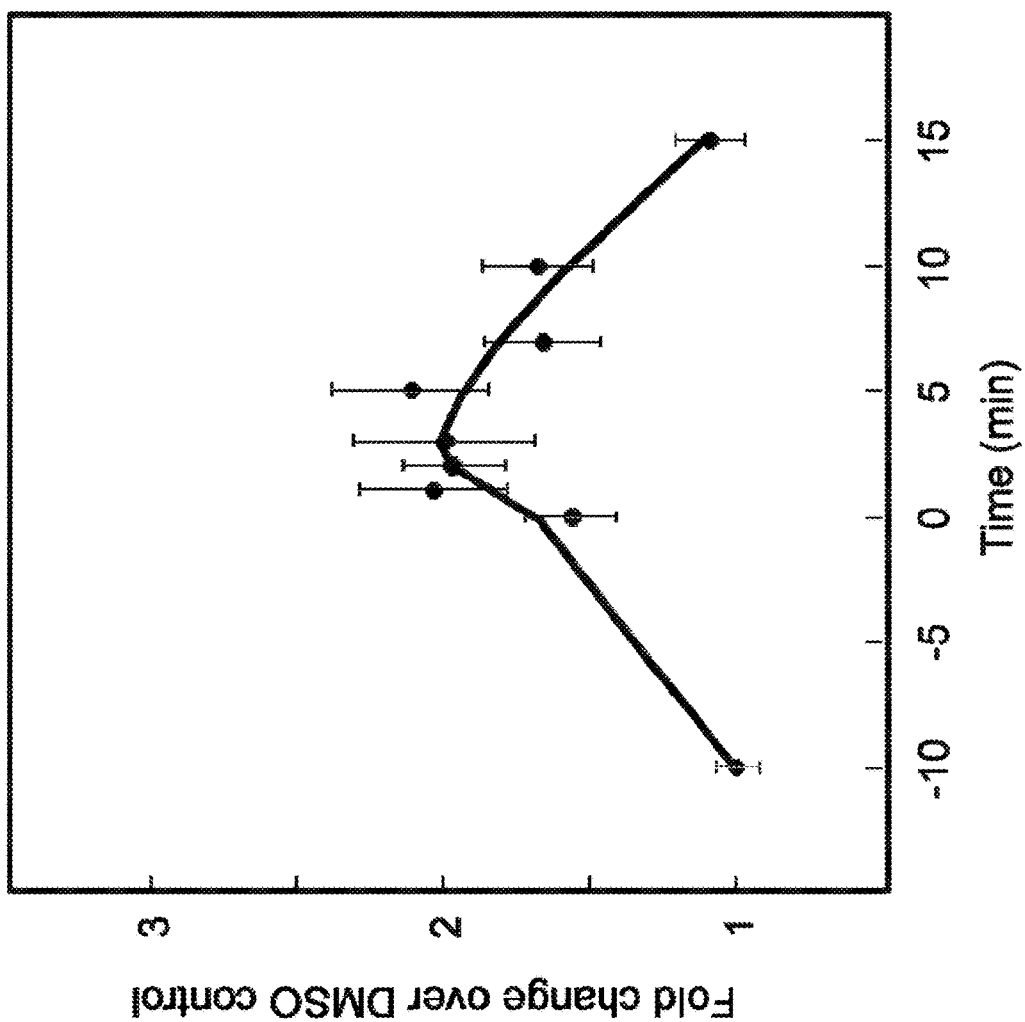
FIG. 12A: Cells treated with 500 nM 4-HAP had a 2-fold increase in myosin II localization at the cortex by TIRF imaging within 10 min. 500 nM 4-HAP was added at t=−10 min. When the 4-HAP-containing media was removed (t=0), myosin II localization reverts to pre-treatment levels within 15 min of removal. n=20-26 cells per time point.
Figure 12B:
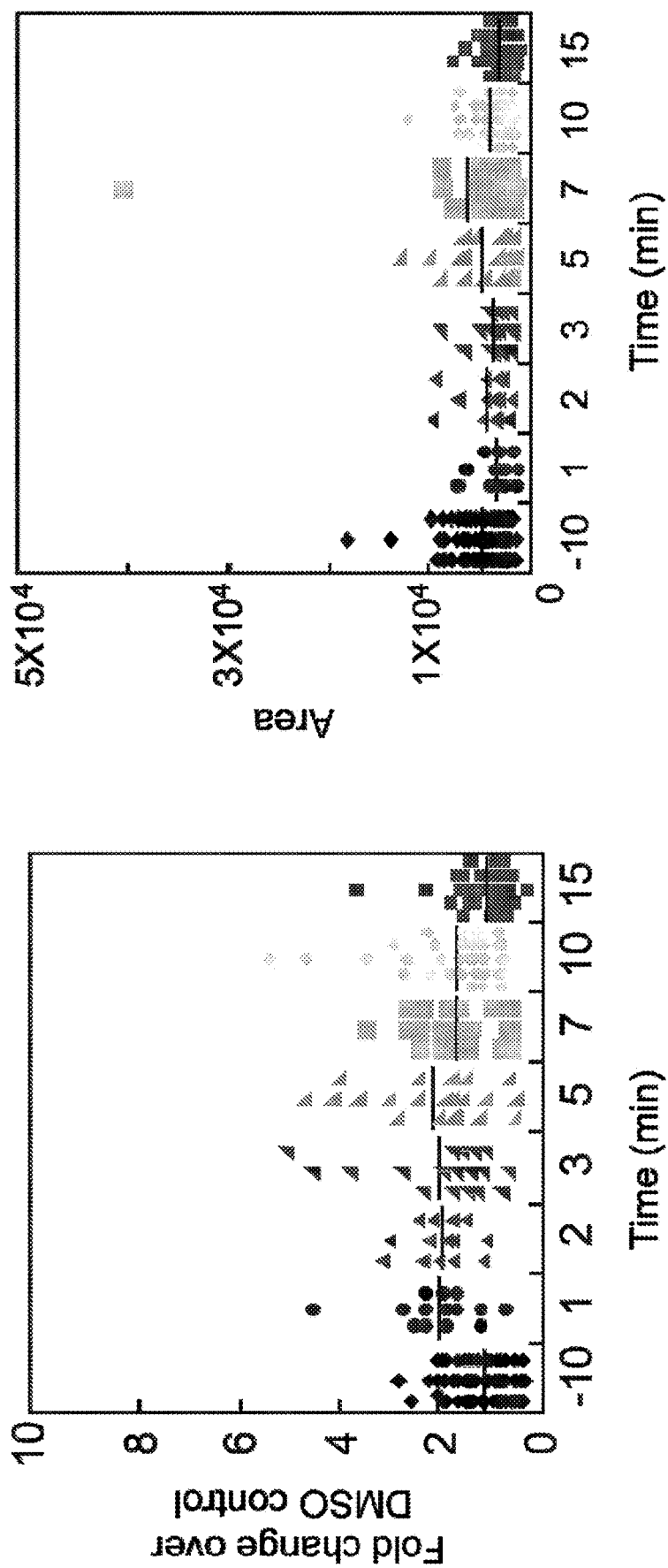
FIG. 12B: Dot plot of the raw data shows the fold-change over the DMSO control at each time point of the washout experiment (left panel), and a dot plot of the raw data of the cell surface contact area for the washout experiments shows no change in surface area among the time points (right panel).

To gauge the time dependency of the myosin II cortical accumulation, we performed time-course experiments using TIRF microscopy. When challenged with 4-HAP, myosin II bipolar thick filaments accumulate at the cortex within 5 minutes, reaching steady state at 15 minutes (FIGS. 4E and 4F). In a majority of cells, the BTF structures increase in length and intensity, while in a subset of cells (15%) they accumulate into ribbon-like rings (FIG. 4E). This 2.5-fold increase in myosin II at the cortex is fully reversible (FIG. 12) and not the result of changes in the contact area of the cells (FIGS. 12 and 13). Neither 3,4-DCA nor the urea result in changes in myosin II cortical distribution (FIG. 13). We next asked if the 4-HAP-induced myosin II shift was responsible for the mechanical changes we previously had observed. WT cells challenged with 4-HAP displayed a 1.4-fold increase in cortical tension compared to untreated cells, while 3,4-DCA had no effect. The change in cortical tension is dependent on myosin II, as myoI null cells did not experience a similar shift in mechanics (FIG. 4G).

Figure 14A:
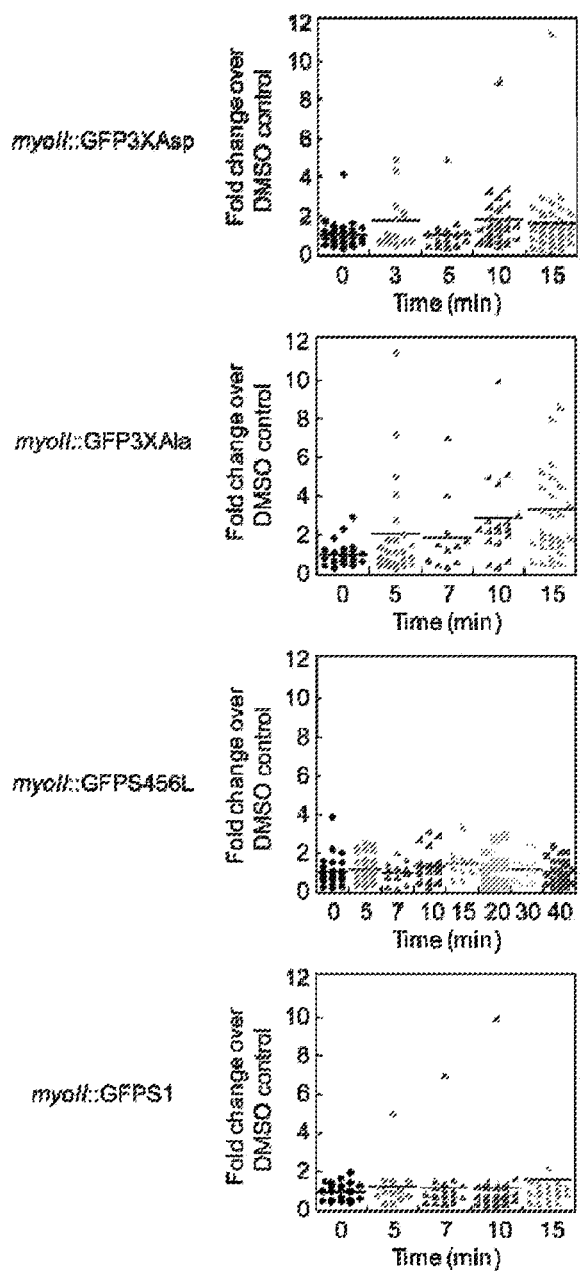
FIG. 14(A-B) are a set of graphs showing quantification of TIRF images which reveal an increase in myosin II localization upon 4-HAP treatment in GFP3XAla and GFP3XAsp expressing cells, but not GFPS456L or GFPS1 expressing cells. (A) Dot plots of the raw data show the fold-increase over the DMSO control for GFP3XAla and GFP3XAsp rescued myoII null cell lines. GFPS456L and GFPS1 show no change in myosin BTF accumulation at the cortex.
FIG. 14B: Dot plots of the raw data of the cell-surface contact area shows no change between time points for all compound treatments.
Figure 14B:
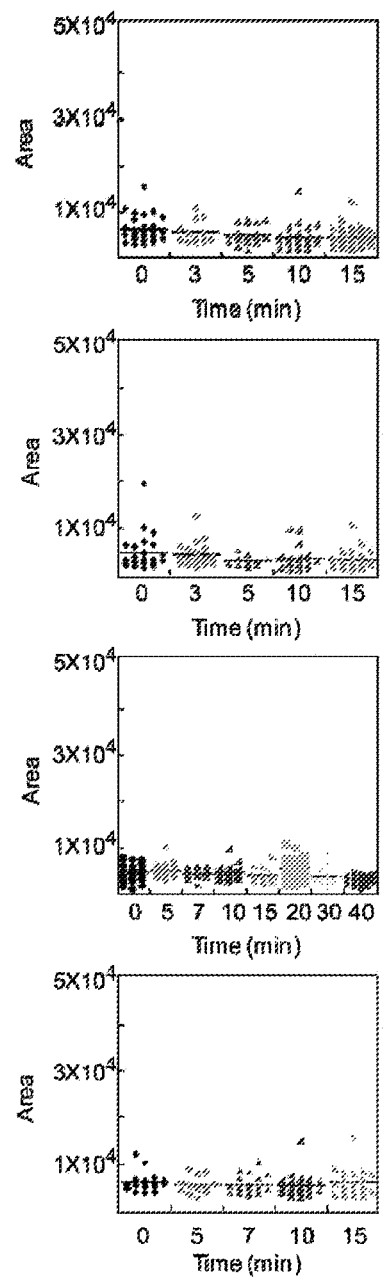
Figure 15A:
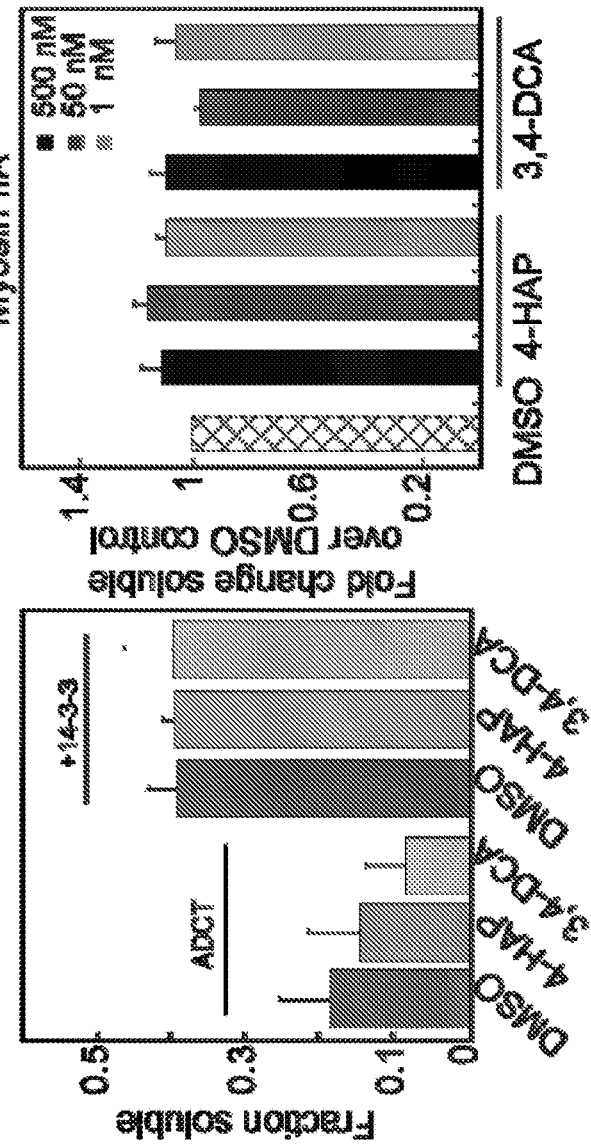
FIG. 15A: Myosin II Dictyostelium ADCT assembly showed no significant change in in vitro assembly with or without purified 14-3-3 in the presence of 3,4-DCA or 4-HAP as compared to the DMSO control (n=6 for DMSO control, n=3 for all others; error bars represent SEM). Mammalian myosin IIA (FIG. 15B) and myosin IIB (FIG. 15C) assembly was unaffected by 3,4-DCA or 4-HAP as compared to DMSO control (n=3; error bars represent SEM).
Figure 15B:
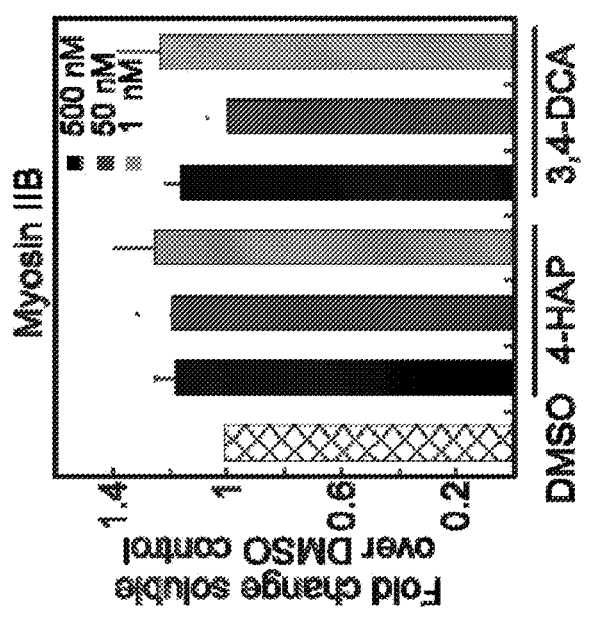
FIG. 15(A-J) are a set of graphs of in vitro assembly and motility assays and PDAC results that when taken together, suggest that 4-HAP requires an intact myosin II cytoskeletal network and is myosin II-paralog specific.
FIG. 15D: In vitro motility assays show no significant effect of 4-HAP or 3,4-DCA on non-muscle myosin IIB velocity. The gliding filament velocity of actin filaments on non-muscle myosin IIB in the presence of 500 nM 4-HAP (n=30), 500 nM 3,4-DCA (n=30), and both compounds in 1:1 ratio (250 nM each, n=60) was measured. A significant change in velocity compared to the DMSO control (n=30, p=0.2-0.4), was not observed.
FIG. 15E: Dot plot of the raw data shows no fold-change over the DMSO control.
FIG. 15F: Dot plot of the raw data of the cell-surface contact area shows no change between time points for compound treatments.
FIG. 15G: 4-HAP decreases the cortical tension of the PDAC A10.7 cells towards a HPDE-like mechanical profile.
FIG. 15H: 4-HAP increases assembled myosin IIC in wild type HPDE cells; n provided on bars; *p=0.04.
FIG. 15I: 4-HAP shows little effect on myosin IIA phosphorylation (phosphor-Ser1943) in either HPDE or ASPC-1 cells; n provided on bars; p=0.17.
FIG. 15J: Viability assay on ASPC-1 cells across five concentrations of 4-HAP (50 nM, 500 nM, 1 M, 5 M, 50 M) shows no difference over DMSO control.
Figure 15C:
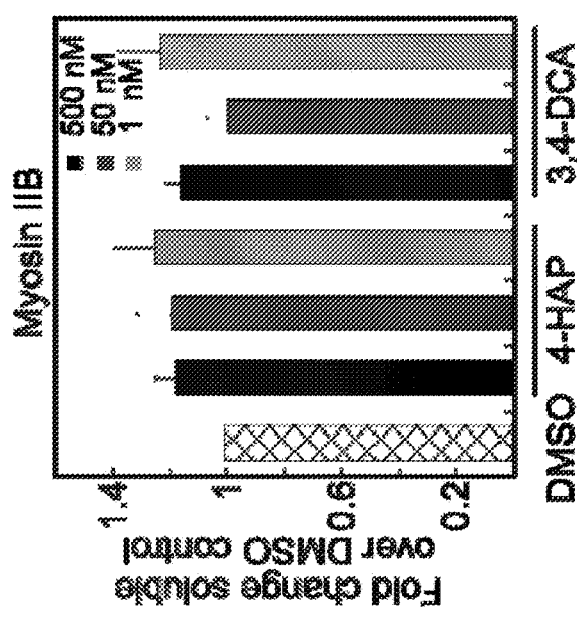

Myosin II BTF formation is regulated by the enzymatic conversion of myosin II monomers from assembly-incompetent to assembly-competent forms resulting in their dimerization and further assembly into functional BTFs (Mahajan R K, et al., 1996; Niederman R, et al., 1975). This conversion is driven by the dephosphorylation of three threonines in the myosin tail of the heavy chain, all of which are C-terminal to the assembly domain (Yumura S, et al., 2005; Egelhoff T T, et al., 1993). To determine if 4-HAP-activation of myosin II impinges on this assembly scheme, we tested the effect of 4-HAP on the in vivo assembly dynamics of the assembly-incompetent, phosphomimic form of myosin (3XAsp), as well as the assembly overcompetent, unphosphorylatable form (3XAla) in myoII null cells (Yumura S, et al., 2005; Egelhoff T T, et al., 1993; Robinson D N, et al., 2002). Both cell lines showed an increase in filament formation compared to their controls at 10 minutes post-treatment, with 3XAsp generating more short filaments, and 3XAla increasing in filament length and intensity (FIGS. 5A and 5B; FIG. 14). To further investigate the role of the assembly domain of myosin in 4-HAP activation, we performed in vitro assembly assays on a myosin II tail fragment, assembly domain-C-terminal (ADCT), which is sufficient to reconstitute regulatable myosin II BTF assembly, as well as tail fragments from human myosin IIA and IIB. These experiments were also conducted in the presence or absence of 14-3-3, a myosin II binding partner that sequesters free myosin monomers, thus increasing the sensitivity of the assembly assay and providing a positive control for a direct effector of myosin II assembly (Zhou Q et al., 2010). In all experimental setups, 4-HAP did not affect the assembly of myosin II, including the human IIA and IIB paralogs (FIGS. 15A, 15B and 15C). These overall results imply that BTF assembly in the presence of 4-HAP is independent of myosin II heavy chain phosphorylation. Therefore, 4-HAP-induced cortical accumulation of myosin BTFs may be caused by alterations to other parts of the myosin recruitment pathway or to the myosin II ATPase cycle.

To test the latter hypothesis, we used the myosin mutant S456L. The S456L mutation disrupts the communication between the motor's ATP-binding pocket and converter domain, resulting in normal ATPase activity but a 10-fold slower actin filament sliding velocity (Murphy C T, et al., 2001). Unlike the assembly-compromised myosin mutants, myoII null cell lines complemented with GFPS456L did not show a response to 4-HAP, even when the time course was extended beyond one hour (FIGS. 5A and 5B; FIG. 14). Additionally, myoII::GFP-S456L cells did not have a change in cortical tension when treated with 4-HAP (FIG. 4G). These data highlight a highly restrictive target space for 4-HAP in the myosin II mechanochemical cycle. Further, the myosin II motor domain alone (subfragment 1-S1) of myosin II did not show an accumulation response to 4-HAP treatment, indicating that 4-HAP's effect requires dimeric myosin II or fully assembled BTFs and was not simply altering the energy state of the cell (FIGS. 5A and 5B). These results indicate that 4-HAP requires the full myosin II power stroke (FIG. 6).

We tested whether 4-HAP could affect the in vitro motility of mammalian myosin IIB and found that 4-HAP did not significantly alter this myosin's motility (FIG. 15D). However, in vitro motility assays only probe the rate-limiting step for motility under no-load conditions. In vivo, myosin II experiences load in the context of a mechanosensory control system anchored in part, by its cooperative interaction with another actin crosslinker cortexillin I (Kee Y S, et al., 2012; Ren Y, et al., 2009). If we interrupt this control system by deleting cortexillin I, 4-HAP-directed myosin II accumulation is also abolished (FIGS. 5A and 5B; FIGS. 15E and 15F). These results reveal that 4-HAP requires normal genetic pathways for myosin II accumulation to occur.

4-HAP Stiffens Pancreatic Cancer Cells and HEK293 Cells, but not HL-60 Cells

Pancreatic intraepithelial neoplasia (PanINs) that progress towards pancreatic ductal adenocarcinoma (PDAC) contain a few key genetic lesions that disproportionately affect key cytoskeletal regulators and players. For example, 95% of PDACs have early activating mutations in Kras, which modulates cell elasticity (Delpu Y, et al., 2011; Sun Q et al., 2014). Early PanINs also upregulate the actin crosslinking protein fascin, while later stages are marked by the upregulation of 14-3-3σ, a regulator of myosin II assembly (Zhou Q et al., 2010; Maitra A, et al., 2003, *Clin Cancer Res*; Maitra A, et al., 2003, *Mod Pathol*). Furthermore, serial analysis of gene expression (SAGE) of numerous pancreatic cancer cell-lines that were compared to normal pancreatic cells (HPDE) revealed alterations in the expression of several regulators of myosin II assembly and contractility (Jones S, et al., 2008). Based on these observations, we hypothesized that PDAC progression might be correlated with changes in cellular mechanics, and furthermore, that if these mechanics are myosin II-driven, they might be restored to normal, healthy mechanical profiles with 4-HAP.

Figure 15I:
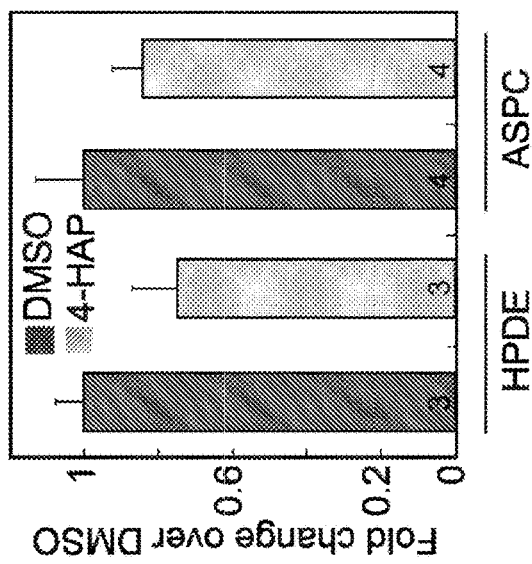
Figure 15H:
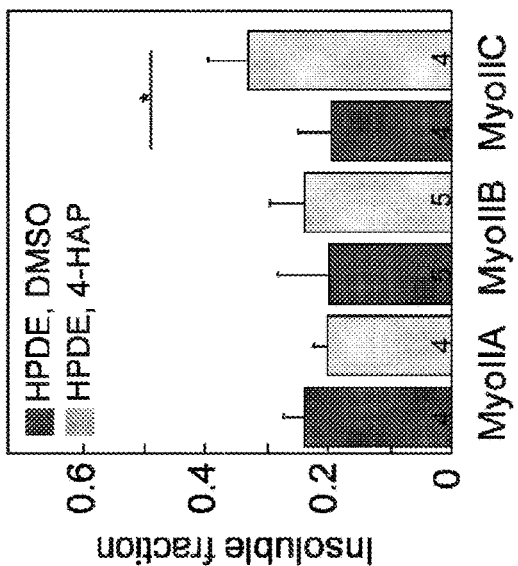
Figure 15G:
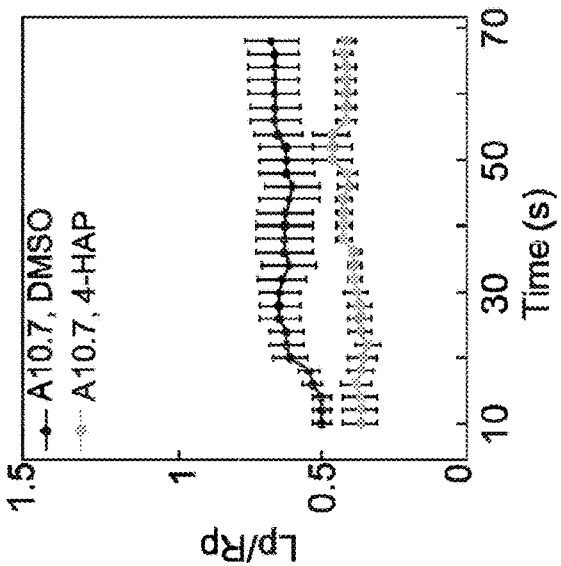
Figure 15J:
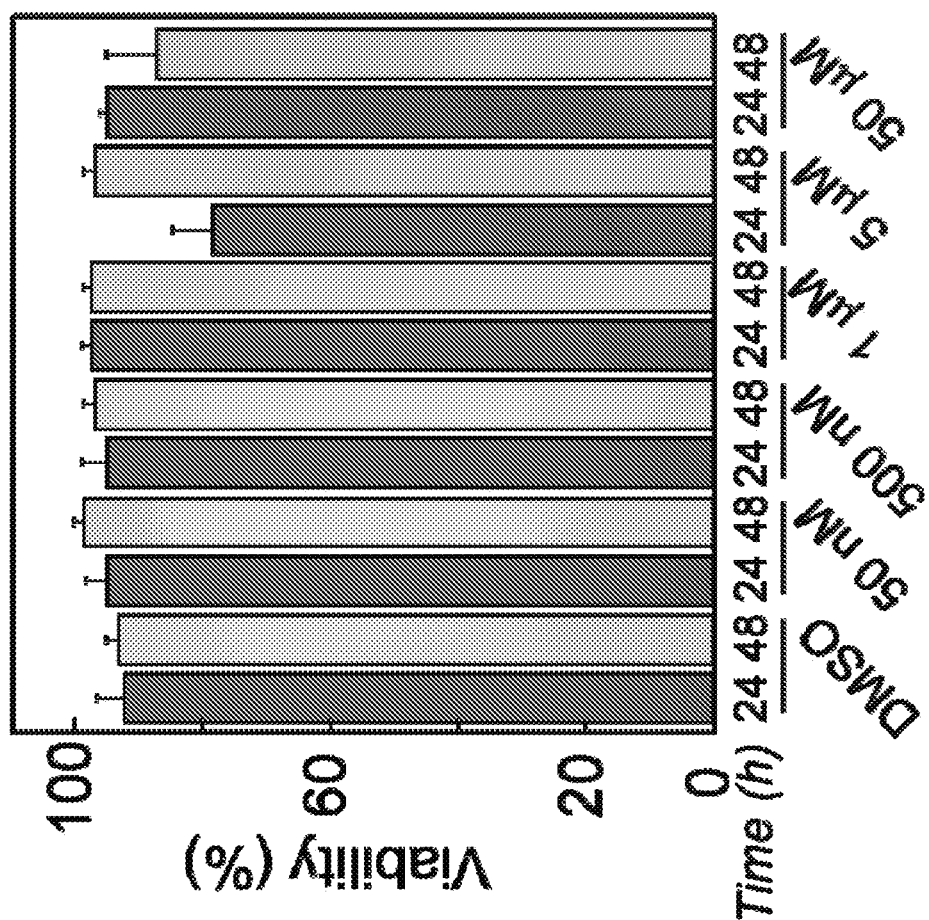

To test this hypothesis, we performed MPA experiments on WT-like human pancreatic duct epithelial (HPDE) cells and two patient-derived Panc cell lines—A10.7, a liver-derived metastatic PDAC cell-line, and the commonly-used ASPC-1, an ascites-derived metastatic PDAC cell-line (Jones S, et al., 2008; Tan M H, et al., 1985). Creep tests demonstrated that these cell lines are mechanically distinct—HPDE cells are significantly stiffer than ASPC-1 or A10.7 cells. The addition of 4-HAP increased the elastic nature of both PDAC cell lines, returning them to an HPDE-like profile (FIGS. 8D and 8E, FIG. 15G). 4-HAP had a similar effect on the widely used human kidney-derived HEK293 cells (FIGS. 8A and 8B). As in *Dictyostelium*, 4-HAP affects myosin II assembly in human-derived cell lines: sedimentation assays showed an increase in myosin IIC BTF formation, while the myosin IIA paralog and the myosin IIA tail phosphosite (phosphor-Ser1943) showed little change (FIGS. 8C and 8F, FIG. 15I). Myosin IIB also showed a shift in assembly in response to 4-HAP, in HEK293 (FIG. 8C) and HPDE (FIG. 15H) cells, while ASPC-1 cells had no detectable myosin IIB. Due to the myosin II paralog specificity of 4-HAP in these cell lines, we next asked whether 4-HAP affects the mechanical profile of HL-60 cells, a human promyelocytic leukemia cell line which solely expresses myosin IIA. 4-HAP did not affect the cortical tension of these cells (FIG. 8G), further implying paralog specificity. 4-HAP had no dose-response effect on ASPC-1 viability (FIG. 15J).

As the initial premise of our original screen was that small molecules that modulate mechanics can affect cancer mechanobehaviors, we tested the invasive capacity of 4-HAP treated cells. ASPC-1 cells treated with 4-HAP show a dose-dependent decrease in in vitro migration and invasion (FIGS. 8H and 8I). These results suggest that the mechanical stiffening triggered by 4-HAP is sufficient to reduce the invasive capacity of metastasis-derived PDAC cells. Collectively, these results demonstrate 4-HAP's ability to alter cellular mechanics across phylogeny and disease states.

DISCUSSION

The behavior and decision making of cells and entire tissues is derived in large part from their mechanical makeup and microenvironment. Cell mechanics define how the cell responds to its microenvironment and how it is able to display behaviors, such as tissue invasion or tumor dissemination. Myosin II has long been ascribed tremendous importance in maintaining the mechanical integrity of cells. As a mechanoenzyme, nonmuscle myosin II is pivotal in an extensive array of normal physiological mechanosensation and mechanotransduction processes, including cell division, adhesion, motility, stem cell differentiation, and tissue morphogenesis. Mutations in myosin II paralogs and myosin II regulatory proteins are associated with a number of diseases, such as the MYH9-related disease cluster (May-Hegglin Anomaly, Epstein Syndrome, and Sebastian Syndrome) (D'Apolito M, et al., 2002; Marini M, et al., 2006; Even-Ram S, et al., 2007).

Increasingly, altered non-muscle myosin II regulation is correlated with tumor progression and metastasis—the upregulation of Kras, 14-3-3, and Rac signaling leads to downregulation of contractile myosin II (Zhou Q et al., 2010; Sun Q et al., 2014; Dupont S, et al., 2011; Calvo F, et al., 2013; Liang S., et al., 2011; Schramek D., 2014; Surcel A, et al., 2010). These changes in expression, often caused by genetic lesions, can provide a mechanical differential, giving precancerous cells an advantage over their neighbors in breast and pancreatic cancer progression (Delpu Y, et al., 2011; Maitra A, et al., 2003, *Clin Cancer Res*; Maitra A, et al., 2003, *Mod Pathol*).

Affecting myosin II activity along the cellular mechanics continuum—whether through a direct disruption of myosin II-cofactor complexes or a shift in the myosin II-actin and actin-binding protein cooperative interactions that respond to mechanical stress (Luo T, et al., 2013; Luo T, et al., 2012)—has enormous therapeutic potential. Here we demonstrate the ability to identify small molecules that affect known mechanosensitive pathways by targeting the mechanical process of cell shape change that occurs during cytokinesis.

We have identified 3,4-dichloroaniline and 4-hydroxyacetophenone, the latter of which alters myosin II-dependent cell mechanics. We further demonstrate that fine-tuning myosin II dynamics can mechanically stiffen pancreatic cancer cell lines towards a more WT mechanical profile, which in turn alters the migration and invasion of these cells (FIGS. 5-6 and 8). Our strategy for identifying and characterizing small molecule modulators has broad implications not just in pancreatic adenocarcinoma, but across cancer cell types characterized by mechanical transitions, such as breast and lung cancers (Sun Q et al., 2014; Cross S E, et al., 2007).

Acetophenones, such as 4-HAP, have been previously identified as the chemical and microbial degradation products for a wide array of industrial and agricultural chemicals (Beynon K I, et al., 1973), such as bisphenol-A (BPA) (Ike M, et al., 2002) and pNP (4-(1-nonyl)phenol), where it is used for growth by some aerobic microorganisms (Vallini G, et al., 2001; Tanihata Y, et al., 2012). In addition, 4-HAP has been isolated from *Cynanchum paniculatum* and *Cynanchum wilfordii* extracts, commonly used for its anti-inflammatory and vascular-protective effects (Choi D H, et al., 2012; Choi D H, et al., 2012; Jiang Y, et al., 2011). It will be of interest to explore the possibility that 4-HAP may impact the mechanics of vascular tissue, as well as to expand upon its ability to alter myosin II dynamics in other mammalian cell types, particularly cancer cells. In addition, carbamate-7, the originally identified compound whose degradation leads to these two main byproducts, is part of a family of compounds, including propham and chlorpropham (CIPC). These compounds have been used widely in herbicides (Dolara P, et al., 1993) and were previously classified as mitotic inhibitors, with demonstrated growth defects and alterations in spindle morphology (Akashi T, et al., 1994; Hepler P K, et al., 1969; Magistrini M., et al., 1980; Oliver J M, et al., 1978; Walker G M., 1982; Clayton L, 1984). While we found that neither 3,4-DCA nor 4-HAP affected microtubule structure, we have previously demonstrated a link between microtubules and the RacE/14-3-3/MyoII pathway (Zhou Q et al., 2010). Our studies on 4-HAP and 3,4-DCA may provide further mechanistic insight into the mode of action of this class of compounds. More importantly, 4-HAP provides an important strategy for modulating cell mechanics and will be of interest to test in a wide range of disease processes, as well as in tissue engineering where cell differentiation may be guided by environmental mechanics.

Example 11. The Identification of 4-HAP's Mechanism of Action and Target Space

While 4-HAP's direct target remains to be identified, 4-HAP appears to work through myosin II as indicated by two key pieces of data. First, 4-HAP increases cortical tension in wild type cells, but not in myosin II null mutant cells (a complete genetic deletion) (FIG. 4G). Second, 4-HAP does not have an effect on the S456L myosin II mutant, thus demonstrating a requirement for the full myosin II step (FIG. 5). Therefore, 4-HAP requires a full working myosin II for its effect on mechanics.

To decipher the requirements of 4-HAP on myosin II, a library of mutant myosin II proteins that affect each of the major aspects of myosin II function was used. 4-HAP's promotion of myosin II cortical localization implied a possible effect on heavy chain phosphorylation regulation of myosin II bipolar thick filament assembly. To test this hypothesis, we used the two genetic mutants that mimic the phosphorylated (3×Asp; poor assembly mutant) and non-phosphorylated (3×Ala; over-assembly mutant) states. 4-HAP still worked on these two mutants, demonstrating that its mechanism is myosin heavy chain phosphorylation-independent (FIG. 5). This result is consistent with considerable published experimental and computational work (e.g., Luo T, et al., 2013; Luo T, et al., 2012).

Having ruled out a direct involvement of heavy chain phosphorylation regulation, we turned to the motor domain. The S1 fragment (motor only) did not respond to 4-HAP. This demonstrated that there is not a global nonspecific effect such as a loss of membrane potential, which would cause the proton pump to stop producing ATP, thus leading the S1 motor to bind actin in the rigor state. Other treatments that deplete the cell of ATP also cause the S1 motor to bind to the cortex, which was not observed with 4-HAP treatment. Further, the S1 mutant data indicate that dimeric myosin II is essential for 4-HAP's effect, which is important for the mechanism of myosin II assembly.

Next, we tested the S456L uncoupler mutant myosin II. This mutation affects an amino acid in the switch II helix, which resides inside the motor domain. This mutant residue disrupts the communication between the ATP-binding pocket and the converter domain of the motor. The consequence of this mutation is that the motor has normal ATPase activity, but uncoupled mechanochemistry. The mutant has been studied in detail for its biochemical kinetic properties and its mechanical properties (Luo T, et al. 2012; Murphy C T, et al., 2001; Reichl E M, et al., 2008; Girard K D, et al., 2006). From these studies, it is known that the S456L myosin has two defects: a short 2-nm step size, which is ¼ of the WT 8-nm step, and a 3-fold longer ADP-bound state than WT myosin II. Because the velocity of a motor is dependent on the step size divided by the strong actin-bound state time (generally dominated by the ADP-bound state under no-force conditions), this motor slides actin filaments at $\frac{1}{10}$ (~$1/(4\times 3)$) of the WT velocity. The S456L mutant is insensitive to 4-HAP (FIG. 5).

This observation is enormously restrictive for what the cellular mechanism of 4-HAP can be. To explain why, we start with a molecular view of what the motor is doing. To begin, ATP binds the myosin II motor, which causes the motor to release from the actin filament. The motor rapidly hydrolyzes the ATP to ADP.Pi, and it is not until the motor encounters an actin filament that it releases the Pi. Upon encountering an actin filament, the motor binds weakly, then tightly as the Pi is released (see FIG. 6 for cartoon). This all happens normally in S456L, which is why its Vmax of ATP hydrolysis is normal. The WT and S456L motors undergo a ~2 nm step, at which point they have reached the isometric state. Here, WT and S456L diverge in what they do. WT extends the power stroke another 6 nm, to complete the full 8 nm step. Consequently, this larger step will lead to a bigger deformation in any compliant elements throughout the motor or bipolar thick filament. However, S456L exits the normal pathway where it does not take any larger step, waits a little longer before letting go of the ADP, ultimately rebinds ATP and releases from the actin filament. Thus, the S456L mutant identifies a very specific place in the myosin II mechanochemical cycle that 4-HAP depends on for its ability to promote myosin II accumulation.

Moving up to the cortical actin network and whole cell, it is now important to consider how S456L works at these hierarchical levels. At the cellular level, S456L acts as though it is an inert, dead myosin II in the context of interphase cells that are not experiencing mechanical stress (Reichl E M, et al., 2008; Girard K D, et al., 2006). However, as soon as a mechanical stress propagates through the network, S456L behaves as though it is a WT myosin motor.

This WT behavior is seen in two scenarios: cytokinesis furrow ingression (Reichl E M, et al., 2008) and when mechanical stress is imposed using aspiration (Ren Y, et al., 2009; Luo T, et al., 2013). Thus, physiological (cytokinesis) and imposed (aspiration) mechanical stresses rescue the activity of this mutant motor. Because S456L can accumulate in response to mechanical stress, it implies that it can sample the isometric, cooperative binding state (Luo T, et al, 2012). Importantly, the force-dependent bond length of WT myosin II is ~1-2 nm, which is similar to S456L's 2 nm step. Thus, 4-HAP must do something that depends on the remaining 6 nm of the WT step. We currently suspect 4-HAP helps stabilize directly or indirectly the stretching of another compliant element in the myosin II tail, which assists in another aspect of thick filament assembly. Applied mechanical stresses are able to stretch this element even if the motor cannot exert enough deformation (S456L short step-size) so long as the motor can enter the cooperative binding state. 4-HAP may then affect this cross-talk between the motor and the tail.

Finally, myosin II accumulation occurs as a result of the function of a control system constructed by two feedback loops (Kee Y S, et al., 2012). The implication is that myosin II cortical accumulation depends on multiple signal inputs, which include biochemical and mechanical signaling that are integrated. If we break this control system at a key point by deleting cortexillin I—a specific membrane anchoring-actin crosslinking protein, which cooperates with myosin II for accumulation in response to mechanical stress (Kee Y S, et al., 2012; Ren Y, et al., 2009; Luo T, et al., 2013)—we also block myosin II accumulation by 4-HAP (FIGS. 5A and 5B; FIG. S9E, F). This result demonstrates that 4-HAP requires an intact control system for myosin II accumulation. If the 4-HAP-directed myosin II accumulation were non-specific, one might expect that the accumulation would be independent of specific known pathways that the cell uses for myosin II accumulation during normal processes like cytokinesis.

Cancer and the Role of Mechanoresponsive Proteins

Altered mechanical states underlie morphological changes concomitant with cancer progression in two major ways. First, mechanical modifications often result from physical changes in the extracellular matrix (ECM) of the stroma and changes in the cellular composition of tumor microenvironments. Second, the intrinsic genetic and proteomic compositions of cancer cells impact their ability to navigate away from primary tumors, traverse mechanically disparate tissue layers, and establish metastatic niches. To respond to and eventually overcome diverse physical landscapes, migrating malignant cells (or collections of cells) must have a robust, adaptable framework. This adaptability is dependent upon the cell's highly dynamic toolbox of mechanoresponsive proteins (defined here as those having the ability to redistribute in response to mechanical stress). This toolbox, along with its regulatory components, collectively constitutes the mechanobiome.

The cell's mechanobiome forms a mechanical continuum with the surrounding tissue and the relatively stiff nucleus to initiate and maintain metastatic motility. These proteins affect cell mechanics by impacting active force generation from actin assembly that pushes outward on the membrane, and myosin II contractility that pulls inward on the membrane. Myosin II contractility depends on other actin cross-linking proteins in the cytoskeletal network, and their cross-talk fine-tunes the deformability and contractility of the cell. The inventors postulate that a cancer cell's invasiveness and metastasis are not driven by increased or decreased deformability per se, but rather by their mechanoresponsive adaptability. When alterations in the expression of these proteins occur, often due to key genetic lesions, these changes in mechanoresponsiveness lead to aberrant cell behavior.

Unsurprisingly, this mechanical network undergoes striking changes in expression during cancer progression, which facilitates the dramatic spatial and temporal reorganization of the cytoskeleton intrinsic in metastasis. Varying protein levels of critical components of the mechanobiome and the broader actin cytoskeleton have been observed in a wide range of cancers. In addition, major cancer drivers and signaling proteins also have altered expression patterns and additionally impact cell mechanics. Yes-Associated Protein (YAP), whose overexpression is associated with numerous cancers, modulates cellular actin architecture and nonmuscle myosin II regulatory light chain expression and phosphorylation, in turn affecting mechanical parameters, specifically cortical tension and deformability. Early activating KRAS mutations that occur in over 90% of pancreatic cancers, as well as at high rates in colorectal and lung cancers, lead to increased deformability and altered contractility. Overexpression of members of the 14-3-3 family is negatively correlated with prognosis for glioblastoma and liver, pancreatic, and lung cancer patients. While 14-3-3 proteins are involved in numerous biological processes, they also modulate nonmuscle myosin II bipolar filament assembly and cell mechanics (Add new West-Foyle JBC Reference here PMID: 29549125). Furthermore, a key inhibitor of myosin II, the myosin light chain phosphatase subunit MYPT1, is highly upregulated in pancreatic cancer. Here the inventors test the concept that the upregulation of mechanoresponsive proteins may be harnessed for small molecule manipulation with the goal of returning the invasive cell to a healthier stable state. To accomplish this, the inventors first demonstrate that mechanoresponsive proteins are upregulated in patient-derived pancreatic cancer tissue samples and cell lines, and that these proteins directly impact cell mechanics. The inventors show that altered pancreatic ductal adenocarcinoma cancer (PDAC) mechanics emanate in part from a changing ratio of nonmuscle myosin IIs, wherein myosin IIA and IIC are upregulated and myosin IIB is downregulated. The inventors quantify the concentration of nonmuscle myosin paralogs in pancreatic cancer cells, and find that despite its relatively low concentration, myosin IIC has a significant impact on single cell behavior and collective behavior in tissue spheroids. The inventors then test whether an upregulated mechanoresponsive protein can be used as a pharmacological target, by using a small molecule mechanical modulator, 4-hydroxyacetophenone (4-HAP), which the inventors have discovered increases the assembly of myosin IIC and stiffens PDAC cells. The inventors find that 4-HAP induces cortical actin belts and increases transverse actin arcs in single cells and tissue spheroids in a myosin IIC-dependent manner. This 4-HAP-induced change in cytoskeletal structure and mechanics leads to a decrease in PDAC metastasis in a mouse hemi-splenectomy model. Thus, the inventors demonstrate that specifically targeting mechanoresponsive proteins by increasing their activity (in this case by promoting myosin IIC assembly), has therapeutic potential for patients.

Mechanoresponsive Machinery is Upregulated in Pancreatic Cancer

Figures 16A, 16B:
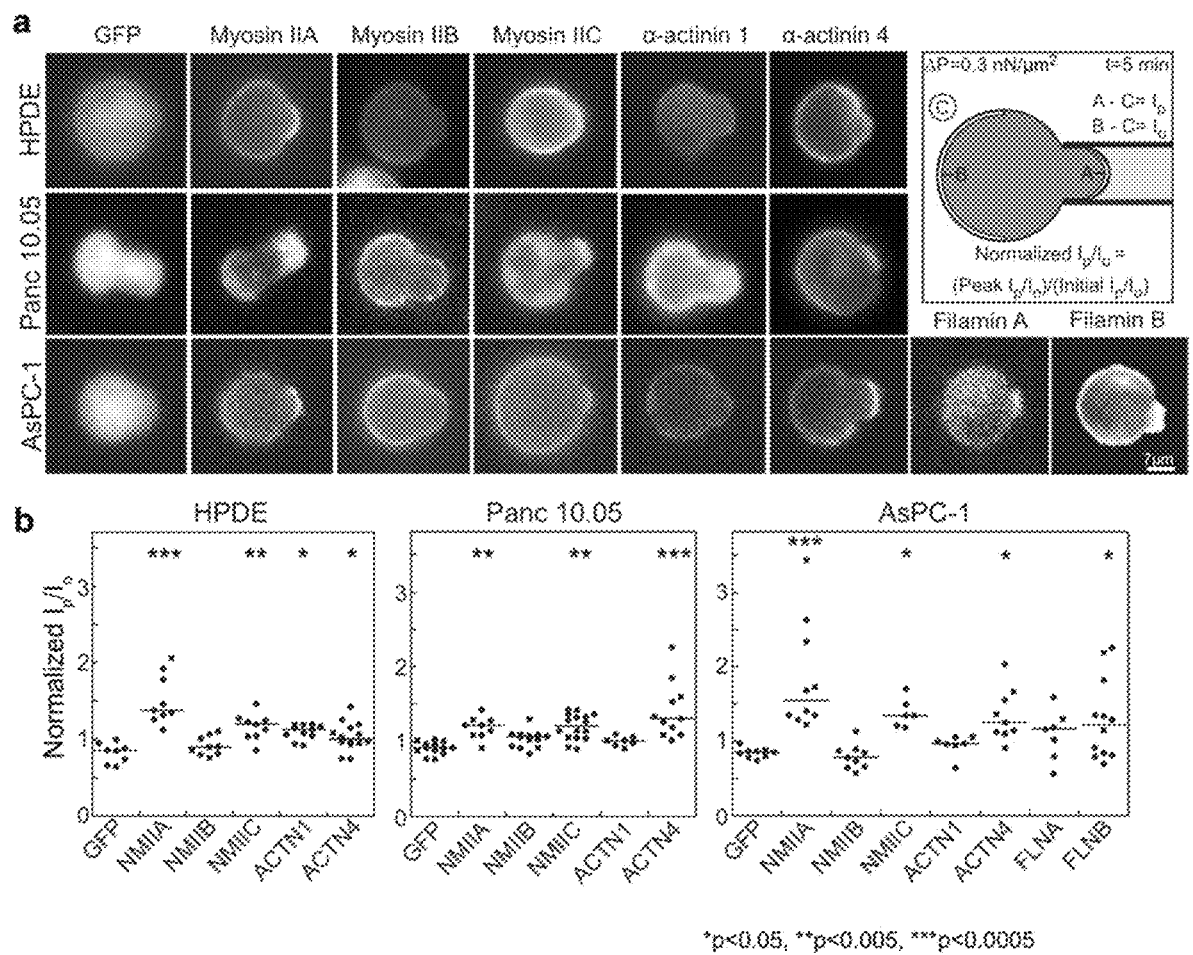
FIG. 16(A-B) Nonmuscle myosin IIA, myosin IIC, α-actinin 4, and filamin B show mechanoresponsiveness in pancreatic cancer cells. (a) Representative images across HPDE, Panc10.05, and AsPC-1 cell lines of the maximum accumulation of GFP alone, GFP-labeled myosin Is α-actinin 4, filamin A, and filamin B, and mCherry-α-actinin 1, show peak intensity after applied stress in MPA mechanoresponse experiments. Scale bar, 7 µm. (b) Quantification of mechanoresponsiveness normalized as a ratio of fluorescence intensity at the tip ($I_p$) to the intensity at the opposite cortex ($I_0$). Medians plotted; *p<0.05, p<0.005, *p<0.0005.

Using the social amoeba *Dictyostelium discoideum*, the inventors previously identified ten mechanoresponsive proteins from a survey of ~35 proteins that accumulate in varying degrees to externally applied mechanical pressure. Of these ten, the inventors developed the physical theory with mathematical models to explain the accumulation of three critical structural elements across phylogeny—nonmuscle myosin II, α-actinin, and filamin. The inventors' theory also predicted which paralogs of these proteins found in mammals were mechanoresponsive. To determine if these mechanoresponsive proteins behave similarly in human disease, the inventors assessed their localization in response to applied external stress via micropipette aspiration (MPA) in pancreatic cancer cells (FIG. 16). Myosin IIA (MYH9), IIB (MYH10), and IIC (MYH14), as well as the actin cross-linkers α-actinin 1 (ACTN1), α-actinin 4 (ACTN4), filamin A (FLNA), and filamin B (FLNB) were transiently expressed in several cell lines. These human-derived lines included HPDE (immortalized Human Pancreatic Ductal Epithelial cells), Panc10.05 (stage II pancreatic adenocarcinoma-derived), and AsPC-1 (stage IV ascites-metastasis-derived) (FIG. 16a). Cells were deformed for five minutes at a pressure of 0.3 nN/µm$^2$, and the maximal protein accumulation in response to the dilational deformation at the aspirated tip of the cell was quantified by normalizing the fluorescence intensity at the tip region ($I_p$) to the unstressed cortex opposite of the pipette ($I_o$) (FIG. 16b).

In all cell lines, compared to the GFP-vector control, myosin IIA and myosin IIC were mechanoresponsive, whereas myosin IIB showed no accumulation, consistent with its previously observed cell-type-specific mechanoresponsiveness. Of the α-actinins, α-actinin 4, but not α-actinin 1, was mechanoresponsive, especially in Panc10.05 and AsPC-1 cells. This differential behavior between the α-actinin paralogs likely results from the much lower actin binding affinity of the actin binding domain of α-actinin 4 ($K_d$=32 µM) compared to that of α-actinin 1 ($K_d$=0.36 µM). This affinity differential leads to a more dynamic α-actinin 4 behavior that is necessary for the protein to respond to mechanical stress. As we predicted, the scenario for filamins differs with regard to actin binding affinity because cooperativity now plays a role. In this case, filamin B ($K_d$=7 M) showed a strong mechanoresponse while filamin A ($K_d$=17 µM) did not (FIG. 16).

The inventors hypothesized that concomitant with cancer initiation and progression, the mechanoresponsive machinery is upregulated to endow cells with the ability to sense and respond to changing physical environments across discrete tissue types. To test this idea, the inventors performed immunohistochemistry on pancreatic cancer tissue samples from 20 patients across all seven proteins—the three non-muscle myosin IIs (IIA, IIB, and IIC), the two α-actinins (1 and 4), and the two filamins (A and B). The inventors compared normal ducts with cancerous ducts and metastatic lesions. In addition, the inventors derived a scoring system that allowed them to delineate between high expression and low expression, as well as percentage of cells positively stained within the quantified ducts (outlined in FIG. 23a). All mechanoresponsive proteins showed a significant shift and increase in expression in cancerous versus normal ducts (FIG. 17, FIG. 23b). Myosin IIA and myosin IIC increased expression, with myosin IIC specifically upregulated in the adenocarcinoma, while myosin IIA increased across the pancreatic cancer stroma in addition to the ducts. The non-mechanoresponsive myosin IIB showed no significant change in expression, with very little staining in general. The mechanoresponsive α-actinin 4 also increased in expression concurrent with cancer progression, while α-actinin 1 maintained mostly uniform expression levels across ducts. Filamin B, which is also highly mechanoresponsive, is upregulated specifically in cancerous ducts. In contrast, filamin A, which is much less mechanoresponsive, is upregulated across the entire pancreatic tissue. These patterns are also noted in non-invasive lesions, termed pancreatic intraepithelial neoplasia (PanINs) (FIG. 23b), with increasing expression associated with cancer progression. Our results are largely in keeping with normal versus pancreatic cancer tissue datasets in the Gene Expression Omnibus (GEO) (FIG. 23c). The staining patterns are also consistent with the Human Protein Atlas which tracks RNA and immunohistochemistry and which suggests that filamin B and α-actinin 4 are poor prognostic indicators for pancreatic cancer patients. Filamin A shows variable PDAC expression across these studies, and α-actinin 1 displays high staining in both normal and cancerous cells. Overall, the immunohistochemistry data indicate that, as a unit, the mechanoresponsive machinery is upregulated in the pancreatic ductal adenocarcinoma of patients.

PDAC Cell Lines can be Used as a Mechanoresponsive Model for PDAC

Figures 17A, 17B:
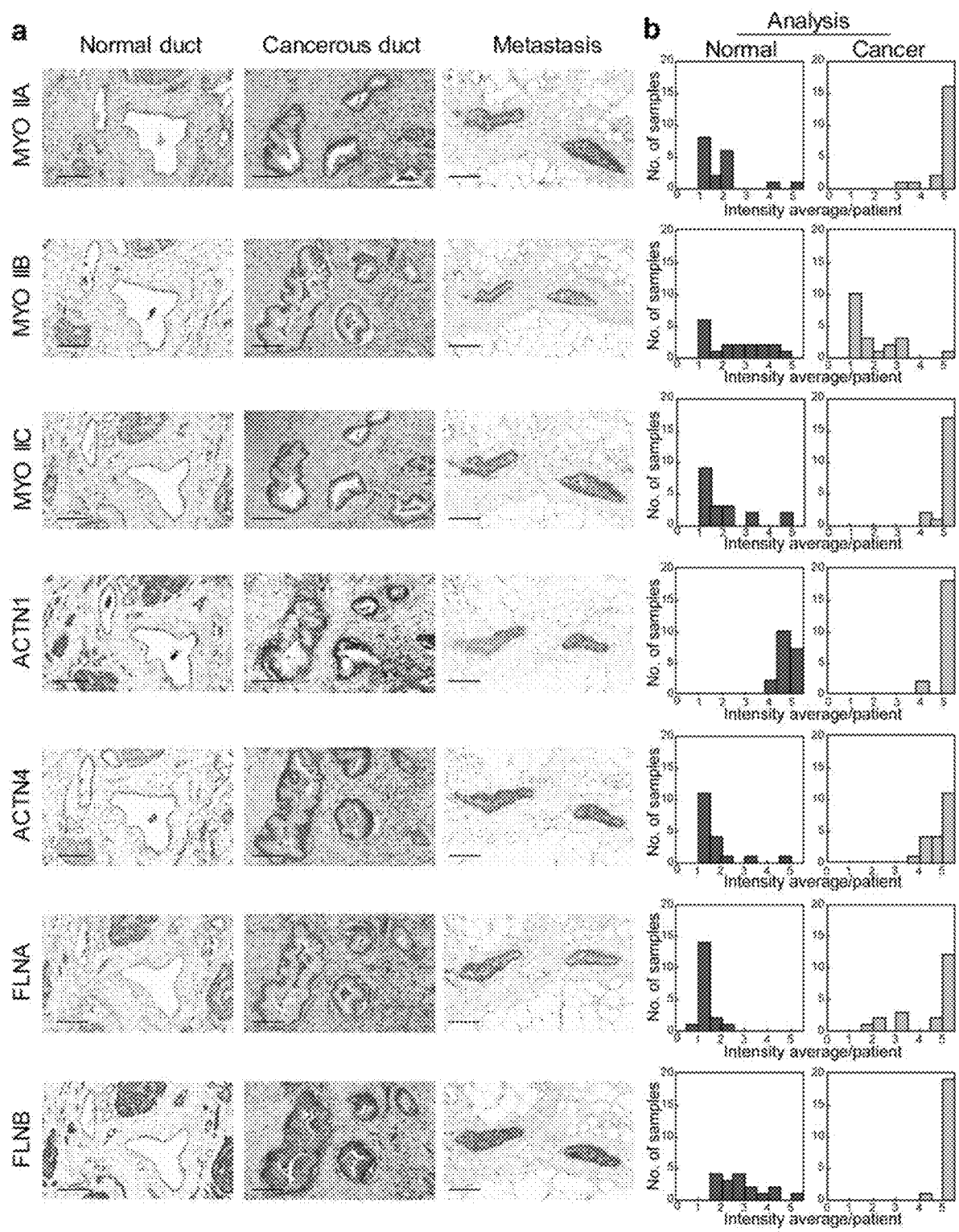
FIG. 17(A-B) The mechanoresponsive machinery is elevated in pancreatic ductal adenocarcinoma in human pancreatic tissue. (a) Immunohistochemistry staining of pancreatic tissue from PDAC patients shows an increase in mechanoresponsive proteins nonmuscle myosin IIA and IIC, α-actinin 4, and both filamin A and B. Scale bar=100 m. For each sample—normal duct, cancerous duct, and metastatic lesion—the same site is shown across all seven antibodies stained. In addition, both the normal and cancerous ducts are from the same patient. (b) Quantification of staining intensity and surface area across 20 patients illustrate dynamic up-regulation and shift of mechanoresponsive proteins, as well as filamin A. Data is plotted as a histogram of the intensity average per patient (described in FIG. 22a and Materials and Methods) across the study group.
Figures 18A, 18B, 18C, 18D:
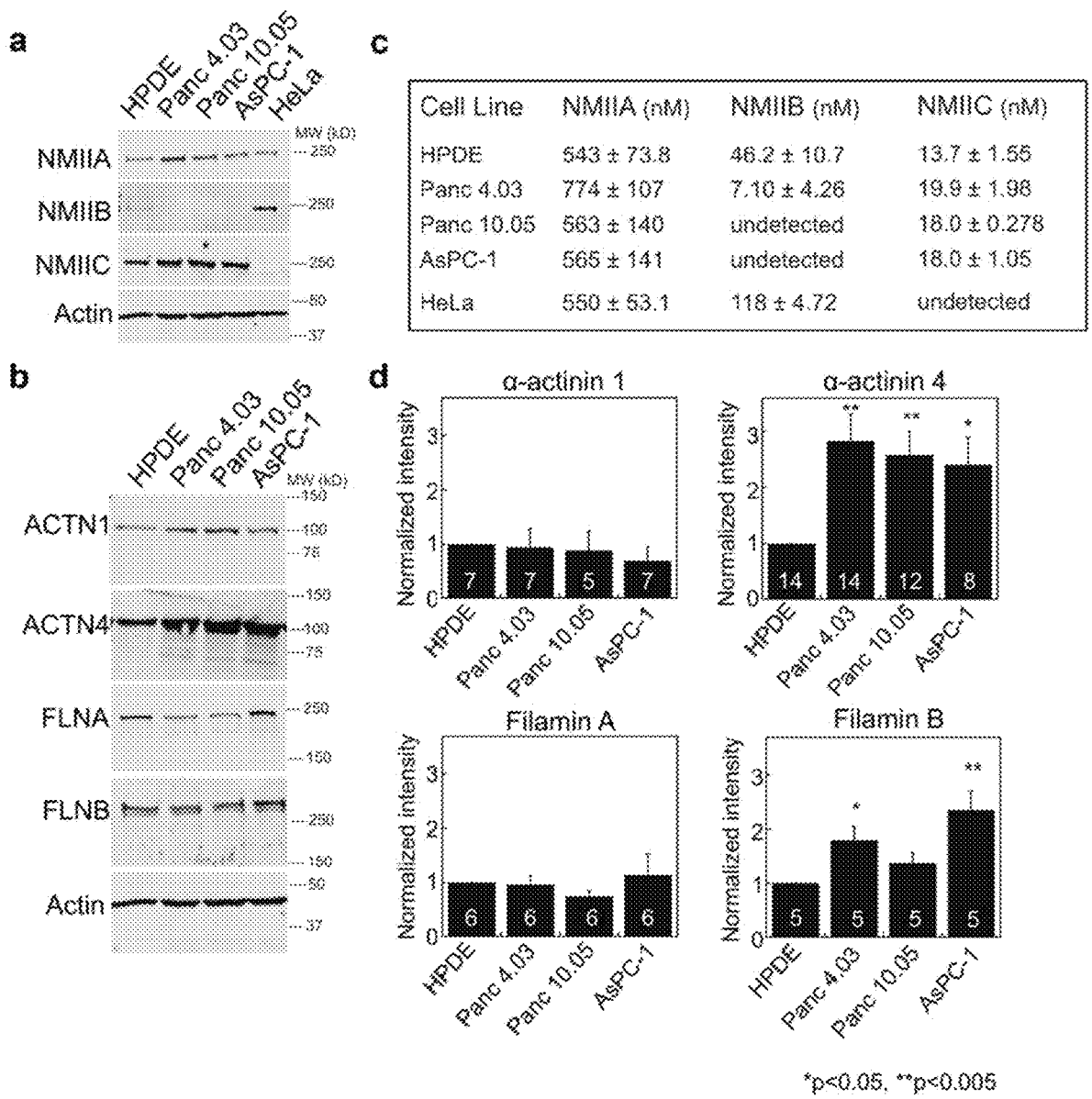
FIG. 18(A-D) Mechanoresponsive proteins increase in pancreatic cancer-derived cell lines. (A) Expression of myosin IIA (NMIIA), myosin IIB (NMIIB), myosin IIC (NMIIC), and actin in HPDE (normal pancreatic ductal epithelium), Panc4.03 (stage II primary tumor), Panc10.05 (stage II primary tumor), and AsPC-1 (stage IV ascites metastasis) cells, compared with HeLa lysate for the purposes of quantification. NMIIA and NMIIC increase in expression, while NMIIB decreases in expression in cancer cell lines. (B) Quantification of the cellular concentration of each myosin II paralog. (C) Expression of alpha-actinin 4 (ACTN4) and filamin B (FLNB) increase, while expression of alpha-actinin 1 (ACTN1) and filamin A (FLNA) do not change in cancer cell lines. (D) Quantification of western blots, examples shown in (c), where numbers on the bars indicate n-values. *$p<0.05$, **$p<0.005$.
Figures 24A, 24B, 24C, 24D, 24E:
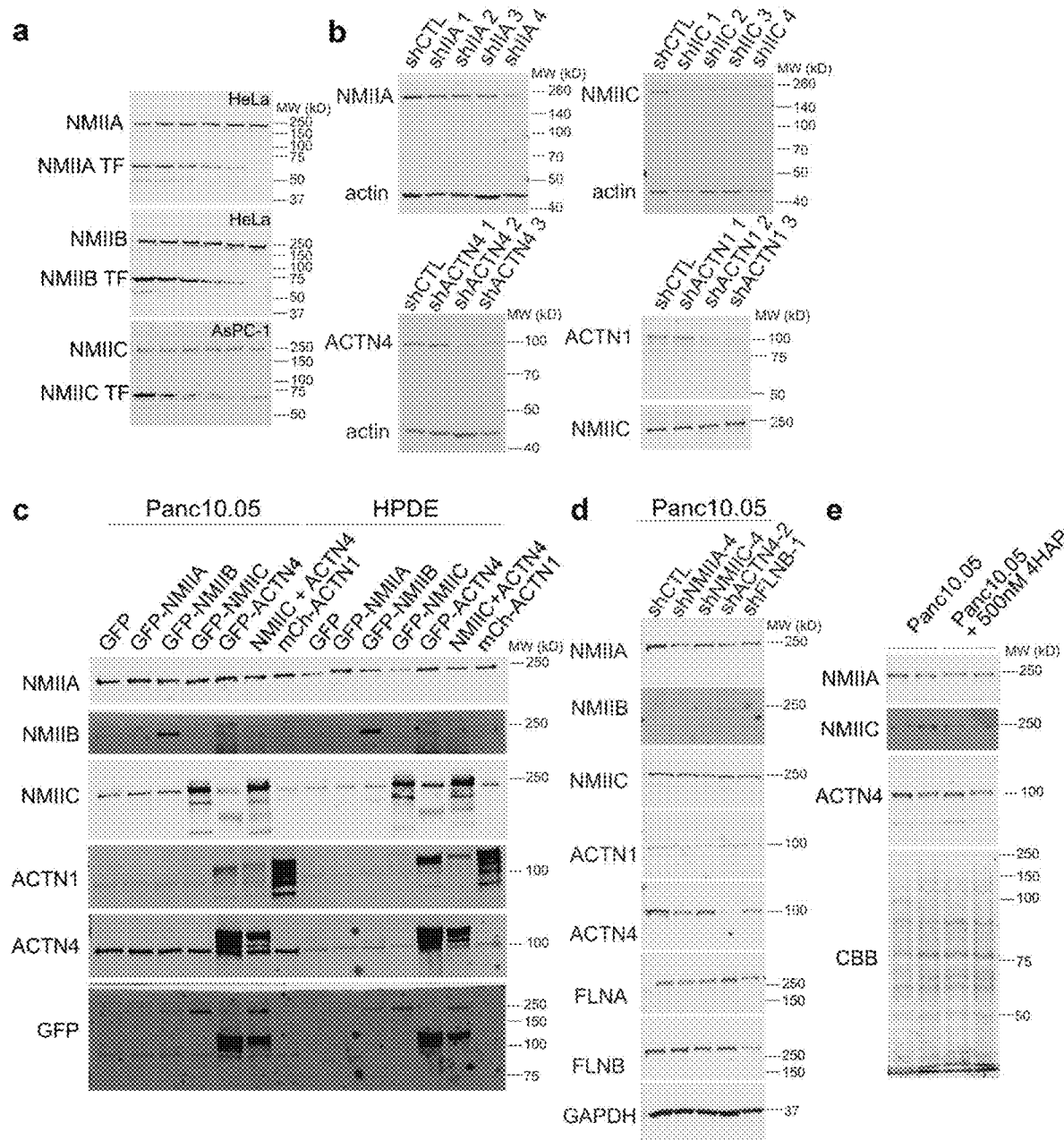
FIG. 24(A-E) Measurement of endogenous expression of nonmuscle myosin II paralogs and the effect of knockdown, overexpression, and 4-HAP treatment on the expression of mechanobiome proteins. (24A) Expression of myosin IIA (NMIIA), myosin IIB (NMIIB), and myosin IIC (NMIIC) was measured by comparing endogenous expression (upper band) to a standard curve of purified antibody epitope (lower band) added to HeLa or AsPC-1 cell extracts. (24B) Knockdown of NMIIA, NMIIC, ACTN4, and ACTN1 using multiple shRNA constructs was confirmed by western analysis compared to a loading control (actin or NMIIC). (24C) Overexpression of GFP-NMIIA, GFP-NMIIB, GFP-NMIIC, GFP-ACTN4, or mCherry-ACTN1 was verified by western analysis in HPDE and Panc10.05 cell lines. (24D) Knockdown of NMIIA, NMIIC, ACTN4, and ACTN1 does not alter the expression of the other NMII and ACTN paralogs. (24E) Overnight 4HAP treatment does not affect the expression of NMIIA, NMIIC, or ACTN4 in Panc10.05 cells (even loading verified by Coomassie Brilliant Blue staining).

To determine if PDAC cell lines can be used to study the changing mechanobiome landscape, the inventors first assessed if the expression patterns that they observed in patient samples (FIG. 17) matched generally with changes between WT-like HPDE and various tumor and metastatically-derived lines. Western analysis across four lines revealed a general increase in myosin IIA and IIC, the disappearance of myosin IIB, and an increase in α-actinin 4 and filamin B, with moderate or unchanged levels of α-actinin 1 and filamin A (FIG. 18). To begin to develop a quantitative framework for the role of myosin IIs in pancreatic cancer and because the small molecule 4-HAP the inventors have used to modulate cell mechanics works through myosin IIB and IIC, the inventors measured the concentration of each myosin paralog in these pancreatic cancer-derived cells. The inventors first calibrated both HeLa cells, which express myosin IIA and IIB, and AsPC-1 cells, which express myosin IIC, to generate a quantitative comparator for measuring each paralog's concentration across cell lines. To calibrate HeLa and AsPC-1 cells, the inventors added purified paralog-specific myosin II tail fragments to the extract (FIG. 24a). From these calibration measurements, the inventors calculated that the nonmuscle myosin IIA concentration in human pancreatic cells ranged from 540 nM in HPDE cells to 770 nM in Panc4.03 cells. These values compare favorably with the amounts of myosin II in budding yeast (Myo2p, 450 nM; Myp2p, 380 nM) and in *Dictyostelium discoideum* (Myo II, 3.4 µM) (FIG. 18b). By comparison to myosin IIA, myosin IIB and IIC are found at much lower concentrations. Interestingly, myosin IIC increased 1.5-fold from approximately two percent of all myosin II in HPDE cells to about three percent of all myosin II in AsPC-1 cells, while myosin IIB decreased from ~8% of all myosin II in HPDEs to undetectable in AsPC-1 cells (FIG. 18a, b). The dramatic change in myosin IIC in normal and cancerous ducts in the immunohistochemistry supports the myosin quantification across PDAC cell lines (FIG. 17). While myosin IIC appears to be a minor myosin II paralog based on its concentration, in fact we find below that this paralog plays a major role in pancreatic cancer cell mechanics and behavior.

Mechanoresponsive Machinery Impacts Cell Mechanics in PDAC Lines and can be Modulated by 4-Hydoxyacetophenone (4-HAP)

Figures 19A, 19B:
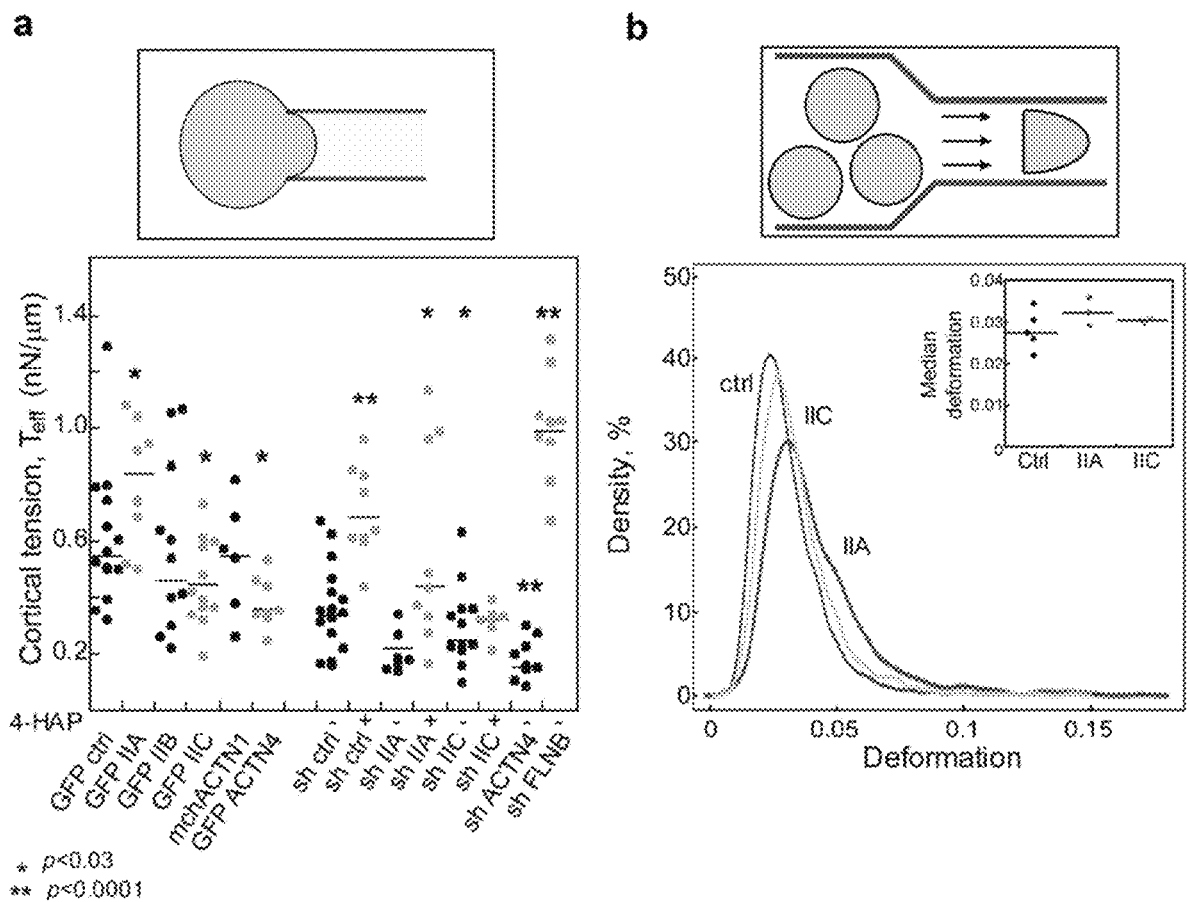
FIG. 19(A-B) Mechanoresponsive proteins impact cortical tension and deformability of PDAC cells. (A) The effective cortical tension (Teff) measured by MPA experiments (schematic) is significantly affected by overexpression of myosin IIA, myosin IIC, and α-actinin 4, all mechanoresponsive paralogs. 500-nM 4-HAP increases the cortical tension of sh-control cells. 4-HAP also increases the cortical tension in myosin IIA knockdown cells, whose primary myosin paralog myosin IIC is activated by 4-HAP[32]. Knockdown of myosin IIC also leads to a decrease in cortical tension, unchanged by 4-HAP challenge. Medians plotted; *$p<0.03$; **$p<0.0001$ relative to control. (B) RT-DC experiments (schematic) demonstrate increased deformation when myosin IIA and myosin IIC are knocked-down (plotted as a probability distribution). All cell lines are generated from Panc10.05 cells. N=7521 cells for control, 1383 cells for myosin IIA knockdown, and 5933 cells for myosin IIC knockdown. Cell types are distinct ($p<0.0001$). Inset: Median deformation of three to five RT-DC independent runs across cell types from which the elastic modulus was calculated.

The inventors have demonstrated that WT-like HPDE cells are less deformable than patient-derived PDAC cell lines. To determine if mechanoresponsive elements of the PDAC mechanobiome contribute to this mechanical differential, the inventors used micropipette aspiration (MPA) to measure the effective cortical tension (Teff) of cells with overexpression or knockdown of myosin II, α-actinin, and filamin paralogs in Panc10.05 cells (FIG. 19a). Across all cell lines, knockdowns were 70-95% (FIG. 24b). Driving myosin IIA levels up or down yielded an altered cortical tension which rose and fell with myosin IIA expression levels. Myosin IB overexpression had no impact on cortical tension. Myosin IIB knockdowns were not pursued since Panc10.05 cells (as well as other PDAC lines and patient tissue samples) have no detectable levels of this protein (FIG. 18a, FIG. 17a, FIG. 23). Alpha-actinin 1 overexpression had no effect on cell mechanics, while both overexpression and knockdown of α-actinin 4 decreased the Teff by half (FIG. 19a). Filamin A and B overexpressing cells ruptured under the applied pressures needed to measure cortical tension where the condition of Lp=Rp must be met. However, filamin B knockdown cells could be measured and had an increase in cortical tension (FIG. 19a).

Interestingly, despite contributing only 3% of the overall myosin II in these cells (FIG. 18c), overexpression and knockdown of myosin IIC had a profound impact on cell mechanics, leading to an overall softening of the cellular cortex and a ~50% reduction in cortical tension. To further explore the impact that myosin IIC has on the PDAC mechanobiome and cell mechanics, the inventors used the small molecule 4-hydroxyacetophenone (4-HAP). In *Dictyostelium*, 4-HAP increased cortical tension by driving myosin II to the cell cortex. 4-HAP shows myosin II paralog specificity in mammalian cells by increasing the assembly of myosin IIC (and IIB) and decreasing the deformability of several PDAC cell lines. As predicted, 4-HAP treatment increased the cortical tension of control cells where myosin IIC is present, but had no impact on myosin IIC-depleted cells (FIG. 19a).

Figures 25A, 25B:
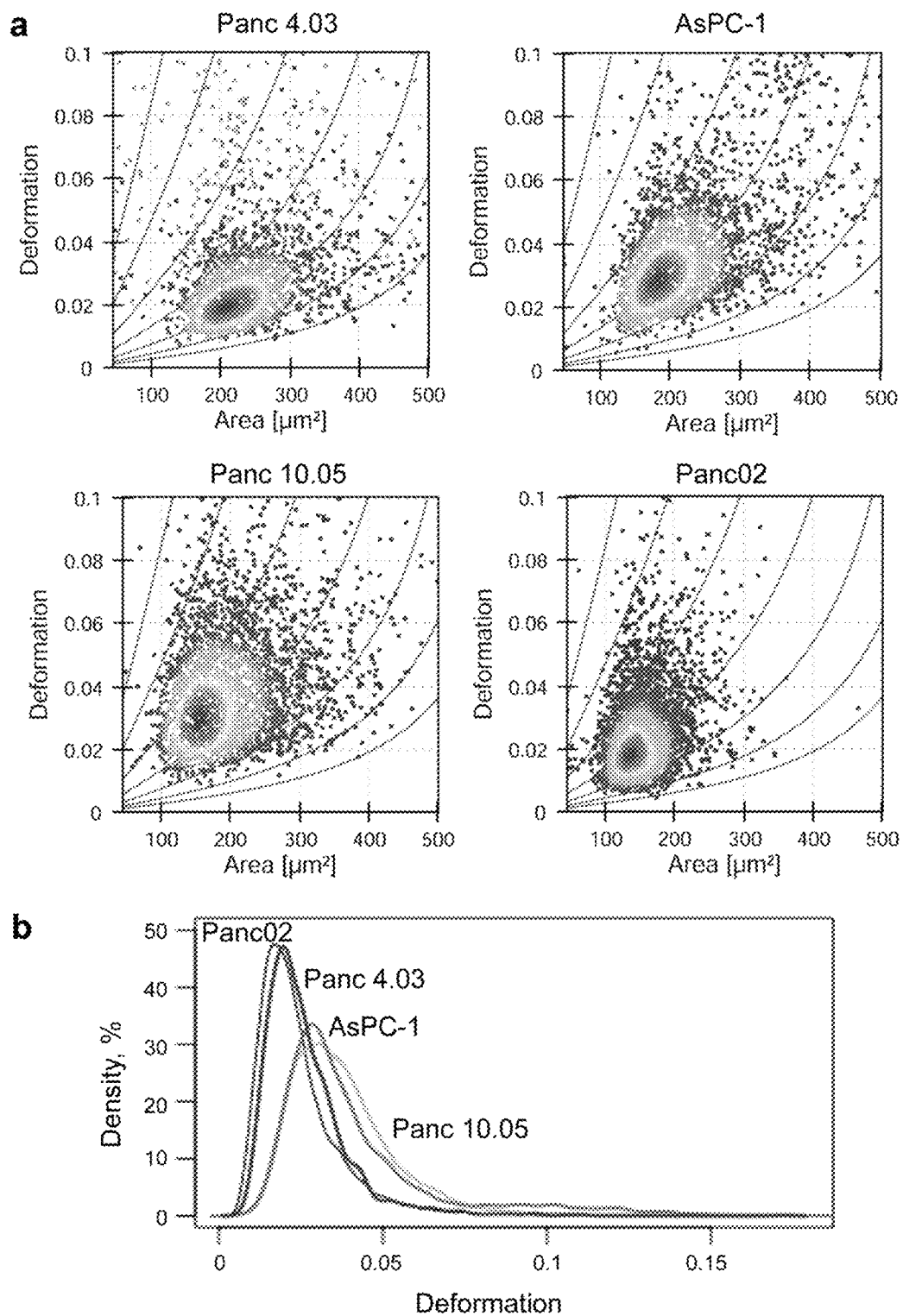
FIG. 25(A-B) Pancreatic cancer cell lines are mechanically distinct from each other. (25A) RT-DC allows short-timescale cell deformation (4-ms timeframe) and cell area of thousands of cells to be rapidly measured. AsPC-1, Panc02, Panc4.03, and Panc10.05 have different degrees of deformation, likely reflecting the accumulating genetic lesions associated with the different stages of PDAC progression from which each cell-line was derived. (25B) Density plots of deformation for each cell type demonstrate distinct mechanical signatures.

In addition to micropipette aspiration, which measures mechanical properties on the >500-ms time-scale (cortical tension measurements are performed over 10 s of seconds), the inventors used Real Time Deformability Cytometry (RT-DC), which measures mechanics on the 4-ms timescale and across the whole cell (FIG. 25). Reduction of myosin IIA, but not myosin IIC, increased cell deformation (FIG. 19b). The deformation was converted to an elastic modulus and calculated to be 1.2 kPa for control, 1.1 kPa for shIIA, and 1.2 kPa for shIIC. The small 8% reduction in the elastic modulus measured for knockdown of myosin IIA, which is the most abundant paralog in the PDAC cells, is similar to the reduction in elasticity measured for WT versus myoII genetic deletion cells in *Dictyostelium*. The elastic modulus measured on short time-scales contrasts with the ~2-fold difference in cortical tension measured over longer time-scales, highlighting the complexity of the mechanical roles of these proteins.

Figures 20A, 20B, 20C, 20D, 20E, 20F:
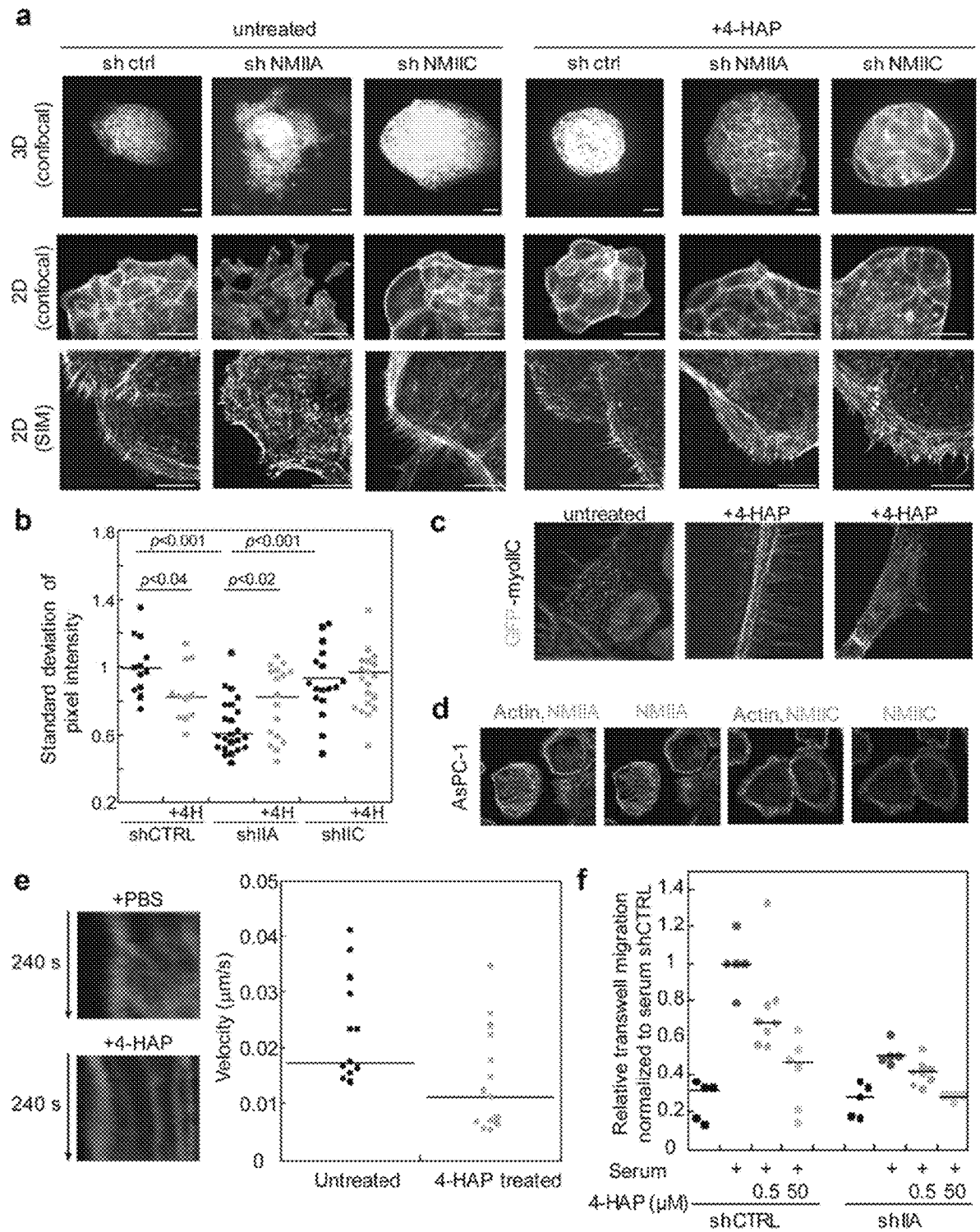
FIG. 20(A-F) Myosin IIC impacts cytoskeletal actin architecture, leading to actin belt formation and altered cell behavior upon 4-HAP treatment. (A) Tissue spheroids of Panc10.05 derived cells, grown and imaged in 3D (Matrigel) or 2D (collagen) show dissemination, exacerbated in myosin IIA knockdowns, and reversed in the absence of myosin IIC, with the emergence of actin cortical belts. Actin belts are formed in 4-HAP treatment when myosin IIC is present. Scale bar=40 m except SIM images in which case the scale bar=10 m. (B) Quantification and verification of these actin structures as a standard deviation of pixel intensity (a coarseness index); see Methods section for detailed explanation. Medians plotted; significance on graphs. (C) GFP-myosin IIC decorates actin filaments, especially actin belts generated by 4-HAP treatment in tissue spheroids. (D) Endogenous labeling of myosin IIA in fixed AsPC-1 cells shows myosin IIA colocalized on actin stress fibers and myosin IIC colocalized with actin on the cell cortex. (E) Sample kymographs of line scans across active leading edges in AsPC-1 SirAct live-stained cells. Graph shows decreased retrograde flow with 4-HAP treatment. Medians are plotted on the graph. (F) Treatment with 4-HAP of AsPC-1 shCTRL and shIIA cells shows moderate dose-dependence reduction of transwell migration. Medians are plotted on the graph.

Nonmuscle Myosin IIC Alters Actin Bundling in Cells, Impacting Migration and Dissemination In addition to mediating mechanoresponsiveness (FIG. 16) and cell mechanics (FIG. 19), nonmuscle myosin II proteins also impact cytoskeletal arrangements and contractility. To determine how myosin IIC specifically impacts cytoskeletal organization in collectives of cells, the inventors generated tissue spheroids with knockdown Panc10.05 cell lines and examined the impact of 4-HAP treatment on those spheroids. Control knockdowns plated in 3D collagen I matrices showed partial dissemination, which was greatly increased in NMIIA knockdowns, similar to previous observations. Knockdown of myosin IIC showed no dissemination (FIG. 20a). Upon treatment with 4-HAP for 24 hours, dissemination in both the control and NMIIA knockdown decreased, while no effect was observed in the myosin IIC-depleted spheroids. To decipher the detail in cytoskeletal structures, spheroids were plated on collagen I-coated 2D substrates, and similar morphological differences were observed as in the 3D cultures (FIG. 20a, row 2). In addition, the inventors observed tight actin cortical banding patterns on the periphery of the tumor spheroids in the absence of myosin IIC. This banding pattern was also observed in the control and NMIIA knockdown spheroids with 4-HAP treatment. To assess this actin redistribution, the inventors used computer-assisted image analysis on the 2D spheroids and measured the continuity of banding, the percent coverage of actin filaments at the spheroid edge, and the homogeneity of the actin in those structures (calculated as the standard deviation of pixel intensity) (FIG. 26). Across all analyses, myosin IIA knockdown spheroids had the least amount of discrete and continuous banding (FIG. 20b, FIG. 26b) and the least amount of actin staining at the tissue edge (FIG. 26c). Upon 4-HAP treatment, all of these metrics changed— more discrete and continuous belts emerged and the median percentage staining of actin increased 2-fold. By comparison, the myosin IIC knockdown tissue spheroids had discrete and continuous actin belts that remained unchanged upon 4-HAP addition (FIG. 20b, FIG. 26b, c), consistent with 4-HAP working primarily through myosin IIC. Interestingly, by these analytics, treatment with 4-HAP in the control tissue spheroids seemed to decrease discrete band formation.

The inventors then used Structural Illumination Microscopy (SIM) to acquire higher resolution views of the structures along the tissue spheroid edges (FIG. 20a bottom row, b). In the control spheroids, the actin belts are formed by the structural rearrangement of the actin bundles. Here, 4-HAP induces a coarser distribution of actin composed of dense actin belts and leads to the emergence of filopodial-like structures or retraction fibers. In the myosin IIA knockdowns treated with 4-HAP, tight actin belts, as well as elaborate arrays of parallel actin bundles, are also clearly visible. In contrast, myosin IIC knockdowns had peripheral actin structures that were largely unchanged between untreated and 4-HAP-treated samples. Thus, 4-HAP induces alterations in peripheral actin structures in a myosin IIC-dependent manner.

To address myosin IIC's role in actin rearrangements, the inventors next determined its cellular localization. In tissue spheroids, fluorescently-labeled myosin IIC is both diffusely localized throughout the cell and along actin filaments (FIG. 20c). When actin filaments collapse to form actin belts upon 4-HAP treatment, myosin IIC shows strong co-localization with those belts. In single Panc10.05 and AsPC-1 cells, endogenous myosin IIC is predominately confined to the cell cortex including in actin-rich protrusions, whereas myosin IIA localizes along stress fibers (FIG. 20d).

Overall, these observations and analysis highlight two major findings. First, in collections of cells, despite being present in small quantities, myosin IIC plays a role in actin rearrangements and dynamics. Myosin IIA, known to contribute to retrograde actin flow, may work in concert with myosin IIC to drive these cytoskeletal rearrangements. Second, 4-HAP reduces the fluidity of the network: by stabilizing actin belt structures in the absence of myosin IIA and in the presence of both myosin IIA and myosin IIC, 4-HAP alters the actin cytoskeleton in a manner that inhibits dissemination from tissue spheroids.

Figures 27A, 27B:
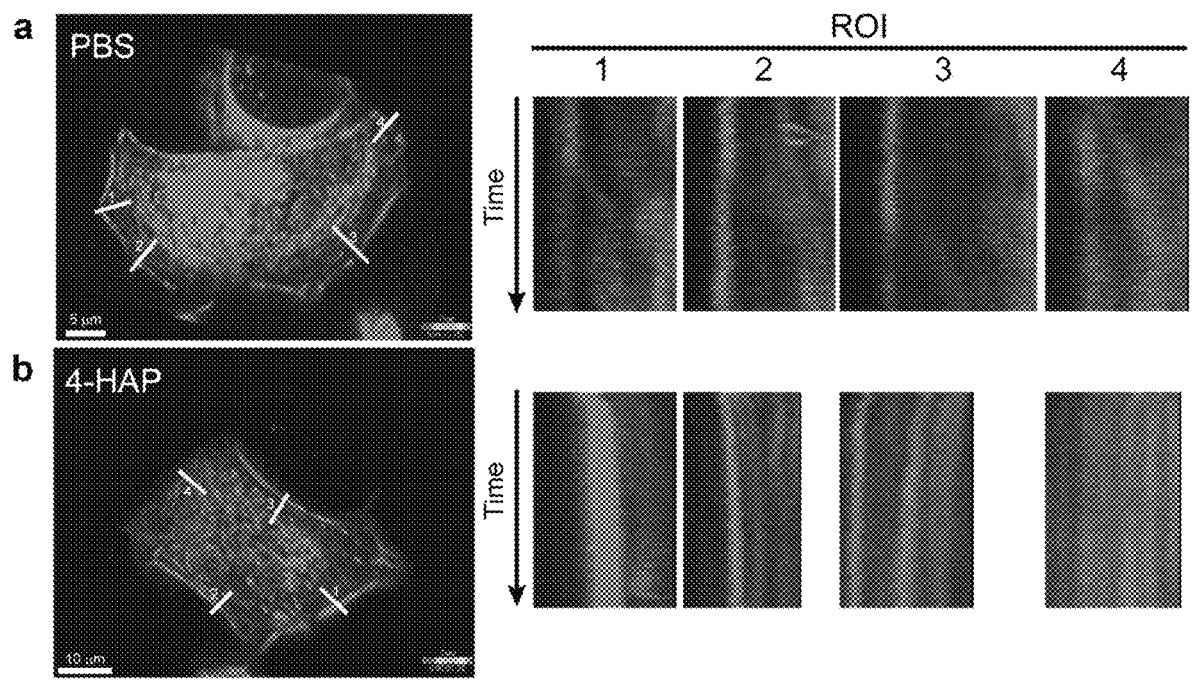
FIG. 27(A-B) 4-HAP decreases actin retrograde flow. (27A) Untreated AsPC-1 cell labeled with SirAct. (27B) AsPC-1 cell treated with 4-HAP and labeled with SirAct. Kymographs from four regions of interest (ROI) displayed on the right correspond to the four line scans (yellow) in the images on the left. Kymographs are length adjusted so that time-scale matched across the cells. Scale bars are shown on the images on the left.

Because retrograde flow moves actin away the cell perimeter, the cortical actin belts could be formed by a reduction in this flow. Therefore, the inventors examined the impact of 4-HAP on retrograde flow. The inventors live-stained cells with SiR-actin and observed flow using lattice sheet microscopy. Most 4-HAP-treated cells had undetectable levels of actin flow. Those in which retrograde flow could be measured showed a 50% reduction in velocity over untreated controls (FIG. 20e, FIG. 27). This large and measurable impact on actin dynamics explains in part the dose-dependent decrease on trans-well migration in control and myosin IIA knockdown AsPC-1 cells (FIG. 20f). Overall, 4-HAP's impact on actin flow, cell dissemination, and invasion suggests its potential for reducing PDAC metastasis.

4-HAP Decreases PDAC Metastatic Potential in a Mouse Model

Figures 21A, 21B:
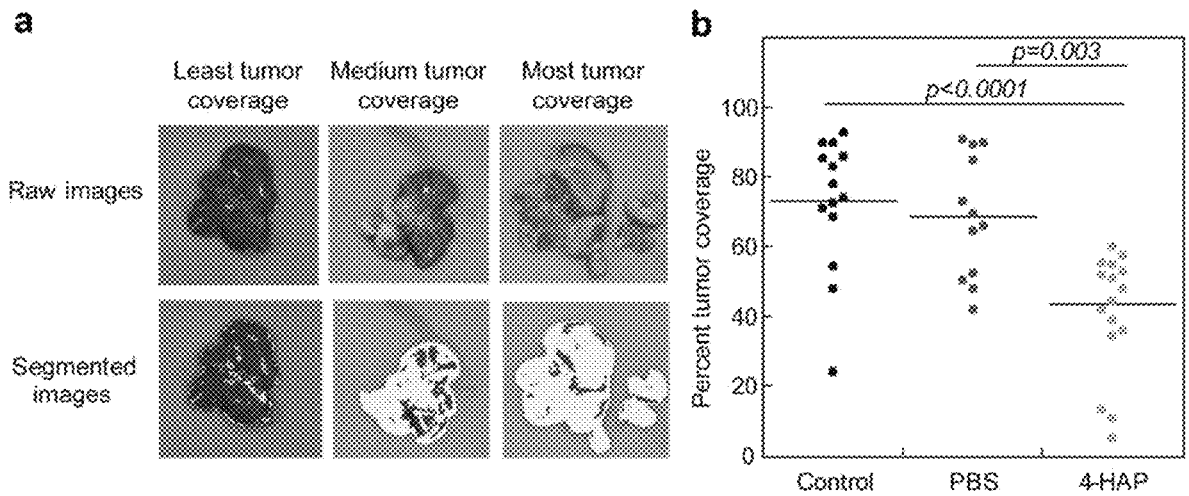
FIG. 21(A-B) 4-HAP reduces PDAC liver metastasis in murine model. Livers harvested from 4-HAP-treated mice that underwent hemi-splenectomies with AsPC-1 cells show a reduction in tumor coverage over those livers from untreated mice. (A) Images were quantified using image segmentation based on color gradients to discern tumor coverage (FIG. 27). (B) Quantification of tumor coverage show a 50% reduction in surface tumor load. Medians are provided on the graph.
Figures 28A, 28B:
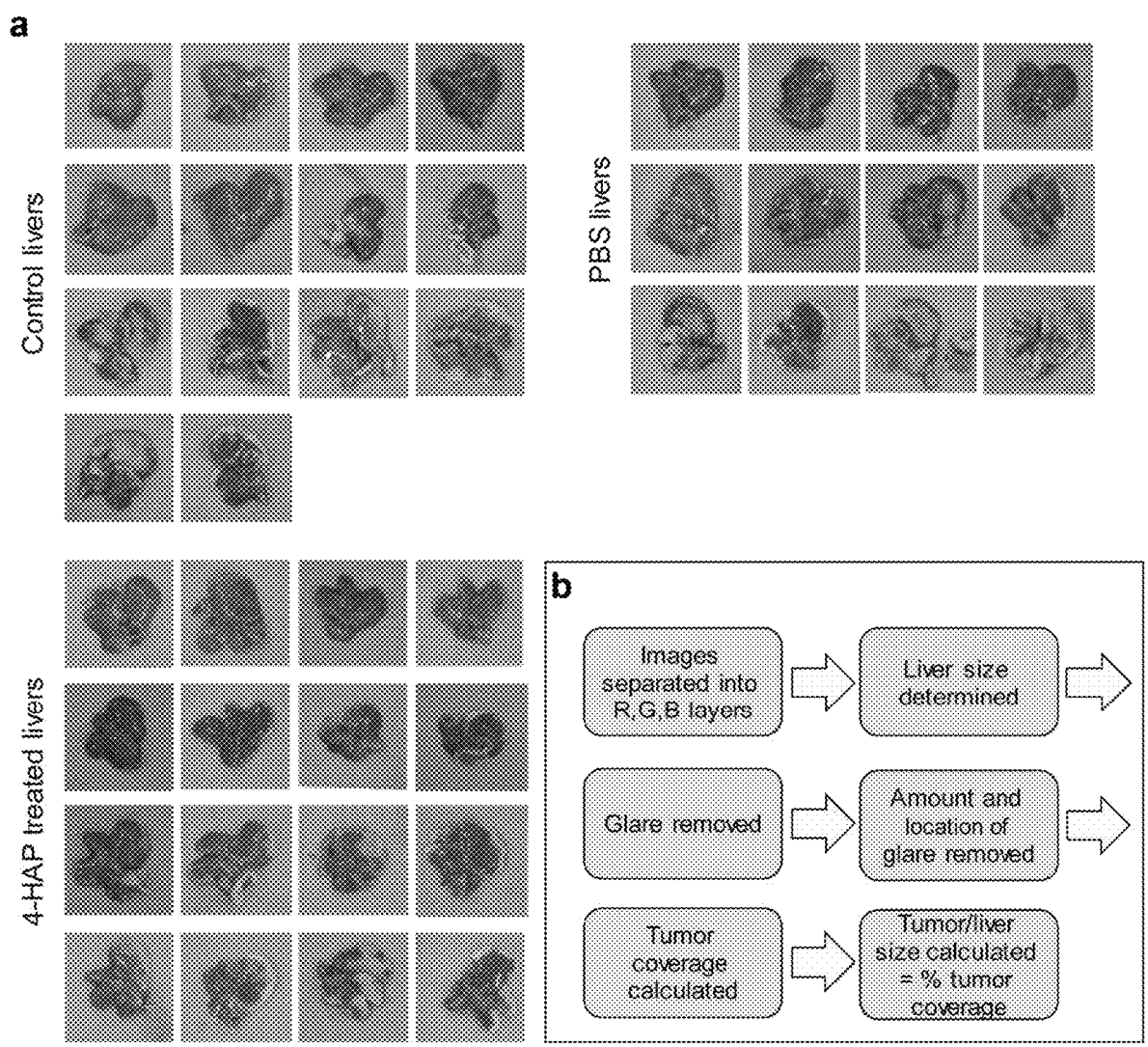
FIG. 28(A-B) 4-HAP treated livers show reduced surface tumor coverage. (28A) All livers harvested from mice that underwent hemi-splenectomies are shown. (28B) Work-flow diagram of quantification of tumor burden shown in main text.

Critical regulators of myosin II have significantly altered expression associated with pancreatic cancer progression and in pancreatic cancer-derived cell lines. These genetic alterations suggest that myosin II, particularly myosin IIC whose expression is specifically elevated in pancreatic ductal epithelia, may be an attractive target for impacting PDAC cell behavior. Therefore, the inventors tested 4-HAP in a mouse model for PDAC metastasis. Hemi-splenectomies with 4-HAP pre-treated metastatic AsPC-1 cells were performed on nude mice which were subsequently divided into three groups: control, PBS (200 μl PBS IP injections, every other day), and 4-HAP (5 mg/ml, 200 μl IP injections, every other day). Mice were harvested at 5-weeks post-surgery, when the first mouse expired. Metastasis to the liver was observed and quantified by an in-house Matlab script that determined surface area tumor coverage. Results from both liver weights and tumor coverage show that 4-HAP treatment leads to a reduction in tumor formation (FIG. 21, FIG. 28).

A cell's ability to react to changing mechanical and chemical cues in its environment depends on the adaptability of its mechanobiome. Increased contractility and altered deformability, as well as rapid turnover of cytoskeletal proteins, are trademarks of cells responding to constantly changing surroundings. Entire programs are upregulated to provide cells with added adaptability at specific time points as developing embryos and differentiating cells show increased expression of mechanoresponsive proteins during mechanically turbulent periods. For example, filamin's mechanoresponsiveness is required for maturation of actin-rich ring canals that interconnect the nurse cells and oocyte in developing *Drosophila* egg chambers, and filamin B is upregulated in embryonic vascular endothelial cells. Both α-actinin 1 and α-actinin 4 show temporally defined expression in developing zebrafish embryos, with both expressed in the notochord and α-actinin 4 also expressed in the developing gut. Each of the nonmuscle myosin II paralogs have roles in development as well, including but not limited to neurite outgrowth and maturation (NMIIB and NMIIC), nephron development (NMIIA and NMIIB), and hearing (NMIIA).

In the mechanobiome, forces are shared between myosin II and different actin crosslinkers, with myosin II having potentiating or inhibitory effects on certain crosslinkers and vice versa. This mechanosensory system constitutes a control system, where mechanical inputs can be converted to signaling outputs in a manner analogous to chemical signal transduction. Through our work, an important delineation has emerged: the cell has at least two systems of proteins that when depleted, lead to a reduction in cortical viscoelasticity and tension. One set of proteins leads to increased mechanoresponsiveness, while the other set of proteins leads to reduced mechanoresponsiveness. Cells that mature into terminally differentiated tissues often readjust the cytoskeletal milieu to favor reduced mechanoresponsiveness over their developmental program. These stable expression patterns, however, are altered in precancerous cells (often caused by upstream genetic lesions), and revert cells to programs activated in early development that endow them again with increased adaptability.

Here the inventors show that in the case of pancreatic ductal adenocarcinoma, the mechanoresponsive proteins myosin IIA, myosin IIC, α-actinin 4, and filamin B are upregulated in patient-derived tissues; they alter the structural arrangement of the actin cytoskeleton and impact cell mechanics. In addition, despite its low abundance, myosin IIC works in conjunction with myosin IIA to facilitate actin organization and retrograde flow. These data suggest that the interplay between these two paralogs is necessary to control leading edge dynamics of PDAC cells, bestowing a mechanical advantage to these cells. Also, the inventors' data on myosin IIC suggest that changes in the expression level of minor proteins that are often discounted in larger data mining may in fact, be worthy of reconsideration, given the large impact myosin IIC has on cell mechanics and cell behavior. Our in vivo metastasis assays demonstrate that the myosin IIA-IIC dynamic can be fine-tuned towards a therapeutic benefit with mechanical modulators such as 4-HAP. In addition, because myosin IIC is specifically upregulated in ductal adenocarcinoma cells, the pharmacological modulation of this protein is unlikely to negatively impact healthy pancreatic tissue; 4-HAP should synergize with other strategies such as immunological intervention in pancreatic cancer patients, since immune cells do not typically express myosin IIC.

Figure 22:
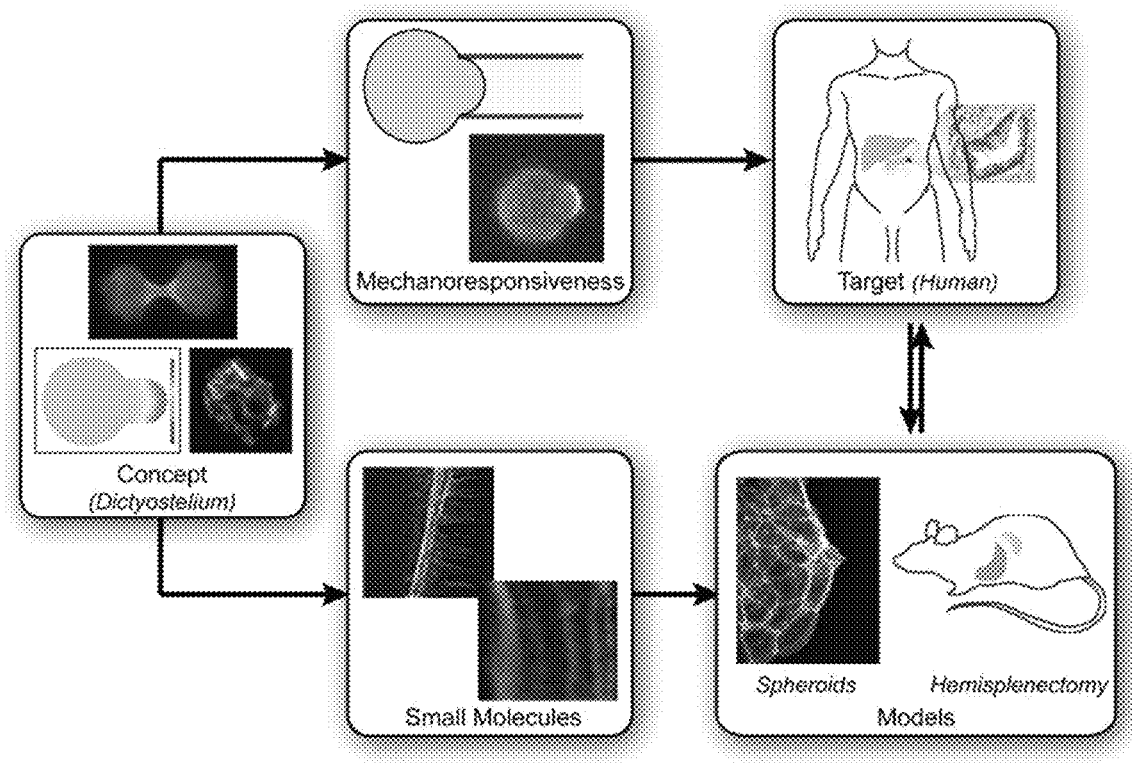
FIG. 22 Model systems to human pancreatic cancer. We have integrated our findings across models to access a targetable drug space for pancreatic ductal adenocarcinoma. We draw upon the molecular mechanisms of mechanoresponsiveness to design strategies for stabilizing the cellular dynamics that underlie metastatic potential. Concepts and Tools: We developed the underlying fundamental concepts for cell shape control, coupled with the identification of proteins involved in mechanical feedback regulation (mechanoresponsiveness), by studying cell division in Dictyostelium. This system also provided the framework for small molecule discovery used to modulate cell and tissue mechanics. Mechanoresponsiveness: Based on the molecular mechanisms of mechanoresponsiveness, we could predict paralog specificity of the human counterparts; those which are highly mechanoresponsive are also highly upregulated in pancreatic ductal adenocarcinoma. Small Molecules: A myosin II modulator 4-HAP, which we first identified in our screen using Dictyostelium, promotes myosin IIB and IIC assembly and drives myosin IIC-actin transverse arcs with inhibited retrograde flow. Models: In human pancreatic cancer cell spheroids, 4-HAP promotes the formation of transverse actin belts, which are associated with reduced dissemination. Myosin IIA knockdown promotes increased dissemination capability, which 4-HAP can overcome. In mouse hemisplenectomy assays, 4-HAP can reduce the metastatic burden of human pancreatic cancer cells. Target: The goal is to decrease mortality among human pancreatic cancer patients. By combining concepts revealed in our models, which cover the dynamics, cell shape control, mechanoresponsiveness, and motility conserved in human cancer cells, we have uncovered a targetable drug space. PDAC's mechanobiome here, is targetable through the upregulation of myosin IIC and the discovery of 4-HAP, a myosin IIC modulator. Similar strategies can be employed with other elements of the mechanobiome.

Furthermore, the observations presented here imply that targeting cancer by broadening strategies to include small molecule mechanical modulators can have significant effects on metastatic load. Modulation of mechanoresponsive proteins has several advantages. First, the inventors can fine-tune the activity of proteins that are upregulated in cancerous tissue, thus harnessing the cell's intrinsic protein make-up to revert them to more normal phenotypes, while protecting healthy cells that do not upregulate these targeted proteins. Second, this strategy draws upon the normal biochemistry of the protein to overwhelm the mechanics of the system. In these studies, the inventors are hitting on both points: The inventors are using 4-HAP to increase the assembly of myosin IIC, which is specifically upregulated in PDAC, in order to overcome the protein's innate adaptive ability. 4-HAP treatment pushes myosin IIC to lock onto the cytoskeletal network, thus inhibiting the tumor cell's ability to polarize and reorganize its actin cytoskeleton. Overall, incorporating the mechanobiome as a targetable drug space in combination with other therapeutic approaches, is likely a valuable strategy for reducing PDAC metastasis (FIG. 22).

Materials and Methods
Cell Culture and Strains
Parental Pancreatic Cell Lines

Human pancreatic ductal epithelial cells (HPDE) were obtained from Dr. Ming-Sound Tsao (University of Toronto, Ontario Canada) and human primary tumor-derived cells (Panc10.05) and human metastatically-derived cells (AsPC-1) were purchased from ATCC. Panc02 cells (highly tumorigenic murine pancreatic tumor cell line) were derived from a methylcholanthrene-treated C57B1/56 mouse. All were grown using standard cell culture methods. HPDE cells were grown in Keratinocyte media (Gibco) with 1% penicillin and streptomycin, while Panc10.05 and AsPC-1 cells were grown in RPMI 1640, L-Glutamine media (Gibco) supplemented with 1% penicillin and streptomycin, sodium pyruvate (Gibco), non-essential amino acids (Gibco), 10% FBS (ATLAS Bio), and 0.2% insulin. In accordance with NIH guidelines, cell lines were authenticated using short tandem repeat profiling at the genetic recourses core facility at Johns Hopkins University.

Engineered Cell Lines

Both lentiviral knockdown and adenoviral overexpression cell lines were generated in Panc10.05, and in some cases AsPC-1 and HDPE parental strains. For lentiviral knockdown, the hairpins used (Sigma Mission shRNA) were selected after having analyzed a minimum of three shRNAs for each gene:

shCTL NT control:
(SEQ ID NO: 2)
5'-CAACAAGATGAAGAGCACCAA-3' shIIA:
(SEQ ID NO: 3)
5'-GCCAAGCTCAAGAACAAGCAT-3' shIIC:
(SEQ ID NO: 4)
5'-GCTCAAATATGAGGCCACAAT-3' shACTN4:
(SEQ ID NO: 5)
5'-CAGGACATGTTCATCGTCCAT-3'

-continued
shFLNB:
(SEQ ID NO: 6)
5'-GCTGACATTGAAATGCCCTTT-3'

Target plasmids were co-transfected with generation 2.0 lentiviral packaging plasmids psPAX.2 and pMD2.G via Transit 20/20 (Mirrus) transfection reagent into Lenti-X HEK293t cells. 16 hrs after transfection, the media was changed to fresh DMEM (10% FBS/1% penicillin-streptomycin). Virus-containing media was harvested after an additional 24 hrs for lentiviral infection to target cells. Positively infected cells were then selected for with 1 or 5 ng/ml puromycin in Panc10.05 or AsPC-1 cells, respectively, for 5 days as determined by kill-curve analysis. Knockdown was confirmed with western analysis.

For overexpression using the adenoviral system, fluorescent adenovirus for the expression of GFP-MYH9, GFP-MYH10, MYH14-GFP, mCherry-ACTN1, GFP-ACTN4, and GFP control were purchased from Vector BioLabs, Malvern, Pa. Optimal multiplicity of infection (MOI=# of virus particles/cell) was first calculated by plating equal numbers of cells in a 96-well plate, then titrating virus between 0 and 200 MOI and observing fluorescence and cell death at 48 hours. For the myosins, the optimal MOI was found to be 50, where cell death was not seen and the percent of fluorescent cells was highest. While an MOI of 50 showed the highest expression and no death for the actinin constructs, the amount of protein expressed in cells was extremely high by western analysis, and so the MOI was lowered to 10. For all studies, an MOI of 50 was used for the GFP control. The filamin A and filamin B genes were too large to insert in an adenoviral vector with a fluorescent reporter. For mechanoresponse experiments on filamin A and filamin B, AsPC-1 cells were transiently transfected with FuGene HD transfection reagent (Promega, Madison, Wis.) using 1 g of DNA for each plasmid and imaged 36 hours post-transfection. The filamin A plasmid, pmdsRed-FLNA, was a gift from Fumihiko Nakamura. The filamin B plasmid, EGFP-FLNB-pCI-C1, was a gift from Arnoud Sonnenberg.

Immunohistochemistry of Patient-Derived Samples
Antibodies and Reagents

Antibodies used include: myosin IIA Poly19098 (BioLegend, 909801), myosin IIB (D8H8) XP (Cell Signaling Technology, #8824), myosin IIC (D4A7) (Cell Signaling Technology, #8189), α-actinin 1 (OTI7A4) (OriGene, TA500072), α-actinin 4 (G-4) (Santa Cruz Biotechnology, sc-390205), filamin A (Cell Signaling Technology, #4762), filamin B antibody [N1] (GeneTex, GTX101206), and β-actin (8H10D10) (Cell Signaling Technology, #3700).

Tissue Preparation

The human tissue was collected and evaluated under JHH IRB #NA_00001584. Human pancreatic cancer samples were fixed in formalin, paraffin embedded, and processed for routine histology. Additional 5-μm sections were cut onto plus slides and baked prior to IHC staining.

Immunohistochemistry Staining

Immunohistochemistry was performed as previously described. In short, warmed slides were deparaffinized in sequential zylene washes, followed by 100%, 95%, and 70% ethanol washes. Slides were incubated in 0.3% $H_2O_2$ in MeOH for 20 min, then washed twice in water. Slides are steamed in citrate buffer (pH 6.0) for 35 min. Cooled slides were washed twice in water and three times in TBST (50 mM Tris-Cl, pH 7.5; 150 mM NaCl; 0.1% Tween-20). Slides were edge dried with a Kimwipe and Serum Free Protein Block Dako X0909 (Agilent, Santa Clara, Calif.) was applied for 10 min. Dried slides were incubated with primary antibody for 1 hr at 22° C., washed in TBST three times, air-dried, and incubated in secondary antibody (Dako, K400111-2, EnVision+, HRP. Mouse or K401111-2, En Vision+HRP. Rabbit 1100 tests (Dako) for 20 min at 22° C. Slides were washed three times in TBST, followed by incubation for 2-3 min in DAB+. Stained slides were washed with water, incubated for 15 sec in hematoxylin (Sigma), and washed first with water, then ethanol, and water again, incubated in acid alcohol, with a final water rinse. Slides are incubated in bluing water, washed, and dehydrated in 70% ethanol for 2 min, 100% ethanol for 2 min, and xylenes for 1 min.

Scoring and Imaging

Slides were scanned using the Hamamatsu Digital Scanner and white balanced in Adobe Photoshop (Adobe Systems, Inc). Samples were scored based on both intensity of staining and surface area of duct covered by staining. Each slide was visualized in its entirety to determine uniformity of staining. Five cancerous ducts and five normal ducts (when present) were selected at random. Ducts with no staining were given a 0/0, ducts with intense staining on over 50% of the ductal surface were given a 2/2, with intermediate staining lying between these two endpoints. Ducts with intense staining on less than 50% of their area were scored as 2/1, ducts with moderate staining on over 50% of their ductal surface were scored as 1/2, and those with moderate staining on less than 50% of their ductal surface were scored as 1/1. To quantify the distribution of staining across all patient samples (FIG. 16b), individual duct scores were reassigned as follows: 0/0 as a 1, 1/1 as a 2, 1/2 as a 3, 2/1 as a 4, and 2/2 as a 5. Slides were imaged on NDP.View2 NanoZoomer Digital Pathology (NDP.View2, Hamamatsu Photonics, Japan).

Quantification of Cellular Myosin II Paralog Concentrations by Western Analysis

Myosin II Tail Fragment Protein Purification

Bacterial expression plasmids coding for an N-terminal 6×His tag (SEQ ID NO: 1), fused to the mCherry fluorophore, fused to the assembly domains of human myosin-IIA (residues 1722-1960), human myosin-IIB (residues 1729-1976), and mouse myosin-IIC (residues 1782-2033) were generated in pBiEx1 using standard cloning techniques. Proteins were expressed in BL-21 Star™ (DE3) (Invitrogen) E. coli in LB shaking culture overnight at room temperature. Bacteria were harvested by centrifugation and lysed by lysozyme treatment followed by sonication, and the lysate was clarified by centrifugation. Polyethyleneimine (PEI) was added to a final concentration of 0.1% to precipitate nucleic acids, which were then removed by centrifugation. The myosin-II constructs were precipitated by adding ammonium sulfate to 50% saturation and centrifuging. The pellet was resuspended in column running buffer, dialyzed against the same for a minimum of 4 hours, clarified by centrifugation and filtration, and run on a Ni-NTA metal affinity column, followed by a sizing column. The constructs were then concentrated and further purified by dialyzing against assembly buffer (10 mM HEPES, pH 7.1, 50 mM NaCl) until precipitate formed, followed by centrifugation and resuspension of the pellet in storage buffer (10 mM HEPES, pH 7.1, 500 mM NaCl). Protein purity was verified by SDS-PAGE followed by Coomassie Blue staining, and concentration was quantified by UV absorbance using the calculated extinction coefficient for each protein's amino acid sequence.

Quantitative Western Analysis

Cells were trypsinized and counted, then centrifuged into pellets containing $5\times10^5$ cells each. These pellets were washed in PBS and recentrifuged, then lysed in 75 μL RIPA lysis buffer plus 15 μL 6×SDS buffer. Due to cell volume and residual PBS, the total lysate volume reached 100 μL. 10 μL of lysate was added to each well of a 7% SDS-PAGE gel, or the equivalent of $5\times10^4$ cells/well. In addition, each well was spiked with a known quantity of purified myosin II tail fragment, containing the epitope region for the antibodies used, with sequential 2-fold dilutions. A 7% gel was used because it allowed for optimal transfer of both the large molecular weight endogenous myosin II and the smaller molecular weight purified tail fragment out of the gel. Transfer was most effective at a constant 45V for 16 hrs, using PVDF membranes to prevent smaller protein passthrough and verifying complete transfer of larger proteins by performing a Coomassie stain to verify that no protein was left in the gel following transfer. The average volume of an individual cell for each cell type was determined from the micropipette aspiration images, where cell radius is measured, and assuming the cell shape to be a sphere prior to aspiration. For each experiment, a standard curve was created from the spiked tail fragment to determine the total number of moles of endogenous myosin II in each lane. The number of cells per lane multiplied by the average volume of a single cell gave the total cell volume per lane, and concentration was determined as a ratio of these two values. Antibodies used were the same as those for immunohistochemistry (described above).

Micropipette Aspiration Assay for Mechanoresponse and Mechanics Measurements and Real-Time Deformability Cytometry Measurements The instrumental and experimental setups have been described previously. MPA assays and RT-DC measurements were all carried out in growth media for cortical tension measurements or Leibovitz L-15 media (Gibco) when fluorescence was quantified.

Measurements of Mechanosensory Accumulation of Proteins

A pressure difference was generated by adjusting the height of a motor-driven water manometer. Mammalian cells expressing desired fluorescent proteins were loaded into the observation chamber, which was filled with Leibovitz L-15 Medium w/o phenol red (Gibco). Cells were deformed using a pressure of 0.3 nN/μm² and recorded for 5 min. Pressures higher than this often led to blebbing or the separation of cell membrane from the cortex. All cells which demonstrated blebbing during recording were discarded. Images were collected with an Olympus IX81 microscope equipped with MetaMorph software and analyzed using ImageJ (National Institutes of Health). After background correction, the fluorescence intensity at the accumulation site inside the micropipette was normalized against the opposite cortex of the cell ($I_p/I_o$). The peak $I_p/I_o$ value during the 5 min timecourse was then normalized to the $I_p/I_o$ value at t=0 to adjust for initial variations in cortical fluorescence (Normalized $I_p/I_o$).

Cortical Tension Measurements

Pressure was applied to the cell cortex with a micropipette (6- to 8-μm radius; $R_p$) to the equilibrium pressure ($\Delta P$), where the length of the cell inside the pipette ($L_p$) was equal to $R_p$. The effective cortical tension ($T_{eff}$) was calculated by applying the Young-Laplace equation: $\Delta P = 2T_{eff}(1/R_p - 1/R_c)$, where $R_c$ is the radius of the cell and $\Delta P$ is the equilibrium pressure when $L_p = R_p$. Images were collected with an Olympus IX81 microscope equipped with Meta-Morph software and analyzed using ImageJ (rsb.info.nih.gov/ij).

Real-Time Deformability Cytometry

Mechanical measurements of thousands of cells were obtained as previously described. Approximately $10^6$ cells were trypsinized, spun, resuspended in media, and incubated at 37° C. for 10 min prior to loading onto the AcCellerator (Zellmechanik Dresden), using a 30-µm channel. Deformation and cell size data was collected in real-time at three different flow-rates and analyzed using ShapeOut (Zellmechanik Dresden; available at https://github.com/zellmechanik-dresden/ShapeOut). Differences in deformation were plotted as a probability distribution in R (r-project.org/), and the elastic modulus, based on the median of the deformation and area populations, the channel width, viscosity, and flow rate was calculated.

Imaging and Image Analysis

Imaging was performed in culture media or Leibovitz L-15 media without phenol red (Gibco) and 10% FBS for mechanoresponse and lattice light sheet experiments. Confocal imaging was performed on a Zeiss 510 Meta microscope with a 63× (1.4 NA.) objective (Carl Zeiss). Epifluorescence imaging was performed with an Olympus IX81 microscope using a 40× (1.3 N.A.) objective and a 1.6× optovar (Olympus), as previously described. Image analysis was performed with ImageJ (rsb.info.nih.gov/ij). Datasets were independently analyzed by multiple investigators.

Single Cell Assays

2D Random Migration

AsPC-1 cells were plated at a sub-confluent concentration in a 24-well tissue culture plate (<5,000 cells) and incubated overnight in growth media (see above). Prior to imaging, cells media was changed to Leibovitz L-15 media without phenol red (Gibco) containing 10% FBS and 1% penicillin/streptomycin. Cells were imaged using Molecular Devices IXM High Content Imager 10× objective (NA) every 30 min for 24 hrs. Cell roundness, velocity and area were quantified using ImageJ.

Retrograde Flow

AsPC-1 cells were grown on collagen I-coated (50 µg/ml) 5-mm coverslips for 16 hrs and then treated with 100-nM SiR-Actin (Cytoskeleton, Inc) and 1 M Verapamil for 4 hrs in Leibovitz L-15 without phenol red media, with or without 4-HAP (500 nM). Coverslips were transferred to the imaging chamber of the Lattice Light-Sheet Microscope (LLSM) (Intelligent Imaging Innovations) containing fresh Leibovitz L-15 media without SiR-Actin and verapamil plus the corresponding 4-HAP concentration. Cells were imaged for 3-5 min at 2-3-sec intervals, 50-150 planes per 3D stack, with a Nikon CFI75 Apochromat 25×/1.1 water-dipping objective. Retrograde actin flow was measured using ImageJ (rsb.info.nih.gov/ij). Datasets were independently analyzed by multiple investigators.

Transwell Assays

AsPC-1 cells were plated in 6.5-mm PET membrane transwell inserts with 8-µm pores (Costar #3464) in a 24-well plate at a concentration of 5,000 cells per well. Cells were allowed to adhere overnight in AsPC-1 media. Cell media was then changed to serum-free RPMI 1640 to starve cells for 18 hrs. Following starvation, cells were stimulated by changing media in the top chamber to fresh serum-free RPMI 1640±500 nM 4-HAP and complete AsPC-1 media ±500 nM 4HAP. Cells were then incubated for 24 hrs at 37 degrees C./5% $CO_2$ and then fixed in 4% paraformaldehyde, permeabilized in 0.1% Triton X-100 and stained with 1 µg/ml DAPI. Prior to imaging, the top chamber was swabbed with a cotton-tip swab and washed to remove cells that did not translocate. A total of five random fields per transwell insert were imaged using a 10× objective (NA) and nuclei were averaged.

Tissue Spheroid Generation, Staining, and Quantification

Tissue Spheroid Generation

Tissue spheroids were grown by plating Panc10.05 cells on a drop of Matrigel (Becton-Dickinson) in an 8-well slide chamber (6,500 cells per well) and grown in RPMI 1640 media (2% serum, 2% matrigel, and 10 ng/ml EGF). Spheroids were grown for 14 days with regular media changes, then aspirated off the surface of the matrigel, washed with ice-cold PBS with mild centrifugation (4,000 RCF, 5 min). For all 2D spreading assays, spheroids were then plated on 50 g/ml collagen-coated 8-well coverslips (MatTek) and incubated for 48 hrs in complete PANC media with 500 nM 4-HAP or PBS control. For 3D invasion assays, spheroids were resuspended in a 1.5 mg/ml collagen solution (Life Technologies) and then plated in 8-well chambered coverslips. Spheroids were incubated in complete PANC media with 500 nM 4-HAP or PBS control for 48 hrs. All spheroid samples were fixed in 4% paraformaldehyde for 15 min at 25° C. and permeabilized in 0.1% Triton X-100 for 15 min at 25° C. The actin cytoskeleton was visualized with rhodamine-phalloidin (5 M) for 30 min. Two-dimensional spreading was visualized with Olympus Spinning disk microscope (40× oil objective, 1.30NA) or Nikon-NSIM (100× objective, 1.4NA) with an Andor EMCCD camera controlled by NIS-Elements software. Three-dimensional invasion through collagen was visualized with an Olympus Spinning Disk microscope (20× air, 0.4NA).

Spheroid Cortex Fluorescence Quantification

Quantification of 2D spheroids plated on a thin layer of collagen was performed using a custom-designed Matlab script (Mathworks, Natick, Mass.). A maximum intensity projection of 20 z-slices was extracted from each of the images and converted to 16-bit grayscale before enhancing the pixel intensity (Matlab command: histeq). The enhanced image was then segmented into foreground and background using the Chan-Vese method (activecountour), followed by filtering of small regions (bwareaopen), and morphological erosion (imerode). The boundary from this object was then obtained (bwboundary) and average background intensity was subtracted. This method was used for more than 80% of the images. If this boundary did not accurate reflect the shape of the spheroid, a manual tracing option was offered. This option allowed the user to select a region of interest surrounding the outer edge of the spheroid (roipoly). Anything outside of this boundary was masked and subsequently not considered (regionfill). Following this, a similar binarization/background subtraction regime was implemented on the unmasked region and the boundary was traced.

For each point along the boundary, a line perpendicular to the edge was computed and the intensity along this line was used to linearize the cortex. The resultant matrix was converted into a grayscale image. The Hough Transform was used to determine the continuity of the actin belt along the edge of the cortex. Linearized cortex images were binarized using a threshold chosen to best differentiate belt from non-belt for each set of images (imbinarize), followed by filtering of small regions (bwareaopen), and morphological dilation (imdilate). The Hough Transform was performed on this image (hough), and Hough peaks and lines identified (houghpeaks, houghlines). These were used to create a continuity score defined by (E Hough line lengths)/(number of lines+length of image). In this metric, higher scores indicate a more continuous actin belt at the cortex. Additionally, we computed: a coarseness index of the cortex (std2) to describe actin distribution, the percentage of white pixels of the binarized image to characterize actin belt thickness, and the ratio of white pixels to gray pixels (greater than 0.15) to describe the distribution of fluorescence.

Mouse Studies

Hemi-Splenectomies

Hemi-splenectomies were performed on athymic NCr-nu/nu mice (Charles River Laboratories) with low passage AsPC-1 cells as previously described. In short, laparotomies were performed on anesthetized mice in which the upper pole of a divided spleen was reinserted into the peritoneum while $1\times10^7$ AsPC-1 cells prepared in phosphate buffered saline were injected into the lower splenic pole, chased by an equal volume of phosphate buffered saline. The pancreas and splenic vessels were ligated and the peritoneum was closed.

AsPC-1 cells were pretreated with 50 µM 4-HAP or PBS 24 hr prior to injection during hemisplenectomies. Mice were also weighed and treated intraperitoneally with 200 µl of 5 mg/ml of 4-HAP or 200 µl PBS two days prior to surgery, and then treatment was continued every other day, starting on day 1 post-surgery. Mice were sacrificed upon spontaneous death of the first mouse. Samples from the mice of both this study and the survivability study were harvested as described below.

Livers were washed, weighed, photographed, and fixed in 10% formalin in PBS for 48 hrs, embedded in paraffin blocks, and sectioned as 4-µm thick slides. Mice were housed and handled according to approved Institutional Animal Care and Use Committee protocols.

Mouse Liver Tumor Quantification

Quantifications of mouse livers were performed using a custom-designed Matlab script. RGB images were first separated into their three component channels. The image-Segmenter tool on Matlab was used to segment the individual channels identifying the area of the whole liver, the area of the tumor, and the area/location of the glare on the images, which was removed from the tumor area. The percent coverage of tumor was calculated.

The present invention has been described in terms of one or more preferred embodiments, and it should be appreciated that many equivalents, alternatives, variations, and modifications, aside from those expressly stated, are possible and within the scope of the invention.

REFERENCES

1. Moser, T. L., Kenan, D. J., Ashley, T. A., Roy, J A., Goodman, M. D., Misra, U. K., Cheek, D. J., and Pizzo, S. V. (2001). Endothelial cell surface F1-F0 ATP synthase is active in ATP synthesis and is inhibited by angiostatin. Proc Natl Acad Sci USA 98, 6656-6661.
2. Malik, F. I., Hartman, J. J., Elias, K A., Morgan, B. P., Rodriguez, H., Brejc, K., Anderson, R. L., Sueoka, S. H., Lee, K. H., Finer, J. T., et al. (2011). Cardiac myosin activation: a potential therapeutic approach for systolic heart failure. Science 331, 1439-1443.
3. Straight, A. F., Cheung, A., Limouze, J., Chen, I., Westwood, N. J., Sellers, J. R., and Mitchison, T. J. (2003). Dissecting temporal and spatial control of cytokinesis with a myosin II inhibitor. Science 299, 1743-1747.
4. Ostap, E. M. (2002). 2,3-Butanedione monoxime (BDM) as a myosin inhibitor. J Muscle Res Cell Motil 23, 305-308.
5. Ishihara, H., Martin, B. L., Brautigan, D. L., Karaki, H., Ozaki, H., Kato, Y., Fusetani, N., Watabe, S., Hashimoto, K., Uemura, D., et al. (1989). Calyculin A and okadaic acid: inhibitors of protein phosphatase activity. Biochem Biophys Res Commun 159, 871-877.
6. Ishihara, H., Ozaki, H., Sato, K., Hori, M., Karaki, H., Watabe, S., Kato, Y., Fusetani, N., Hashimoto, K., Uemura, D., et al. (1989). Calcium-independent activation of contractile apparatus in smooth muscle by calyculin-A. J Pharmacol Exp Ther 250, 388-396.
7. Makishima, M., Honma, Y., Hozumi, M., Sampi, K., Hattori, M., and Motoyoshi, K. (1991). Induction of differentiation of human leukemia cells by inhibitors of myosin light chain kinase. FEBS Lett 287, 175-177.
8. Saitoh, M., Ishikawa, T., Matsushima, S., Naka, M., and Hidaka, H. (1987). Selective inhibition of catalytic activity of smooth muscle myosin light chain kinase. J Biol Chem 262, 7796-7801.
9. Uehata, M., Ishizaki, T., Satoh, H., Ono, T., Kawahara, T., Morishita, T., Tamakawa, H., Yamagami, K., Inui, J., Maekawa, M., et al. (1997). Calcium sensitization of smooth muscle mediated by a Rho-associated protein kinase in hypertension. Nature 389, 990-994.
10. Luo T, et al. (2012) Understanding the cooperative interaction between myosin II andactin cross-linkers mediated by actin filaments during mechanosensation. *Biophys. J.* 102(2):238-247.
11. Murphy C T, Rock R S, & Spudich J A (2001) A myosin II mutation uncouples ATPase activity from motility and shortens step size. *Nat. Cell Biol.* 3:311-315.
12 Reichl E M, et al. (2008) Interactions between myosin and actin crosslinkers control cytokinesis contractility dynamics and mechanics. *Curr. Biol.* 18(7):471-480.
13. Girard K D, Kuo S C, & Robinson D N (2006) *Dictyostelium* myosin II mechanochemistry promotes active behavior of the cortex on long time scales. *Proc Natl Acad Sci USA* 103(7):2103-2108.
14. Ren Y, et al. (2009) Mechanosensing through cooperative interactions between myosin II and the actin cross-linker cortexillin. *Curr Biol* 19(17):1421-1428.
15. Luo T, Mohan K, Iglesias P A, & Robinson D N (2013) Molecular mechanisms of cellular mechanosensing. *Nat. Mater.* 12:1064-1071.
16. Kee Y S, et al. (2012) A mechanosensory system governs myosin II accumulation in dividing cells. *Mol Biol Cell* 23:1510-1523.
17. Robinson D N & Spudich J A (2000) Dynacortin, a genetic link between equatorial contractility and global shape control discovered by library complementation of a *Dictyostelium discoideum* cytokinesis mutant. *J. Cell Biol.* 150(4):823-838.
18. Ruppel K M & Spudich J A (1995) Myosin motor function: structural and mutagenic approaches. *Curr Opin Cell Biol* 7(1):89-93.
19. Gerald N, Dai J, Ting-Beall H P, & De Lozanne A (1998) A role for *Dictyostelium* racE in cortical tension and cleavage furrow progression. *J Cell Biol* 141(2):483-492.
20. Lakshmikanth G, Warrick H M, & Spudich J A (2004) A mitotic kinesin-like protein required for normal karyokinesis, myosin localization to the furrow, and cytokinesis in *Dictyostelium*. Proc. Natl. Acad. Sci. USA 101(47): 16519-16524.
21. Effler J C, et al. (2006) Mitosis-specific mechanosensing and contractile-protein redistribution control cell shape. *Curr Biol* 16(19):1962-1967.
22. Kee Y-S & Robinson D N (2013) Micropipette Aspiration for Studying Cellular Mechanosensory Responses and Mechanics. *Dictyostelium* Protocols II: Methods Mol. Biol. 983:367-382.

23. Derganc J, Bozic B, Svetina S, & Zeks B (2000) Stability analysis of micropipette aspiration of neutrophils. *Biophys J* 79(1):153-162.
24. Octtaviani E, Effler J C, & Robinson D N (2006) Enlazin, a natural fusion of two classes of canonical cytoskeletal proteins, contributes to cytokinesis dynamics. *Mol. Biol. Cell* 17(12):5275-5286.
25. Yumura S, et al. (2005) Multiple myosin II heavy chain kinases: roles in filament assembly control and proper cytokinesis in *Dictyostelium*. *Mol. Biol. Cell* 16(9):4256-4266.
26. Zhou Q et al. (2010) 14-3-3 coordinates microtubules, Rac, and myosin II to control cell mechanics and cytokinesis. *Curr Biol* 20(21):1881-1889.
27. Norstrom M F, Smithback P A, & Rock R S (2010) Unconventional processive mechanics of non-muscle myosin IIB. *J Biol Chem* 285(34):26326-26334.
28. Reichl E M & Robinson D N (2007) Putting the brakes on cytokinesis with alpha-actinin. *Dev. Cell* 13:460-462.
29. Betapudi V, Licate L S, & Egelhoff T T (2006) Distinct roles of nonmuscle myosin II isoforms in the regulation of MDA-MB-231 breast cancer cell spreading and migration. *Cancer Res* 66(9):4725-4733.
30. Betapudi V, Gokulrangan G, Chance M R, & Egelhoff T T (2011) A proteomic study of myosin II motor proteins during tumor cell migration. *J Mol Biol* 407(5):673-686.
31. Heisenberg C P & Bellaiche Y (2013) Forces in tissue morphogenesis and patterning. *Cell* 153(5):948-962.
32. Mahajan R K & Pardee J D (1996) Assembly mechanism of *Dictyostelium* myosin II: Regulation by K+, Mg2+, and actin filaments. Biochemistry 35:15504-15514.
33. Niederman R & Pollard TD (1975) Human platelet myosin. II. In vitro assembly and structure of myosin filaments. J. Cell Biol. 67:72-92.
34. Egelhoff T T, Lee R J, & Spudich J A (1993) *Dictyostelium* myosin heavy chain phosphorylation sites regulate myosin filament assembly and localization in vivo. Cell 75:363-371.
35. Robinson D N, Cavet G, Warrick H M, & Spudich J A (2002) Quantitation of the distribution and flux of myosin-II during cytokinesis. BMC Cell Biol 3:4.
36. Delpu Y, et al. (2011) Genetic and epigenetic alterations in pancreatic carcinogenesis. Curr Genomics 12(1):15-24.
37. Sun Q et al. (2014) Competition between human cells by entosis. *Cell Res.* 24(11):1299-1310.
38. Maitra A, et al. (2003) Global expression analysis of well-differentiated pancreatic endocrine neoplasms using oligonucleotide microarrays. *Clin Cancer Res* 9(16 Pt 1):5988-5995.
39. Maitra A, et al. (2003) Multicomponent analysis of the pancreatic adenocarcinoma progression model using a pancreatic intraepithelial neoplasia tissue microarray. *Mod Pathol* 16(9):902-912.
40. Tan M H & Chu T M (1985) Characterization of the tumorigenic and metastatic properties of a human pancreatic tumor cell line (AsPC-1) implanted orthotopically into nude mice. *Tumour Biol* 6(1):89-98.
41. D'Apolito M, Guarnieri V, Boncristiano M, Zelante L, & Savoia A (2002) Cloning of the murine non-muscle myosin heavy chain IIA gene ortholog of human MYH9 responsible for May-Hegglin, Sebastian, Fechtner, and Epstein syndromes. *Gene* 286(2):215-222.
42. Jones S, et al. (2008) Core signaling pathways in human pancreatic cancers revealed by global genomic analyses. *Science* 321(5897):1801-1806.
43. Marini M, et al. (2006) Non-muscle myosin heavy chain IIA and IIB interact and co-localize in living cells: relevance for MYH9-related disease. *Int J Mol Med* 17(5): 729-736.
44. Even-Ram S & Yamada K M (2007) Of mice and men: Relevance of cellular and molecular characterizations of myosin IIA to MYH9-related human disease. *Cell Adh Migr* 1(3):152-155.
45. Dupont S, et al. (2011) Role of YAP/TAZ in mechanotransduction. *Nature* 474(7350):179-183.
46. Calvo F, et al. (2013) Mechanotransduction and YAP-dependent matrix remodelling is required for the generation and maintenance of cancer-associated fibroblasts. *Nat Cell Biol* 15(6):637-646.
47. Liang S, et al. (2011) MicroRNA let-7f inhibits tumor invasion and metastasis by targeting MYH9 in human gastric cancer. *PLoS One* 6(4):e18409.
48. Schramek D, et al. (2014) Direct in vivo RNAi screen unveils myosin IIa as a tumor suppressor of squamous cell carcinomas. *Science* 343(6168):309-313.
49. Surcel A, Kee Y S, Luo T, & Robinson D N (2010) Cytokinesis through biochemicalmechanical feedback loops. *Semin Cell Dev Biol* 21(9):866-873.
50. Cross S E, Jin Y S, Rao J, & Gimzewski J K (2007) Nanomechanical analysis of cells from cancer patients. *Nat Nanotechnol* 2(12):780-783.
51. Vallini G, Frassinetti S, D'Andrea F, Catelani G, & Agnolucci M (2001) Biodegredation of 4-(1-nonyl)phenol by axenic cultures of the yeast *Candida* aquaetextoris: identification of microbial breakdown products and proposal of a possible metabolic pathway. *Int. Biodeter. Biodegr.* 47:133-140.
52. Tanihata Y, Watanabe M, Mitsukura K, & Maruyama K (Oxidative degradation of 4-hydroxyacetophenone in *Arthrobacter* sp. TGJ4. *Biosci Biotechnol Biochem* 76(4): 838-840.
53. Choi D H, Lee Y J, Kim J S, Kang D G, & Lee H S (2012) *Cynanchum* wilfordii ameliorates hypertension and endothelial dysfunction in rats fed with high fat/cholesterol diets. *Immunopharmacol Immunotoxicol* 34(1):4-11.
54. Choi D H, et al. (2012) Improved endothelial dysfunction by *Cynanchum* wilfordii in apolipoprotein E(−/−) mice fed a high fat/cholesterol diet. *J Med Food* 15(2): 169-179.
55. Jiang Y, et al. (2011) Chemical Metabolites of *Cynanchum* wilfordii and the chemotaxonomy of two species of the family Asclepiadacease, *C. wilfordii* and *C. auriculatum*. *Arch Pharm Res* 34(12):2021-2027.
56. Dolara P, Vezzani A, Caderni G, Coppi C, & Torricelli F (1993) Genetic toxicity of a mixture of fifteen pesticides commonly found in the Italian diet. *Cell Biol Toxicol* 9(4):333-343.
57. Akashi T, Kanbe T, & Tanaka K (1994) The role of the cytoskeleton in the polarized growth of the germ tube in *Candida albicans*. *Microbiology* 140 (Pt 2):271-280.
58. Hepler P K & Jackson W T (1969) Isopropyl N-phenylcarbamate affects spindle microtubule orientation in dividing endosperm cells of Haemanthus katherinae Baker. *J Cell Sci* 5(3):727-743.
59. Magistrini M & Szollosi D (1980) Effects of cold and of isopropyl-N-phenylcarbamate on the second meiotic spindle of mouse oocytes. *Eur J Cell Biol* 22(2):699-707.
60. Oliver J M, Krawiec J A, & Berlin R D (1978) A carbamate herbicide causes microtubule and microfilament disruption and nuclear fragmentation in fibroblasts. *Exp Cell Res* 116(1):229-237.

61. Walker G M (1982) Cell cycle specificity of certain antimicrotubular drugs in *Schizosaccharomyces pombe*. *J Gen Microbiol* 128(1):61-71.
62. Clayton L & Lloyd C W (1984) The relationship between the division plane and spindle geometry in *Allium* cells treated with CIPC and griseofulvin: an anti-tubulin study. *Eur J Cell Biol* 34(2):248-253.
63. Girdler F, et al. (2006) Validating Aurora B as an anti-cancer drug target. *J. Cell Sci.* 119:3664-3675.
64. de Weger V A, Beijnen J H, & Schellens J H (2014) Cellular and clinical pharmacology of the taxanes docetaxel and paclitaxel—a review. *Anticancer Drugs*.
65. Discher D E, Janmey P, & Wang Y L (2005) Tissue cells feel and respond to the stiffness of their substrate. *Science* 310(5751):1139-1143.
66. Bhadriraju K & Hansen L K (2002) Extracellular matrix- and cytoskeleton-dependent changes in cell shape and stiffness. *Exp Cell Res* 278(1):92-100.
67. Chiang A C & Massague J (2008) Molecular basis of metastasis. *N Engl J Med* 359(26):2814-2823.
68. Wakatsuki T, Schwab B, Thompson N C, & Elson E L (2001) Effects of cytochalasin D and latrunculin B on mechanical properties of cells. *J Cell Sci* 114(Pt 5):1025-1036.

We claim:

1. A method for modulating cell mechanics in a disease cell that expresses nonmuscle myosin IIB, nonmuscle myosin IIC, or a combination thereof in a subject comprising:

administering to the subject, an effective amount of a pharmaceutical composition comprising an effective amount of a compound of 4-hydroxyacetophenone or a salt, solvate, or stereoisomer thereof:

and modulating cell mechanics in the subject; and wherein the disease cell is from a pancreatic cancer.

2. The method of claim 1 wherein myosin II is activated in the subject compared to a reference subject that has not been administered the effective amount of the compound.

3. The method of claim 1, wherein the method of administering is systemic delivery selected from the group consisting of oral, parenteral, intranasal, sublingual, rectal, and transdermal administration.

4. The method of claim 1, further comprising the step of administering a bioactive agent.

5. The method of claim 4, wherein the bioactive agent is a compound having a formula:

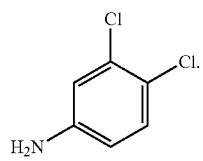

(VI)

6. The method of claim 4, wherein the bioactive agent is a chemotherapy agent.

7. The method of claim 1 wherein the subject has a disease that is treated or prevented by modulating the cell mechanics of the subject.

8. The method of claim 1 wherein the cancer is pancreatic cancer.

9. A method of treating cancer in a subject comprising administering to a subject having cancer that expresses nonmuscle myosin IIB, nonmuscle myosin IIC, or a combination thereof in a subject a pharmaceutical composition comprising an agent selected from the group comprising a salt, solvate or stereoisomer of compound (VIII):

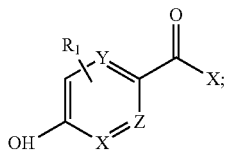

(VIII)

wherein X, Y, and Z can independently be N or C, with the proviso that X, Y, and Z cannot all be N, and wherein $R_1$ is H, OH, Halo, cyano, nitro, $C_1$-$C_6$ alkyl, carboxy $C_1$-$C_6$ alkyl, dicarboxy $C_1$-$C_6$ alkyl, $NR_2R_3$, wherein $R_2$ and $R_3$ are independently represent hydroxy, $C_1$ to $C_{10}$ alkyl, alkylamino, alkenyl, alkynyl, hydroxyalkyl, alkoxy, dialkylamino thioalkyl, thioalkenyl, thioalkynyl, aryloxy, acyloxy, thioacyl, amido, and sulphonamido, and wherein X' is independently represent H, OH, $R_7$, $OR_7$, $NR_7R_8$, wherein $R_7$ and $R_8$ are independently $C_1$-$C_6$ alkyl, carboxy $C_1$-$C_6$ alkyl, dicarboxy $C_1$-$C_6$ alkyl, aryl, heteroaryl, alkenyl, alkynyl, hydroxyalkyl, alkoxy, dialkylamino thioalkyl, thioalkenyl, thioalkynyl, aryloxy, acyloxy, thioacyl, amido, or sulphonamido; and activating nonmuscle myosin IIB, nonmuscle myosin IIC, or a combination thereof, and treating pancreatic in the subject, the method further comprises the step of administering a bioactive agent having a formula:

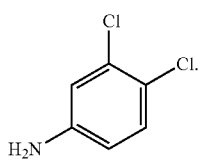

(VI)

10. The method of claim 9, wherein the bioactive agent comprises a chemotherapy agent.

11. The method of claim 9 wherein the compound of Formula VIII is 4-hydroxyacetophenone.

12. The method of claim 1 wherein the cancer is pancreatic cancer.

13. The method of claim 1 wherein the cancer is pancreatic ductal adenocarcinoma.

14. A method of treating pancreatic cancer in a subject comprising administering to a subject an effective amount of a compound of 4-hydroxyacetophenone or salt, solvate or stereoisomer thereof,
thereby treating the pancreatic cancer in the subject.

15. The method of claim 14 wherein the subject is suffering from pancreatic cancer.

16. The method of claim 14, wherein the subject is suffering from pancreatic ductal adenocarcinoma.

17. A method for modulating cell mechanics in a disease cell that expresses nonmuscle myosin IIB, nonmuscle myosin IIC, or a combination thereof in a subject comprising:
administering to the subject, an effective amount of a pharmaceutical composition comprising an effective amount of a compound (VIII) or a salt, solvate, or stereoisomer thereof:

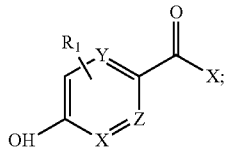

(VIII)

wherein X, Y, and Z can independently be N or C, with the proviso that X, Y, and Z cannot all be N, and wherein $R_1$ is H, OH, halo, cyano, nitro, $C_1$-$C_6$ alkyl, carboxy $C_1$-$C_6$ alkyl, dicarboxy $C_1$-$C_6$ alkyl, $NR_2R_3$, wherein $R_2$ and $R_3$ are independently OH, $C_1$ to $C_{10}$ alkyl, alkylamino, alkenyl, alkynyl, hydroxyalkyl, alkoxy, dialkylamino thioalkyl, thioalkenyl, thioalkynyl, aryloxy, acyloxy, thioacyl, amido, and sulphonamido, and wherein X' is H, OH, $R_1$, $OR_1$, $NR_1Rs$, wherein $R_1$ and Rs, are independently $C_1$-$C_6$ alkyl, carboxy $C_1$-$C_6$ alkyl, dicarboxy $C_1$-$C_6$ alkyl, aryl, heteroaryl, alkenyl, alkynyl, hydroxyalkyl, alkoxy, dialkylamino thioalkyl, thioalkenyl, thioalkynyl, aryloxy, acyloxy, thioacyl, amido, or sulphonamido;
administering a bioactive agent comprising a compound having a formula:

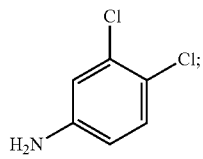

(VI)

and
modulating cell mechanics in the subject; and
wherein the disease cell is a cell from a pancreatic cancer.

18. A method of treating a cancer in a subject comprising:
administering to a subject having the cancer that expresses nonmuscle myosin IIB, nonmuscle myosin IIC, or a combination thereof in a subject a pharmaceutical composition comprising an effective amount of a compound (VIII) or a salt, solvate, or stereoisomer thereof:

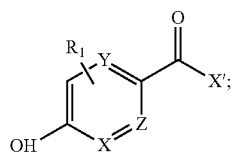

(VIII)

wherein X, Y, and Z can independently be N or C, with the proviso that X, Y, and Z cannot all be N, and wherein $R_1$ is H, OH, halo, cyano, nitro, $C_1$-$C_6$ alkyl, carboxy $C_1$-$C_6$ alkyl, dicarboxy $C_1$-$C_6$ alkyl, $NR_2R_3$, wherein $R_2$ and $R_3$ are independently OH, $C_1$ to $C_{10}$ alkyl, alkylamino, alkenyl, alkynyl, hydroxyalkyl, alkoxy, dialkylamino thioalkyl, thioalkenyl, thioalkynyl, aryloxy, acyloxy, thioacyl, amido, and sulphonamido, and wherein X' is H, OH, $R_1$, $OR_1$, $NR_1Rs$, wherein $R_1$ and Rs, are independently $C_1$-$C_6$ alkyl, carboxy $C_1$-$C_6$ alkyl, dicarboxy $C_1$-$C_6$ alkyl, aryl, heteroaryl, alkenyl, alkynyl, hydroxyalkyl, alkoxy, dialkylamino thioalkyl, thioalkenyl, thioalkynyl, aryloxy, acyloxy, thioacyl, amido, or sulphonamido;
administering a bioactive agent comprising a compound having a formula:

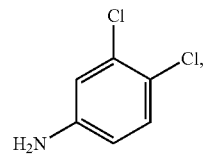

(VI)

wherein the cancer is pancreatic cancer.

* * * * *